US011795130B2

(12) United States Patent
Oroskar et al.

(10) Patent No.: US 11,795,130 B2
(45) Date of Patent: *Oct. 24, 2023

(54) PROCESS FOR SEPARATING A CONSTITUENT/CANNABINOID USING A CHROMATOGRAPHIC RESIN

(71) Applicant: Kazmira LLC, Watkins, CO (US)

(72) Inventors: Anil Rajaram Oroskar, Oak Brook, IL (US); David W. House, Arlington Heights, IL (US); Praneeth Dayanthe Edirisinghe, Chicago, IL (US); Asha Anil Oroskar, Oak Brook, IL (US); Faridedin Adel, Arlington Heights, IL (US); Xinjie Chen, Naperville, IL (US); Gautham Anil Oroskar, Oak Brook, IL (US); Kunal Gulati, Naperville, IL (US)

(73) Assignee: Kazmira LLC, Watkins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/392,718

(22) Filed: Aug. 3, 2021

(65) Prior Publication Data

US 2021/0363083 A1 Nov. 25, 2021

Related U.S. Application Data

(63) Continuation of application No. 17/011,780, filed on Sep. 3, 2020, now Pat. No. 11,078,145, which is a continuation of application No. 16/113,947, filed on Aug. 27, 2018, now Pat. No. 10,843,991, which is a continuation-in-part of application No. 15/644,112, filed on Jul. 7, 2017, now Pat. No. 10,189,762.

(51) Int. Cl.
| | | |
|---|---|---|
| *C07C 37/84* | (2006.01) | |
| *C07C 51/42* | (2006.01) | |
| *B01D 15/18* | (2006.01) | |
| *A61K 31/192* | (2006.01) | |
| *C07C 37/68* | (2006.01) | |
| *C07C 37/82* | (2006.01) | |
| *A61K 31/352* | (2006.01) | |
| *A61K 31/05* | (2006.01) | |
| *B01D 15/32* | (2006.01) | |
| *C07C 39/23* | (2006.01) | |
| *C07C 65/19* | (2006.01) | |

(52) U.S. Cl.
CPC .......... *C07C 37/685* (2013.01); *A61K 31/05* (2013.01); *A61K 31/192* (2013.01); *A61K 31/352* (2013.01); *B01D 15/185* (2013.01); *B01D 15/1821* (2013.01); *C07C 37/82* (2013.01); *C07C 37/84* (2013.01); *C07C 51/42* (2013.01); *B01D 15/325* (2013.01); *B01D 2257/70* (2013.01); *C07C 39/23* (2013.01); *C07C 65/19* (2013.01); *C07C 2601/16* (2017.05)

(58) Field of Classification Search
CPC ........ C07D 37/84; C07D 51/42; C07D 39/23; B01D 15/1821; B01D 15/185
See application file for complete search history.

(56) References Cited

U.S. PATENT DOCUMENTS

| | | |
|---|---|---|
| 2,304,669 A | 12/1942 | Roger |
| 2,985,589 A | 5/1961 | Broughton |
| 8,343,553 B2 | 1/2013 | Hospodor |
| 9,034,395 B2 | 5/2015 | Whittle |
| 9,044,390 B1 | 6/2015 | Speier |
| 9,199,960 B2 | 12/2015 | Ferri |
| 9,358,259 B2 | 6/2016 | Hospodor et al. |
| 10,189,762 B1 | 1/2019 | Oroskar et al. |
| 10,413,845 B1 | 9/2019 | Tegen et al. |
| 10,414,709 B1 | 9/2019 | Tegen et al. |
| 10,604,464 B2 | 3/2020 | Oroskar et al. |
| 10,799,546 B1 | 10/2020 | Jansen et al. |
| 10,843,991 B2 | 11/2020 | Oroskar et al. |
| 2004/0033280 A1 | 2/2004 | Whittle |
| 2005/0266108 A1 | 12/2005 | Flockhart et al. |
| 2006/0167283 A1 | 7/2006 | Flockhart et al. |
| 2008/0167483 A1 | 7/2008 | Whittle et al. |
| 2012/0294887 A1 | 11/2012 | Saunois et al. |

(Continued)

FOREIGN PATENT DOCUMENTS

| | | |
|---|---|---|
| EP | 1536810 B1 | 8/2012 |
| WO | 2003/074144 A2 | 9/2003 |

(Continued)

OTHER PUBLICATIONS

Brett Konen, "Why Ethanol Works So Well for Cannabis Extraction," Capna Labs, https://www.leafly.com/news/industry/ethanol-cannabis-extraction (Aug. 31, 2016).

HPLC-015 Application News—"Potency Testing in Cannabis Extracts Using a High Resolution Method with Cannabis Analyzer for Potency," Shimadzu Corporation (Feb. 2017).

HPLC-016 Application News—"Potency Testing in Cannabis Extracts Using a High Sensitivity Method with Cannabis Analyzer for Potency," Shimadzu Corporation (Feb. 2017).

(Continued)

*Primary Examiner* — Sikarl A Witherspoon
(74) *Attorney, Agent, or Firm* — Leydig, Voit & Mayer, Ltd.

(57) ABSTRACT

A method for purification and separation of cannabinoids, such as cannabidiol and tetrahydrocannabinol, e.g., from dried hemp and *cannabis* leaves can use a continuous simulated moving bed process, a batch column chromatography method, or a single column, and a combination of one or more of a sequence of purification steps including: filtration, decolorization, activation or decarboxylation, dewaxing, polishing, and crystallization to separate a cannabinoid from the *cannabis* plant and to provide various cannabinoid products. The cannabinoid products can be used in various pharmaceutical and nutraceutical applications.

40 Claims, 20 Drawing Sheets

(56) References Cited

U.S. PATENT DOCUMENTS

| | | |
|---|---|---|
| 2015/0126596 A1 | 5/2015 | Gutman et al. |
| 2018/0200315 A1 | 7/2018 | Silver |
| 2018/0206518 A1 | 7/2018 | Silver |
| 2018/0333446 A1 | 11/2018 | Shan et al. |
| 2018/0362429 A1 | 12/2018 | Zhang et al. |
| 2019/0144414 A1 | 5/2019 | Erfurt et al. |
| 2019/0210946 A1 | 7/2019 | Qu et al. |
| 2019/0276420 A1 | 9/2019 | Tegen et al. |

FOREIGN PATENT DOCUMENTS

| | | |
|---|---|---|
| WO | 2004/026802 A1 | 4/2004 |
| WO | 2016/187679 A1 | 12/2016 |
| WO | 2017/026897 A1 | 2/2017 |
| WO | 2017/194173 A1 | 11/2017 |
| WO | 2019/010419 A1 | 1/2019 |
| WO | 2019/173582 A1 | 9/2019 |

OTHER PUBLICATIONS

HPLC-017 Application News—"Potency Testing in Cannabis Extracts Using a High Throughput Method with Cannabis Analyzer for Potency," Shimadzu Corporation (Feb. 2017).

Meyer et al., "Development of a rapid method for the sequential extraction and subsequent quantification of fatty acids and sugars from avocado mesocarp tissue," *J Agric Food Chem.*, Aug. 27, 2008; 56(16):7439-45. doi: 10.1021/jf8011322. Epub Aug. 5, 2008.

"Pros and Cons of Hemp Oil Extraction Techniques," Elixinol LLC, https://elixinolcbd.eom/blogs/buyers-guide/16641671-pros-and-cons-of-hemp-oil-extraction-techniques (Mar. 12, 2015).

European Patent Office, International Search Report and the Written Opinion in International Application No. PCT/US2018/041096 (dated Oct. 31, 2018).

European Patent Office, International Search Report and the Written Opinion in International Application No. PCT/US2019/048160 (dated Jan. 24, 2020).

PROCESS FOR SEPARATING A CONSTITUENT/CANNABINOID USING A CHROMATOGRAPHIC RESIN

CROSS-REFERENCE TO RELATED APPLICATIONS

This patent application is a continuation of U.S. patent application Ser. No. 17/011,780, filed Sep. 3, 2020, which is a continuation of U.S. patent application Ser. No. 16/113,947, filed Aug. 27, 2018, which is a continuation-in-part of U.S. patent application Ser. No. 15/644,112, filed Jul. 7, 2017, and entitled, "Process for Purification and Separation of Cannabinoids, from Dried Hemp and Cannabis Leaves," each of which is incorporated in its entirety herein by this reference.

BACKGROUND

The legalization of medicinal Cannabis is occurring across the United States and in many other countries. As a result, the global demand for cannabinoids is increasing. In addition, a number of recent medical studies report health benefits of many cannabinoids. Cannabis contains over 85 cannabinoids, most of them have been found to have therapeutically beneficial properties. The most widely known cannabinoids found in cannabis known to have the most therapeutic properties are cannabidiol (CBD) and tetrahydrocannabinol (THC). A number of other cannabinoids, such as cannabigerol (CBG) and cannabinol (CBN), also have been shown to exhibit health benefits.

Cannabinoids are generally known as being psychoactive; however, the psychoactive properties of cannabinoid products depend on the amount of tetrahydrocannabinol (THC) in the products. Accordingly, there is demand for cannabinoid products that are essentially free of tetrahydrocannabinol (THC), or do not contain tetrahydrocannabinol (THC).

Recently, a number of medical applications for cannabidiol (CBD) relate to treatment of conditions that effect children. Because physicians and parents do not want their children consuming a psychoactive product, there is growing demand for cannabidiol (CBD) without tetrahydrocannabinol (THC). Associated with this demand for a tetrahydrocannabinol (THC) free product, there is a demand for botanically derived and extracted products, rather than synthetically derived products.

The terms hemp and cannabis refer to the genus Cannabis, which contains three species Cannabis sativa, Cannabis indica, and Cannabis ruderalis. All three species are of the family Cannabaceae, which also includes the genus Humulus, or hops. Cannabis is a flowering plant that is indigenous to central Asia and India. Humans have been cultivating and using cannabis for thousands of years, going back to the ancient Romans, Greeks, and the Islamic empires of the Middle East and Africa.

There are at least 113 different cannabinoids present in the cannabis plant. All of the classes of cannabinoids are derived from a common precursor compound, cannabigerol (CBG). The cannabis plant also contains a variety of terpenoids. Most such compounds are lipophilic and phenolic.

Below are the structures of many common cannabinoids:

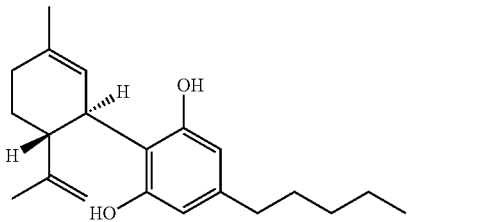
Cannabidiol (CBD)

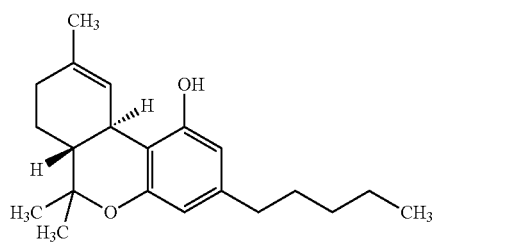
Tetrahydrocannabinol (THC)

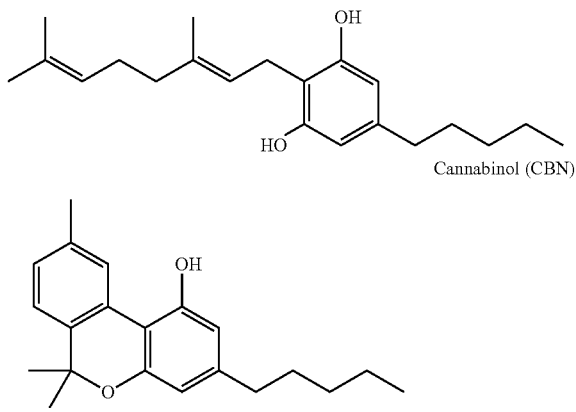
Cannabigerol (CBG)

Cannabinol (CBN)

Cannabinoids can be extracted from dried hemp and cannabis leaves of the three species Cannabis sativa, Cannabis indica, and Cannabis ruderalis using a hydrocarbon solvent such as butane, a supercritical solvent such as carbon dioxide, or ethanol. Butane extraction and supercritical $CO_2$ extraction, have accounted for the majority of production of cannabinoid concentrates currently available on the market. A third extraction method, based on ethanol has been gaining market share as a solvent of choice for manufacturing high-quality cannabis extracts.

Butane is a gas at standard conditions, and requires the extraction to be carried out at above atmospheric pressure. Following the extraction, butane is relatively easy to purge from the resulting extract because of its lower boiling point. However, the largest drawback to using butane for the extraction of cannabinoids is safety. Butane is highly combustible, and its use has resulted in a number of explosions in small extractors. Furthermore, there is concern that if the butane is not pure, undesirable and potentially toxic hydrocarbons can end up in the extract product.

Liquid carbon dioxide can be employed to extract cannabidiol (CBD) and other cannabinoids from the cannabis plant. The extraction is performed using liquid carbon dioxide ($CO_2$) in its super-critical range, typically at extraction temperatures above 31° C. and pressures above 74 bar. According to the super critical extraction process, the solid matrix (leaves) to be extracted is loaded into a pressurized chamber, into which the liquid carbon dioxide is then pumped. The desired extractable component, cannabidiol (CBD), will dissolve in the carbon dioxide to form a solution. The resulting solution is pumped into a settling chamber, which is at a lower pressure. At the reduced pressure of the settling chamber, the dissolved solid precipitates. Solubility of the cannabidiol in the supercritical fluid is directly related to pressure. Once the solute has precipitated out of the solution the carbon dioxide will be pumped out and will be recompressed for further use in extraction. Supercritical $CO_2$ extraction is effective because: 1) $CO_2$ is inert and non-toxic, and 2) $CO_2$ is non polar. However, $CO_2$ will also extract many plant waxes, lipids, and other non-polar and undesired components. Because supercritical $CO_2$ extraction must be run at high pressure, there is additional cost and safety problems with the extraction equipment and apparatus itself.

Even though ethanol is safer than butane and more effective than supercritical $CO_2$, a standard ethanol extraction introduces other difficulties. The polar nature of ethanol allows ethanol to readily mix with water and dissolve water soluble molecules during the extraction process. This results in a greater amount of impurities being introduced into the extract. For example, chlorophyll will be co-extracted with ethanol and the resulting extract will have a dark color and an unpleasant taste. As a result, using ethanol extraction requires a large number of downstream purification steps, including expensive column chromatography, in order to meet pharmaceutical purity specifications.

U.S. Patent Application Publication No. US2006/0167283 A1 discloses methods to purify and isolate cannabidiol (CBD) from dried plant material which include (a) decarboxylating the leaves (b) extracting cannabinoids using supercritical carbon dioxide (c) precipitation using $C_1$-$C_{12}$ alcohol (d) filtration (e) redissolving the cannabidiol enriched extract into pentane (f) removal of insoluble material and (g) evaporation of solvent producing crystals.

U.S. Pat. No. 9,034,395 discloses a method for preparing extracts of natural products such as plant material, and for preparing purified extracts from crude extracts of natural products, by extraction with hot gas. The cannabinoids are volatilized at a high temperature along with a heated gas. The cannabinoids are volatilized in one or more stages at increasing temperatures, and the volatilized components are condensed and collected at one or both stages.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

Conventional methods for the purification of cannabinoids are associated with a large number of downstream purification steps, including expensive column chromatography, in order to meet high purity specifications. Methods are sought to purify and recover a cannabidiol (CBD) rich oil which contains essentially no THC. To satisfy the growing demand for the cannabidiol (CBD) oil being essentially free of tetrahydrocannabinol (THC), there is a need for an efficient extraction process that can be carried out on a commercial scale to produce high purity cannabidiol (CBD) products. The potential for even small amounts of THC remaining in the purified CBD oil product can be undesirable.

SUMMARY

Embodiments of the present disclosure are directed to methods for the purification and separation of cannabinoids from dried hemp and *cannabis* leaves. For example, the methods of the disclosure can be used to separate a desired cannabinoid (e.g., cannabidiol), i.e., to increase its purity, from other cannabinoids, such as tetrahydrocannabinol.

Thus, in some aspects, a method of separating a cannabinoid from a *cannabis* plant can be used to process a *cannabis* plant including the cannabinoid and at least one impurity. The method includes combining the *cannabis* plant and a solvent to form a crude *cannabis* extract stream. The crude *cannabis* extract stream is processed into a simulated moving bed (SMB) feedstock stream by removing at least a portion of at least one impurity in the crude *cannabis* extract stream. The SMB feedstock stream is passed through a SMB zone to provide a primary raffinate stream having a higher purity of the cannabinoid than in the SMB feedstock stream as measured by weight percentage of the solid content and a SMB extract stream having a lower purity of the cannabinoid than in the SMB feedstock stream as measured by weight percentage of the solid content.

In some aspects, a method of separating a cannabinoid of a *cannabis* plant can be used to process a *cannabis* plant including the cannabinoid and at least one impurity. The method includes preparing a feedstock stream that includes the *cannabis* plant and a solvent. The feedstock stream is passed through a chromatographic adsorbent to provide an eluate stream. The eluate stream has a higher purity of the cannabinoid than in the feedstock stream as measured by weight percentage of the solid content. The chromatographic adsorbent comprises at least one of: (i) a first adsorbent, the first adsorbent comprising a modified activated carbon adsorbent having an average particle size range of from about 45 to about 1700 microns, (ii) a second adsorbent, the second adsorbent comprising a modified hydrophobic adsorbent having an average bulk density of from about 0.4 g/mL to about 0.6 g/mL, the modified hydrophobic adsorbent comprising at least one of a styrene-divinylbenzene (DVB) resin or a poly(methyl methacrylate) (PMMA) resin, (iii) a third adsorbent, the third adsorbent comprising a hydrophobic resin having an average bulk density of from about 0.75 g/mL to about 0.85 g/mL, (iv) a fourth resin, the fourth resin comprising a hydrophobic polystyrene-divinylbenzene adsorbent having a water content of from about 55% to about 65%, and (v) any mixture thereof.

In some aspects, a method of purifying a composition is used to separate a first constituent from a second constituent. The method includes passing a first feedstock stream through a first chromatographic resin to form a first eluate having a higher ratio of the first constituent to the second constituent than in the first feedstock stream. The first eluate is passed through a second chromatographic resin to form a second eluate having a higher ratio of the first constituent to the second constituent than in the first eluate. A second feedstock stream is passed through the second chromatographic resin to form a third eluate having a higher ratio of the first constituent to the second constituent than in the second feedstock stream. The third eluate is passed through a third chromatographic resin to form a fourth eluate having a higher ratio of the first constituent to the second constituent than in the third eluate.

In some aspects, a method for the purification and separation of cannabinoids includes a sequence of purification steps and a novel simulated moving bed separation (SMB) process to bring about the enrichment and purification of Cannabidiol (CBD) which is essentially pure and is essentially free of Tetrahydrocannabinol (THC). Furthermore, the process provides a highly pure CBD product without using any potentially toxic organic solvent. The feed to the SMB unit incorporates a series of steps which essentially eliminate the presence of THC. The simulated moving bed system employed is a combination of a reverse phase stationary phase adsorbent and a polar mobile phase comprising ethanol and water in a reverse phase simulated moving bed separation zone to provide an enriched raffinate stream comprising cannabinoids, primarily CBD, which is essentially free of tetrahydrocannabinol (THC). A cannabidiol product having a total cannabidiol (CBD) purity greater than 95 weight percent (e.g., 96, 97, 98, 99, 99.9 wt. %) following evaporation or drying can be obtained.

In some aspects, a process for the purification of cannabidiol (CBD) in a crude *cannabis* extract stream provides at least one high purity cannabidiol product selected from the group consisting of a high purity cannabinoid oil stream, a phytocannabinoid rich oil, a solid CBD aggregate, and mixtures thereof being essentially free of tetrahydrocannabinol. The process includes:

a) passing the crude *cannabis* extract stream comprising debris and small particles, cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a first filtration zone comprising a series of successive filters of decreasing pore size, starting at a pore size of 100 microns and reducing to about 10 microns in 3 or more stages to remove debris and small particles in a progressive filtration step to provide a filtered crude cannabinoid stream;

b) passing the filtered crude cannabinoid stream comprising cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a decolorization zone comprising a 10 μm filter and a decolorization chromatographic column containing a modified activated carbon adsorbent which was heat treated to provide a highly hydrophobic adsorbent which is essentially free of hydroxyl groups, has an average particle diameter of between 177 and 250 microns, and an iodine number of above 900 mg/g and operated at a decolorization pressure of 2.72 atm to about 4.08 atm (40-60 psig) and a decolorization temperature ranging from 20-25° C. to remove at least a portion of color bodies and essentially all of the chlorophyll to provide a decolorized extract stream;

c) passing the decolorized extract stream to a first evaporation zone operated at a first vacuum pressure of −0.60 to about −0.74 atm (−18 to −22 in Hg) and a temperature of about 90 to about 110° C. to remove at least a portion of the ethanol to provide an evaporated extract stream which is essentially free of ethanol;

d) passing the evaporated extract stream comprising cannabidiol (CBD), cannabidiolic acid (CBDA), tetrahydrocannabinolic acid (THCA), tetrahydrocannabinol (THC), sugars and carbohydrates, lipids, plant waxes, impurities and other cannabinoids to an activation zone and therein subjected to a carboxylation reaction at a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion, said decarboxylation reaction time being sufficient to fully decarboxylate essentially all of the cannabidiolic acid (CBDA) and tetrahydrocannabinolic acid (THCA) to provide a decarboxylated cannabinoid oil comprising cannabidiol (CBD), tetrahydrocannabinol (THC), lipids, plant waxes, and other cannabinoids, and being essentially free of cannabidiolic acid (CBDA) and tetrahydrocannabinolic acid (THCA), and water washing the decarboxylated cannabinoid oil to remove at least a portion of the impurities to provide a washed decarboxylated cannabinoid oil;

e) admixing the washed decarboxylated cannabinoid oil with a dewaxing solvent having a dewaxing solvent volume ratio of 80 volume units of ethanol to 20 volume units water to provide a dewaxing feed stream and passing the dewaxing feed stream to a dewaxing zone containing a dewaxing column at a dewaxing column pressure of about 2.72 atm to about 4.08 atm (40-60 psi) and room temperature (20-25° C.), said dewaxing column containing a hydrophobic activated carbon adsorbent which is essentially free of hydroxyl groups, and having an average particle diameter of between 177 and 250 microns, and an iodine number of above 900 mg/g to remove at least a portion of the lipids and plant waxes and to provide a dewaxed cannabinoid oil stream comprising cannabidiol (CBD), tetrahydrocannabinol (THC), sugars and carbohydrates, color bodies, and other cannabinoids;

f) passing the dewaxed cannabinoid oil stream and a mobile phase desorbent stream consisting of a mixture of food grade ethanol and water to a reversed phase simulated moving bed zone comprising a plurality of adsorbent beds containing a modified hydrophobic adsorbent comprising a styrene-divinylbenzene (DVB) resin having 4 to 8 percent crosslinking or a poly (methyl methacrylate) (PMMA) resin, said modified hydrophobic adsorbent having an average particle diameter of between 25 and 300 microns, an average bulk density (g/mL) of from 0.4 to 0.6, an average surface area ($m^2$/g) of from 450 to 550, and an average pore volume of from 0.70-0.90 (mL/g) to provide a primary raffinate stream comprising cannabidiol (CBD), mobile phase desorbent, sugars and carbohydrates, color bodies, and other cannabinoids and being essentially free of tetrahydrocannabinol (THC), an extract stream comprising mobile phase desorbent, cannabidiol (CBD), and tetrahydrocannabinol (THC), and a secondary raffinate stream comprising mobile phase desorbent, cannabidiol (CBD) which is admixed with the mobile phase desorbent and returned to the reversed phase simulated moving bed zone;

g) passing the primary raffinate to a second evaporation zone to remove mobile phase desorbent to provide a second recovered solvent stream comprising the mobile phase desorbent and to provide the high purity cannabinoid oil stream having an average cannabidiol purity of greater than 80 wt. % and being essentially free of tetrahydrocannabinol (THC);

h) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids;

i) passing a portion of the supernatant non-polar solution to a second filtration zone to remove the precipitate and to provide a filtered supernatant non-polar solution;

j) passing the filtered supernatant non-polar solution to a third evaporation zone to remove at least a portion of the non-polar solvent to provide an evaporated cannabinoid oil stream and a recovered non-polar solvent stream, and returning at least a portion of the recovered non-polar solvent stream to the polishing zone to be admixed with the non-polar solvent;

k) passing the evaporated cannabinoid oil stream to a wash zone and alternately washing the evaporated cannabinoid oil stream first with an ethanol wash stream comprising pure ethanol in a washing ratio of 1:3 liters of ethanol to kilograms of evaporated cannabinoid oil, and second with a fourth water wash stream in a water wash ratio of 1:3 liters of water to kilograms of evaporated cannabinoid oil, and wherein following each step, washed cannabinoid oil is evaporated to dryness to provide a phytocannabinoid rich oil which is essentially free of tetrahydrocannabinol (THC) and comprising greater than 80 wt. % cannabinoid (CBD);

l) passing a portion of the supernatant non-polar solution to a isolate chromatography zone comprising a first isolate chromatography column and a second isolate chromatography column being in serial fluid communication and wherein the first isolate chromatography column contains a modified hydrophilic adsorbent comprising a spherical polar silica adsorbent having a high level of silanol groups, an average particle diameter of between 60 and 200 microns, an average surface area of between 450 to 550 $m^2/g$ an average pore volume of between 0.7 and 0.85 mL/g and a pore size of between 0.005 and 0.0075 microns, wherein the second isolate chromatography column contains an activated alumina adsorbent having an average particle diameter of between 50 to 200 microns, an average bulk density of 0.85 g/ml, an average surface area of between 140 and 170 $m^2/g$, and an average pore diameter of greater than 0.006 microns to provide an isolate elute stream comprising cannabidiol (CBD), non-polar solvent and other cannabinoids;

m) passing the isolate elute stream to a crystallization zone, wherein the isolate elute stream is subjected to a freezer temperature of equal to or less than about −20° C. for a freezer period of about 24 to about 72 hours to permit primary high purity cannabidiol crystals, containing from about 96 to about 98 wt. % cannabidiol to form, harvesting the primary high purity cannabidiol (CBD) crystals and admixing the primary high purity cannabidiol crystals with hexane to provide the crystal isolate solution comprising 20-30% by weight cannabidiol CBD oils, and retaining the crystal isolate solution at room temperature for a period of 24-72 hours to permit secondary high purity CBD crystals to form and harvesting the secondary high purity CBD crystals;

n) passing the secondary high purity CBD crystals to a rotary evaporation zone wherein the secondary high purity crystals are heated until molten to evaporate any residual non-polar and washed with a third water wash stream at least three times in the rotary evaporation, wherein at the completion of each wash step the secondary high purity crystals are dried to complete dryness to provide a solid CBD aggregate which is essentially free of tetrahydrocannabinol (THC) and has a cannabidiol purity of greater than 99 wt. %; and, o) withdrawing at least one high purity cannabidiol product being essentially free of tetrahydrocannabinol (THC) a stream selected from the group consisting of the high purity cannabinoid oil stream, the phytocannabinoid rich oil, the solid CBD aggregate and mixtures thereof.

In some aspects of the present disclosure, a purified product can be produced that comprises a Cannabidiol (CBD) concentration greater than about 98% (w/w) on an anhydrous basis.

BRIEF DESCRIPTION OF THE DRAWINGS

The accompanying drawings are included to provide a further understanding of the disclosure. The drawings illustrate embodiments of the disclosure and together with the description serve to explain the principles of the embodiments of the disclosure.

DETAILED DESCRIPTION OF EXEMPLARY EMBODIMENTS

Figure 1:
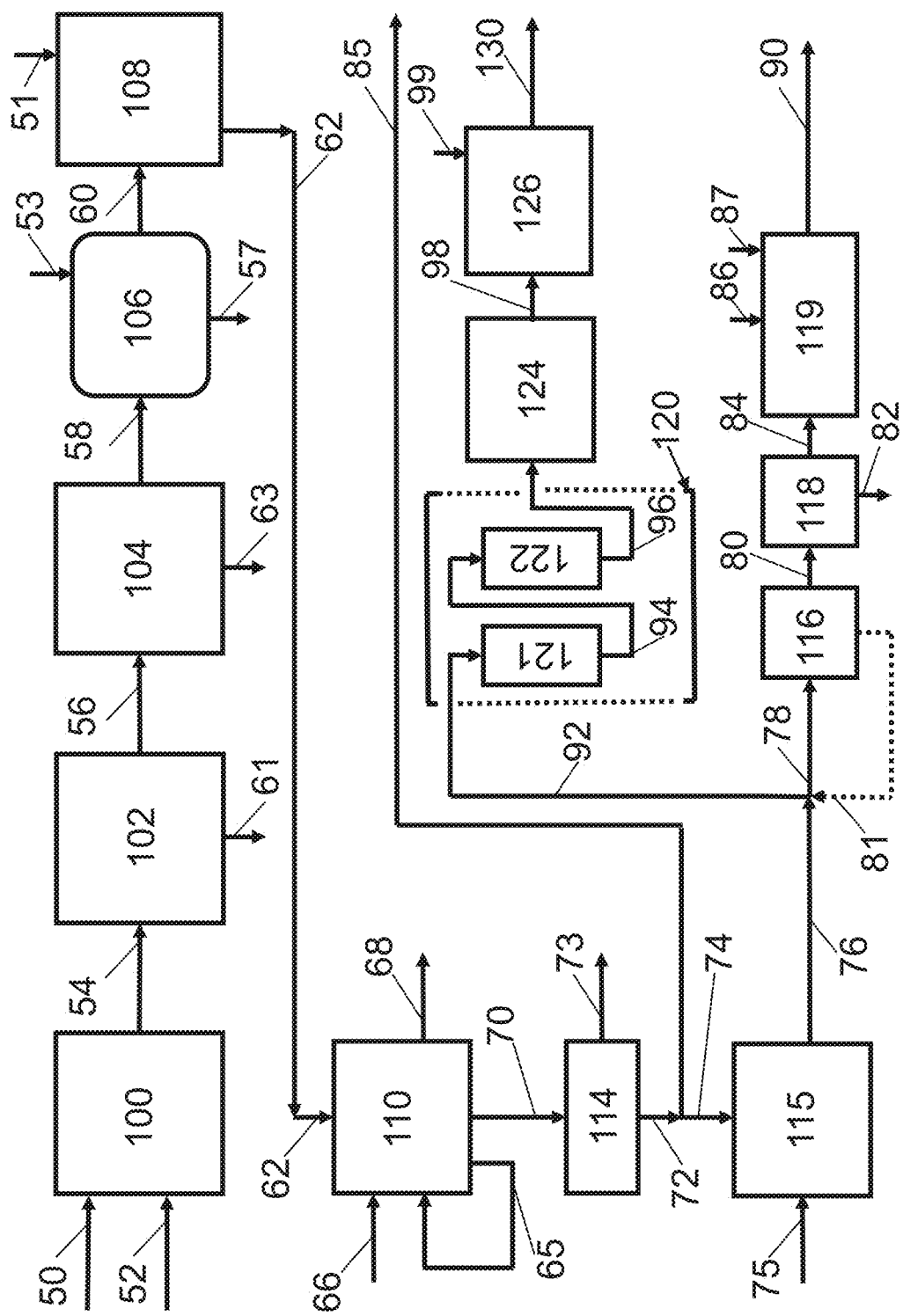
FIG. 1 is a schematic process flow diagram illustrating a configuration of the continuous overall process for recovery and purification of cannabidiol.

Industrial hemp, or agricultural hemp, and medical marijuana both come from the *Cannabis Sativa* L. plant. Industrial hemp, which is often referred to as "hemp stalk," grows differently than THC-containing *cannabis*, and looks similar to bamboo. Cannabinoids are a family of naturally occurring $C_{21}$ terpenophenolic compounds uniquely produced in *cannabis*. Marijuana usually refers to a mixture of leaves and flowering heads of the pistillate plant of *Cannabis sativa* from which tetrahydrocannabinols (THCs) are isolated. THCs contain two main isomeric forms, depending on the position of the double bond. The position of the double bond and the stereochemistry of these THCs have been confirmed by nuclear magnetic resonance and X-ray structure.

Extracting active ingredients from *cannabis* routinely extracts a number of impurities which are difficult to remove from the finished product; and, therefore a large number of purification steps, including expensive column chromatography, are required in conventional methods to isolate components.

The following are typical abbreviations for commonly found cannabinoids in the extract of hemp leaves:

| | |
|---|---|
| THC | Tetrahydrocannabinol |
| THCV | Tetrahydrocannabivarin |
| CBG | Cannabigerol |
| CBD | Cannabidiol |
| CBN | Cannabinol |
| THCA | Tetrahydrocannabinolic Acid |
| CBDA | Cannabidiolic Acid |
| CBDV | Cannabidivarin |

In various embodiments, the present disclosure relates to isolating and purifying cannabinoids from plants of the genus *Cannabis*, which contains three species, namely *Cannabis sativa, Cannabis indica*, and *Cannabis ruderalis*. The disclosure provides methods of extraction from the plant and purification using column chromatography. Any suitable cannabinoid can be isolated and purified. For example, the cannabinoid can be THC, THCV, THCA, CBG, CBD, CBN, CBDA, CBDV, or a combination thereof. The resulting extracted cannabinoid (e.g., CBD) can be purified to high levels, thereby allowing for their use in various pharmaceutical and nutraceutical applications. For example, in certain aspects purified CBD can be obtained, which has the benefits of CBD without the alternative effects of psychoactive THC.

Generally, the method comprises extracting, purifying, and isolating a cannabinoid (e.g., THC, THCV, THCA, CBG, CBD, CBN, CBDA, CBDV, or a combination thereof) using at least one chromatographic step (e.g., column chromatography). Any suitable adsorbent (e.g., OR-1, OR-2, OR-2 prime, OR-3, OR-4, OR-5, or a combination thereof) can be used for the chromatographic methods described herein. The adsorbent can be utilized in any suitable arrangement (e.g., single column chromatography, batch column chromatography, SMB chromatography, or a combination thereof). Typically, the method comprises using more than one adsorbent and more than one arrangement to achieve the desired purity of the cannabinoid.

In various aspects, the disclosure relates to methods for purification and separation of cannabinoids from dried hemp and *cannabis* leaves and purification of cannabinoids. The methods employ chromatographic resins and purification procedures for purifying and isolating a desired cannabinoid. In various embodiments, benefits of the methods of the disclosure include, but are not limited to, (i) increasing yield of a cannabinoid (e.g., CBD), (ii) increasing purity of a cannabinoid (e.g., CBD), (iii) allowing for a continuous process, and/or (iv) allowing for regeneration and reuse of chromatographic resins.

In some aspects of the disclosure, SMB chromatography can be used as a continuous process to obtain an increased purity of a cannabinoid (e.g., CBD). The process can utilize any of the unique chromatographic resins or purification protocols described herein.

In some aspects of the disclosure, column chromatography (e.g., SMB, batch, or single) can be utilized with any of the unique chromatographic resins (e.g., OR-1, OR-2, OR-2 prime, OR-3, OR-4, and/or OR-5) described herein to obtain an increased purity of a cannabinoid. For example, the chromatographic resins can be regenerated to obtain an increased yield of a cannabinoid, and allow for reuse of the chromatographic resins.

In additional aspects of the disclosure, batch column chromatography can be utilized to produce an increased yield of a cannabinoid an increase the longevity of a chromatographic resin. The process reuses a chromatographic resin in another stage of the purification process to obtain more of the cannabinoid and to increase the utility of the chromatographic resin.

The methods of the disclosure can be used to purify a constituent (e.g., a first or second constituent). As used herein, the terms "purify" and "purification" can refer to a process of separating at least a first constituent (e.g., a cannabinoid) from a second constituent (e.g., at least one impurity or a second cannabinoid) so as to provide a first composition wherein the first constituent is in a higher concentration relative to a second constituent and/or a second composition wherein the second constituent is in a higher concentration relative to the first constituent. To put it another way, the methods of the disclosure can be used to separate a cannabinoid and at least one impurity to produce a higher purity of the cannabinoid.

The processes described herein aim to separate a first constituent (e.g., a desired target cannabinoid) and a second constituent (e.g., at least one impurity and/or a second cannabinoid) from a feedstock stream (e.g., a crude *cannabis* extract stream). In some embodiments, the feedstock stream (e.g., a crude *cannabis* extract stream) comprises a desired target cannabinoid (e.g., CBD and/or CBDA) and at least one impurity (e.g., color bodies, acidic components, lipids, *cannabis* plant waxes, a second cannabinoid, or mixtures thereof) to be separated.

In some embodiments, the desired target cannabinoid is selected from Cannabidiol (CBD), Tetrahydrocannabinol (THC), Tetrahydrocannabivarin (THCV), Cannabigerol (CBG), Cannabinol (CBN), Tetrahydrocannabinolic Acid (THCA), Cannabidiolic Acid (CBDA), Cannabidivarin (CBDV), or mixtures thereof. In some embodiments, the desired target cannabinoid is selected from CBG, CBD, CBN, and CBDA. In certain embodiments, the desired target cannabinoid is CBD and/or CBDA. In preferred embodiments, the desired cannabinoid is CBD.

The at least one impurity can be considered any compound or mixture of compounds that are not the desired target cannabinoid. For example, the at least one impurity can include one or more of waxes, lipids, pigments, or mixtures thereof. In some embodiments, the at least one impurity can include other cannabinoids, e.g., a second cannabinoid, a third cannabinoid, etc., that are not the desired target cannabinoid.

In some embodiments, the second cannabinoid is selected from Cannabidiol (CBD), Tetrahydrocannabinol (THC), Tetrahydrocannabivarin (THCV), Cannabigerol (CBG), Cannabinol (CBN), Tetrahydrocannabinolic Acid (THCA), Cannabidiolic Acid (CBDA), Cannabidivarin (CBDV), or mixtures thereof. For example, the second cannabinoid can be in the form of Tetrahydrocannabinol (THC), cannabidiolic acid (CBDA), tetrahydrocannabinolic acid (THCA), cannabigerol (CBG), cannabinol (CBN), and combinations thereof. In some embodiments, the second cannabinoid is THC and/or THCA. In certain embodiments, the second cannabinoid is THC.

Thus, the desired cannabinoid and at least one impurity can each independently be selected from THC, THCV, CBG, CBD, CBN, THCA, CBDA, waxes, lipids, and pigments. In certain embodiments, the desired target cannabinoid is CBD and/or CBDA. For example, the desired target cannabinoid is CBD in some embodiments, while the second (impurity) cannabinoid is tetrahydrocannabinol (THC). In some embodiments, the desired target cannabinoid can be a cannabinoid other than CBD (e.g., THC), while the second cannabinoid is CBD.

The purity of a constituent (e.g., a cannabinoid) can be measured by any suitable means known to a person of ordinary skill in the art. In some embodiments, the purity of a constituent (e.g., a cannabinoid) is measured using high performance liquid chromatography (HPLC). In some embodiments, the purity of a constituent (e.g., a cannabinoid) is measured using weight percentage of the solid content. If the weight percentage of a constituent in the solid content increases, the constituent is considered to be more pure. If the weight percentage of a constituent in the solid content decreases, the constituent is considered to be less pure. To illustrate, a constituent having a weight percentage of 15% is more pure than if it had a weight percentage of 10%. Similarly, a constituent having a weight percentage of 90% is more pure than if it had a weight percentage of 75%.

As used herein, the term "solid concentration" refers to the mass of solids per volume of liquid in a given stream and is expressed as grams/Liter. The mass of the solids content in a stream is determined by subjecting a fixed volume of the sample, typically 1 ml, to an effective amount of heat, up to 80° C., at atmospheric pressure for a time sufficient to fully evaporate the sample to dryness, typically 1-2 hours.

Methods of the disclosure can use normal-phase chromatography and/or reversed-phase chromatography. In some embodiments, the methods of the disclosure employ a process known as reversed-phase chromatography. As used herein, the term "reversed-phase chromatography" employs a polar (aqueous) mobile phase. As a result, hydrophobic molecules in the polar mobile phase tend to adsorb to the hydrophobic stationary phase, and hydrophilic molecules in the mobile phase will pass through the column and are eluted first. Accordingly, any suitably stationary phase adsorbent (i.e., chromatographic resin) can be used in methods of the disclosure.

The stationary phase adsorbents may be disposed in a single adsorbent bed or may be disposed in a single column or series of single columns containing multiple adsorbent bed zones. Embodiments of the instant disclosure employ separate stationary phase adsorbents in carrying out the overall process of the disclosure. A list of exemplary stationary phases (i.e., chromatographic resins) for use in various embodiments of the methods of the disclosure are as follows.

OR-1 is a modified activated carbon adsorbent which was heat treated to provide a highly hydrophobic adsorbent which is essentially free of hydroxyl groups. In some embodiments, OR-1 has an average particle size range of from about 45 to about 1700 microns (e.g., about 50 to about 1000 microns, about 50 to about 500 microns, about 100 microns to about 500 microns, about 100 microns to about 250 microns, or 177 and 250 microns). In some embodiments, OR-1 has an iodine number (a measure of the micropore content of the activated carbon) greater than about 900 mg/g (e.g., greater than about 1000 mg/g, greater than about 1250 mg/g, greater than about 1500 mg/g, or greater than about 2000 mg/g).

OR-2 is a modified hydrophobic adsorbent comprising a styrene-divinylbenzene (DVB) resin or a poly(methyl methacrylate) (PMMA) resin. In some embodiments, the styrene-divinylbenzene (DVB) resin has from about 4 to about 8% (e.g., about 4%, about 4.5%, about 5%, about 5.5%, about 6%, about 6.5%, about 7%, about 7.5%, or about 8%) crosslinking. In some embodiments, OR-2 has an average particle size range of from about 25 microns to about 300 microns (e.g., about 25 microns to about 200 microns, about 25 microns to about 100 microns, about 100 microns to about 300 microns, about 200 microns to about 300 microns, or about 50 microns to about 250 microns). In some embodiments, OR-2 has an average bulk density of from about 0.4 g/mL to about 0.6 g/mL (e.g., about 0.4 g/mL, about 0.45 g/mL, about 0.5 g/mL, about 0.55 g/mL, or about 0.6 g/mL), an average surface area of from about 450 $m^2/g$ to about 550 $m^2/g$ (e.g., about 450 $m^2/g$ to about 525 $m^2/g$, about 450 $m^2/g$ to about 500 $m^2/g$, about 475 $m^2/g$ to about 550 $m^2/g$, or about 500 $m^2/g$ to about 550 $m^2/g$). In some embodiments, OR-2 has an average pore volume of from about 0.7 mL/g to about 0.9 mL/g (e.g., about 0.7 g/mL, about 0.75 g/mL, about 0.8 g/mL, about 0.85 g/mL, or about 0.9 g/mL). In certain embodiments of OR-2 resin, the modified hydrophobic adsorbent (i.e., hydrophobic resin) is a C18 resin.

OR-2 prime (i.e., OR-2') is a hydrophobic resin. In some embodiments, OR-2 prime has an average particle diameter of from about 25 microns to about 300 microns (e.g., about 25 microns to about 200 microns, about 25 microns to about 100 microns, about 100 microns to about 300 microns, about 200 microns to about 300 microns, or about 50 microns to about 250 microns). In some embodiments, OR-2 prime has an average bulk density of from about 0.75 g/mL to about 0.85 g/mL (e.g., about 0.75 g/mL, about 0.8, or about 0.85 g/mL). In some embodiments, OR-2 prime has an average surface area of from about 450 $m^2/g$ to about 500 $m^2/g$ (e.g., about 450 $m^2/g$ to about 490 $m^2/g$, about 450 $m^2/g$ to about 475 $m^2/g$, about 460 $m^2/g$ to about 500 $m^2/g$, or about 475 $m^2/g$ to about 500 $m^2/g$). In some embodiments, OR-2 prime has an average pore volume of from about 0.7 mL/g to about 0.9 mL/g (e.g., about 0.7 g/mL, about 0.75 g/mL, about 0.8 g/mL, about 0.85 g/mL, or about 0.9 g/mL). In certain embodiments of OR-2 prime resin, the modified hydrophobic adsorbent (i.e., hydrophobic resin) is a C18 resin.

OR-3 is a modified hydrophilic adsorbent comprising a spherical polar silica adsorbent having a high level of silanol (Si—O—H) groups. In some embodiments, OR-3 has an average particle diameter of from about 60 microns to about 200 microns (e.g., about 60 microns to about 150 microns, about 60 microns to about 100 microns, about 100 microns to about 200 microns, about 150 microns to about 200 microns, or about 100 microns to about 150 microns). In some embodiments, OR-3 has an average surface area of between 450 and 550 $m^2/g$ (e.g., about 450 $m^2/g$ to about 525 $m^2/g$, about 450 $m^2/g$ to about 500 $m^2/g$, about 475 $m^2/g$ to about 550 $m^2/g$, or about 500 $m^2/g$ to about 550 $m^2/g$), having an average pore volume of between 0.7 and 0.85 mL/g (e.g., about 0.7 g/mL, about 0.75 g/mL, about 0.8 g/mL, or about 0.85 g/mL). In some embodiments, OR-3 has an average pore size of between 50 to 75 Angstroms (i.e., 0.005-0.0075 microns).

OR-4 is an activated alumina adsorbent. In some embodiments, OR-4 has an average particle diameter of from about 50 to about 200 microns (e.g., about 50 microns to about 150 microns, about 50 microns to about 100 microns, about 100 microns to about 200 microns, about 150 microns to about 200 microns, or about 100 microns to about 150 microns). In some embodiments, OR-4 has an average bulk density of between 0.7 and 0.85 g/mL (e.g., about 0.7 g/mL, about 0.75 g/mL, about 0.8 g/mL, or about 0.85 g/mL). In some embodiments, OR-4 has an average surface area of between 140-170 $m^2/g$, and an average pore diameter of greater than 60 Angstroms (i.e., 0.006 microns).

OR-5 is a hydrophobic polystyrene-divinylbenzene adsorbent. In some embodiments, OR-5 has an average particle diameter of from about 250 microns to about 600 microns (e.g., about 250 microns to about 500 microns, about 250 microns to about 400 microns, about 250 microns to about 300 microns, about 300 microns to about 600 microns, about 400 microns to about 600 microns, about 500 microns to about 600 microns, or about 300 microns to about 500 microns). In some embodiments, OR-5 has an average bulk density of from about 0.6 g/mL to about 0.9 g/mL (e.g., about 0.6 g/mL, about 0.65 g/mL, about 0.7 g/mL, about 0.75 g/mL, about 0.8 g/mL, about 0.85 g/mL, or about 0.9 g/mL). In some embodiments, OR-5 has an average water content of from about 55% to about 65% (e.g., about 60%).

In some embodiments, the chromatographic resins described herein can be flushed with a solvent (e.g., ethanol) to recover the cannabinoid. In some embodiments, the chromatographic resins described herein can be regenerated for use in subsequent separation cycles. As used herein, "regeneration" can refer to the process of washing the resin with a regeneration solution to remove the at least one impurity and/or second cannabinoid. The chromatographic resins (e.g., OR-2, OR-2 prime, and/or OR-5) can be regenerated using any suitable regeneration solution. The regeneration solution of some embodiments comprises less than 5 wt. % water, and includes ethanol, acetone, or a combination thereof. In preferred embodiments, the regeneration solution comprises acetone.

The methods of the disclosure utilize a mobile phase desorbent ("mobile phase") to elute the first constituent (e.g., a cannabinoid) and/or second constituent (e.g., at least one impurity or a second cannabinoid) from the stationary phase. The mobile phase can be any suitable mobile phase capable of eluting a constituent. For example, the mobile phase can comprise water, ethanol, acetone, ethyl acetate, acetonitrile, pentanes, hexanes, heptanes, methanol, propanol, or a combination thereof. In some embodiments, a mobile phase desorbent for use in the methods described herein (e.g., SMB and batch chromatography) is a mixture of ethanol (e.g., food grade ethanol) and water (e.g., deionized water), or in other words, an ethanolic mixture. As used herein, the term "ethanolic" can mean comprising ethanol. The mobile phase desorbent employs a ratio of ethanol to water of from about 50 parts ethanol (Food grade ethanol −200 Proof) to about 50 parts water to about 90 parts ethanol to about 10 parts water (i.e., a ratio of ethanol to water of about 50:50, about 55:45, about 60:40, about 65:35, about 70:30, about 75:25, about 80:20, about 85:15, or about 90:10). In some embodiments, the mobile phase desorbent employs a ratio of ethanol to water of from about 50 parts ethanol to about 50 parts water to about 80 parts ethanol to about 20 parts water. In certain embodiments, the ratio of ethanol to water in the mobile phase is about 80 parts ethanol to about 20 parts water.

The methods of the disclosure utilize a feedstock stream (i.e., feed). The feedstock stream can be prepared by any suitable method such that it contains at least one constituent (e.g., cannabinoid) to be separated (i.e., purified). In some embodiments a procedure of feed preparation is as follows. Following harvesting and processing, the grinded and dried *cannabis* leaves are extracted with an appropriate GRAS solvent, preferably ethanol, or mixtures of ethanol and water. A number of different parameters can influence the overall yield, quality and/or purity of the desired final product. These parameters include, but are not limited to, the identity of the chosen GRAS solvent; the temperature and time at which the chosen natural solvent is used; the ratio of raw material to solvent (raw material:solvent (v/v)) that is employed; the number of successive extractions performed; the chosen method of purification of the desired products and the conditions related thereto. The skilled person will understand that these parameters are not necessarily mutually exclusive, and that a particular choice relating to one parameter may or may not affect the choice of other parameters. For example, the identity of the chosen natural solvent, and the temperature thereof, can affect the optimal ratio of raw material to solvent that is required to obtain the desired results. Following the extraction of the cannabinoids from the *cannabis* leaves, a crude extract stream comprising crude cannabinoids and impurities is provided in the extraction zone. The crude cannabinoid stream is filtered to remove debris and small particles in a progressive filtration step to provide a filtered crude cannabinoid stream.

In some embodiments, the crude cannabinoids are admixed with ethanol to provide a filtered crude cannabinoid stream which comprises from about 3 wt. % to about 4 wt. % (e.g., about 3.2 wt. % to about 3.8 wt. %, about 3.4 wt. % to about 4 wt. %, about 3.2 wt. % to about 3.7 wt. % or about 3.4 wt. % to about 3.7 wt. %) total crude cannabinoids in the mixture. Preferably, the filtered crude cannabinoid stream comprises from about 3.4 wt. % to about 3.7 wt. % total cannabinoids in the mixture. The concentration of solids in the filtered crude cannabinoid stream varies from about 60 g/L to about 80 g/L (e.g., about 60 g/L, about 65 g/L, about 70 g/L, about 75 g/L, or about 80 g/L), and is preferably about 75 g/L.

In certain embodiments, the feedstock stream is hemp extract. As used herein, the phrase "hemp extract" can refer to feed prepared by using ethanol solvent to extract the desired compounds from industrial hemp leaves. In some embodiments, the hemp extract is further mixed with water to form an ethanol/water mixture. The resulting ethanol/water mixture comprising hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

In certain embodiments, the feedstock stream is decolorized hemp extract. As used herein, the phrase "decolorized hemp extract" can refer to feed prepared by using ethanol solvent to extract the desired compounds from industrial hemp leaves. The resulting extract is then processed through a chromatographic resin (e.g., OR-1) to decolorize (i.e., remove chlorophylls & pigments). In some embodiments, the decolorized hemp extract is further mixed with water to form an ethanol/water mixture. The resulting ethanol/water mixture comprising decolorized hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

In certain embodiments, the feedstock stream is decolorized and decarboxylated hemp extract. As used herein, the phrase "decolorized and decarboxylated hemp extract" can refer to feed that is prepared by using ethanol solvent to extract the desired compounds from industrial hemp leaves. The resulting extract is then processed through a chromatographic resin (e.g., OR-1) to decolorize (i.e., remove chlorophylls & pigments). The decolorized hemp extract is then placed in a still to apply heat to activate/convert the acidic form to a decarboxylated form. In some embodiments, the decolorized and decarboxylated hemp extract is further mixed with water to form an ethanol/water mixture. The resulting ethanol/water mixture comprising decolorized and decarboxylated hemp extract can have an ethanol to water ratio of about 100:0, e.g., about 90:10, about 80:20, about 70:30, about 60:40, or about 50:50 or less. In preferred embodiments, the ethanol to water ratio is from about 50:50 to about 80:20.

In some embodiments, the method comprises purifying a cannabinoid with simulated moving bed (SMB) chromatography (e.g., a continuous process for purification of cannabinoids extracted from the dried hemp and *cannabis* leaves). In some embodiments, the method relates to a continuous process for the purification of cannabinoids, specifically cannabidiol and tetrahydrocannabinol using a sequence of purification steps and a continuous simulated moving bed process and downstream recovery steps to separate cannabinoids from tetrahydrocannabinol and to provide phytocannabinoid rich oil and cannabidiol isolate products.

Applicant discovered a process for purifying the crude extract of the *Cannabis* plant, which can include steps relating to one or more of a filtration zone, a decolorization zone, an activation zone, a dewaxing zone, a simulated moving bed zone, a second filtration zone, a purification zone, a concentration zone, and a crystallization zone. Preferred embodiments provide a scheme wherein no toxic solvents are required to provide a high purity Cannabidiol (CBD) product which is essentially free of tetrahydrocannabinol.

In some embodiments, a simulated moving bed (SMB) system is arranged for maximum selectivity. The simulated moving bed operation is achieved by use of a plurality of adsorbent beds connected in series or portions in series or parallel and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process in some embodiments. Feed and mobile phase desorbent enter, while extract and raffinate streams are withdrawn continuously at substantially constant compositions. The overall operation is similar in performance to an operation wherein the fluid and solid are contacted in a continuous countercurrent manner, without the actual movement of the solid, or stationary phase adsorbent.

The SMB system may be operated such that the adsorbent beds are operated individually or in parallel using a single rotary valve and associated control system. A column may comprise one or more beds containing chromatographic media. Associated feed tanks, filters, piping connecting flow between columns and/or beds where so connected, pumps, valving, pressure regulators, metering equipment, flow control and microprocessor equipment utilized in the embodiment are well known in construction and function to those of ordinary skill in the art.

Benefits of the continuous simulated moving bed process described herein can include increased product yield, increased product purity, and reduced purification times. In addition, the continuous process may utilize chromatographic resins and mobile phases (solvents) for multiple purification runs, thereby reducing the overall cost of purification.

In embodiments, the disclosure provides a method of separating a cannabinoid (e.g., CBD and/or CBDA) from a *cannabis* plant, the *cannabis* plant including the cannabinoid and at least one impurity, the method comprising: combining the *cannabis* plant and a solvent to form a crude *cannabis* extract stream; processing the crude *cannabis* extract stream into a simulated moving bed (SMB) feedstock stream by removing at least a portion of at least one impurity in the crude *cannabis* extract stream; and passing the SMB feedstock stream through a SMB zone to provide a primary raffinate stream having a higher purity of the cannabinoid than in the SMB feedstock stream as measured by weight percentage of the solid content and a SMB extract stream having a lower purity of the cannabinoid than in the SMB feedstock stream as measured by weight percentage of the solid content.

For example, in some embodiments, the method comprises combining the *cannabis* plant and a solvent to form a crude *cannabis* extract stream including a desired target cannabinoid (e.g., CBD and/or CBDA) and at least one impurity (e.g., color bodies, acidic components, lipids, *cannabis* plant waxes, or mixtures thereof). The *cannabis* plant can be any suitable *cannabis* plant. The *cannabis* plant can be, for example *Cannabis sativa, Cannabis indica, Cannabis rudralis*, or a mixture thereof. In some embodiments, the *cannabis* plant can be in the form of dried hemp, *cannabis* leaves, or a mixture thereof, which can be used to form a crude *cannabis* extract stream including the desired target cannabinoid (e.g., CBD and/or CBDA) and at least one impurity (e.g., color bodies, acidic components, lipids, *cannabis* plant waxes, or mixtures thereof).

Any suitable solvent can be used for the crude *cannabis* extract stream, particularly for a stream containing one or more of THC, THCV, CBG, CBD, CBN, THCA, and CBDA. In some embodiments, the solvent includes water, ethanol, acetone, ethyl acetate, acetonitrile, pentanes, hexanes, heptanes, methanol, propanol, or a combination thereof. In some embodiments, the solvent comprises ethanol.

In some embodiments, the method comprises processing the crude *cannabis* extract stream to provide a simulated moving bed (SMB) feedstock stream. As used herein, the phrase "processing the crude *cannabis* extract stream" can refer to a method including at least one of decolorizing the crude *cannabis* extract stream to remove at least a portion of the color bodies from the crude *cannabis* extract stream, activating the crude *cannabis* extract stream to remove at least a portion of the acidic components from the crude *cannabis* extract stream, and dewaxing the crude *cannabis* extract stream to remove at least a portion of the lipids and *cannabis* plant waxes from the crude *cannabis* extract stream.

In some embodiments, the crude *cannabis* extract stream is decolorized to remove at least a portion of the color bodies (i.e., pigments) from the crude *cannabis* extract stream. As used herein, the phrase "color bodies" can refer to the colored pigments of the *cannabis* plant (e.g., chlorophyll). The crude *cannabis* extract stream can be decolorized by any suitable method. For examples, the crude *cannabis* extract stream can be decolorized by column chromatography and or extraction.

In some embodiments, the crude *cannabis* extract stream is activated to remove at least a portion of the acidic components from the crude *cannabis* extract stream. The acid components can be removed by any suitable method. For example, the acid components are removed from the crude *cannabis* extract stream by column chromatography, extraction, and/or decarboxylation.

In some embodiments, the crude *cannabis* extract stream is dewaxed to remove at least a portion of lipids and *cannabis* plant waxes from the crude *cannabis* extract stream. The crude *cannabis* extract stream can be dewaxed by any suitable method. For example, the crude *cannabis* extract stream can be dewaxed using column chromatography or extraction.

In some embodiments, processing the crude *cannabis* extract stream into the SMB feedstock stream includes passing the crude *cannabis* extract stream through a first chromatographic resin, and passing the SMB feedstock stream through the SMB zone includes passing the SMB feedstock stream through a second chromatographic resin, the second chromatographic resin being different from the first chromatographic resin.

In some embodiments, the method comprises passing the SMB feedstock stream through a SMB zone to provide a primary raffinate stream. The SMB zone comprises a plurality of adsorbent beds (e.g., columns comprising a stationary phase). The SMB zone can comprises any suitable number of adsorbent beds. For example, the SMB zone can comprise 2 or more adsorbent bed, e.g., 3 or more adsorbent beds, 4 or more adsorbent beds, 5 or more adsorbent beds, 6 or more adsorbent beds, 10 or more adsorbent beds, or 20 or more adsorbent beds. In some embodiments, the plurality of adsorbent beds are arranged in serial fluid communication such that fluid introduced at a top of any adsorbent bed (n) passes to the next highest adsorbent bed (n+1). In such embodiments, the method can further comprise advancing each adsorbent bed, such that adsorbent bed n+1 becomes adsorbent bed n after advancing, and adsorbent bed n prior to advancing becomes adsorbent bed n+x after advancing, wherein adsorbent bed n+x is the highest adsorbent bed in the serial fluid communication arrangement.

Figure 9:
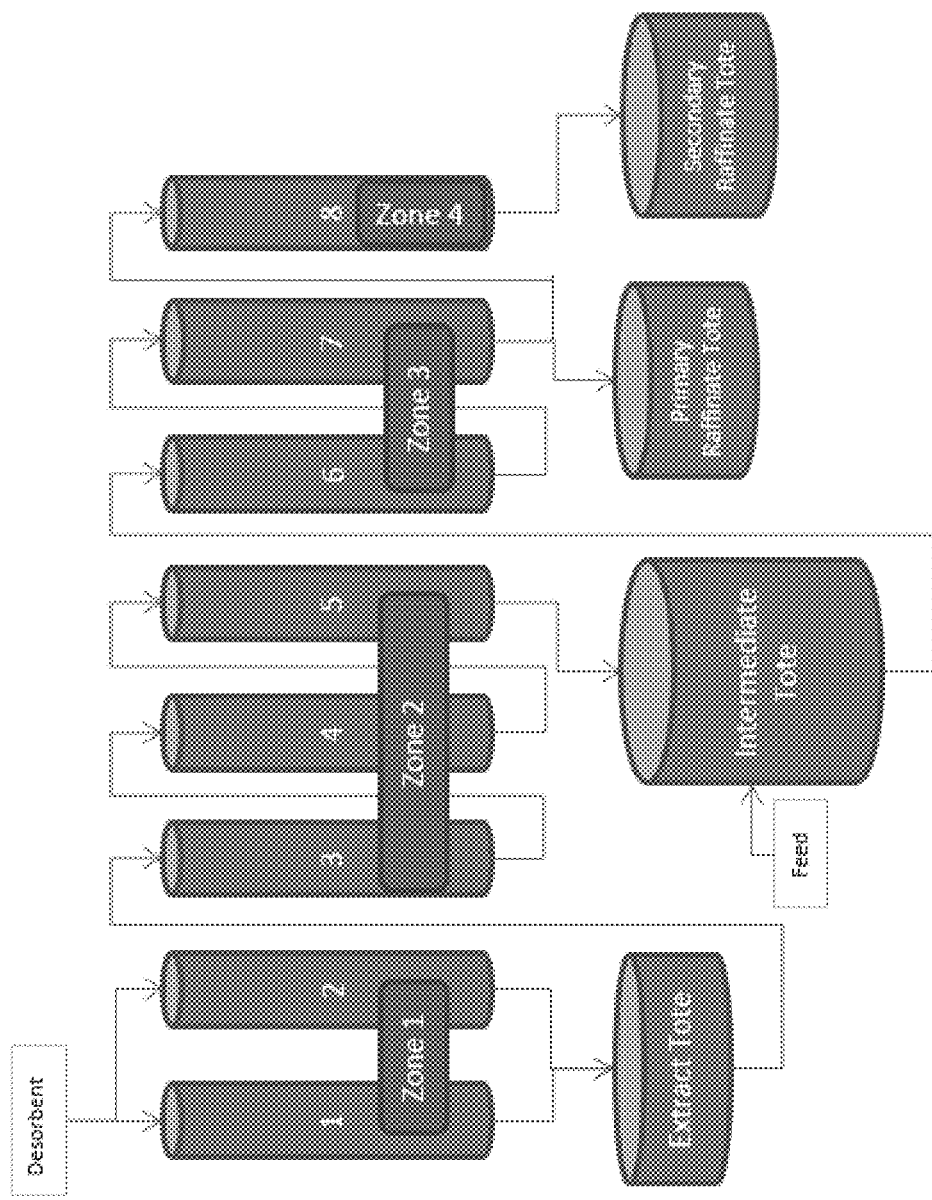
FIG. 9 is a schematic diagram depicting an SMB zone in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a concentration zone, respectively.

In some embodiments, the SMB zone comprises eight adsorbent beds. The eight adsorbent beds can be broken down into four zones referring to a desorption zone, a rectification zone, an adsorption zone, and a concentration zone. The adsorbent beds can be in any suitable arrangement (e.g., 2-2-2-2, 3-2-2-1, 2-3-2-1, 2-2-3-1, 1-3-3-1, 3-3-1-1, 3-1-3-1, or 2-2-3-1, etc.), wherein each number refers to one of the four zones. In certain embodiments, the SMB zone is in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a concentration zone, respectively. Such an arrangement is depicted in FIG. 9.

The adsorbent beds can comprise the same stationary phase or different stationary phases. In preferred embodiments, the adsorbent beds comprise the same stationary phase. For example, the adsorbent beds can comprise OR-1, OR-2, OR-2 prime, OR-3, OR-4, and/or OR-5.

In various embodiments, the SMB zone comprises a plurality of adsorbent beds, each bed containing OR-1; OR-2; OR-2 prime; or OR-5.

In some embodiments, the SMB zone comprises a plurality of adsorbent beds, each bed containing a modified hydrophobic adsorbent comprising a poly(methyl methacrylate) (PMMA) resin or a styrene-divinylbenzene (DVB) resin having about 4% to about 8% crosslinking.

In some embodiments, the method comprises passing the SMB feedstock stream through a SMB zone to provide a primary raffinate stream. Typically, the primary raffinate stream has a higher purity of the cannabinoid than in the SMB feedstock stream as measured by weight percentage of the solid content. In some embodiments, the primary raffinate stream has a higher purity of CBD than in the SMB feedstock stream as measured by weight percentage of the solid content. In certain embodiments, the primary raffinate stream is essentially free of THC.

The average mass recovery of the cannabinoid (e.g., CBD) by the primary raffinate stream can be any suitable amount. As used herein, the phrase "average mass recovery" refers to the percent yield of the cannabinoid. In some embodiments, the average mass recovery of the cannabinoid (e.g., CBD) in the primary raffinate stream is about 50 wt. % or more (e.g., about 60 wt. % or more, about 70 wt. % or more, about 80 wt. % or more, about 90 wt. % or more, or about 95 wt. % or more) based on the amount of the cannabinoid in the simulated moving bed (SMB) feedstock stream. In certain embodiments, the average mass recovery of CBD in the primary raffinate stream is about 80 wt. % or more based on the amount of CBD constituent in the simulated moving bed (SMB) feedstock stream.

The purity of the cannabinoid (e.g., CBD) in the primary raffinate stream can be any suitable amount. The purity is a measure of how much of a constituent of interest is present relative to all other constituents. Accordingly, the purity can be any amount from 0% to 100%, wherein 0% is the least pure and 100% is the most pure. In some embodiments, the purity of the cannabinoid (e.g., CBD) in the primary raffinate stream is about 25% to about 100% based on all other components, as determined by HPLC or as measured by weight percentage of the solid content. For example, the purity of the cannabinoid (e.g., CBD) in the primary raffinate stream can be about 25% to about 90% (e.g., about 25% to about 80%, about 25% to about 70%, about 25% to about 60%, or about 25% to about 50%) based on all other components, as determined by HPLC or as measured by weight percentage of the solid content. In certain embodiments, the purity of the cannabinoid (e.g., CBD) in the primary raffinate stream is about 35% to about 50% based on all other components, as determined by HPLC or as measured by the weight percentage of solid content.

In some embodiments, the method comprises passing the SMB feedstock stream through a SMB zone to provide a SMB extract stream. Typically, the SMB extract stream has a lower purity of the cannabinoid than in the SMB feedstock stream as measured by weight percentage of the solid content. In some embodiments, the SMB extract stream has a lower purity of CBD than in the SMB feedstock stream as measured by weight percentage of the solid content. In certain embodiments, the SMB extract stream is essentially free of CBD.

The average mass recovery of the second cannabinoid (e.g., THC) by the SMB extract stream can be any suitable amount. In some embodiments, the average mass recovery of the second cannabinoid (e.g., THC) in the SMB extract stream is about 50 wt. % or more (e.g., about 60 wt. % or more, about 70 wt. % or more, about 80 wt. % or more, about 90 wt. % or more, or about 95 wt. % or more) based on the amount of the second cannabinoid in the simulated moving bed (SMB) feedstock stream. In certain embodiments, the average mass recovery of THC in the SMB extract stream is about 80 wt. % or more based on the amount of THC in the simulated moving bed (SMB) feedstock stream.

The purity of the second cannabinoid (e.g., THC) in the SMB extract stream can be any suitable amount. In some embodiments, the purity of the second cannabinoid (e.g., THC) in the SMB extract stream is about 25% to about 100% based on all other components, as determined by HPLC or as measured by weight percentage of the solid content. For example, the purity of the second cannabinoid (e.g., THC) in the SMB extract stream can be about 25% to about 90% (e.g., about 25% to about 80%, about 25% to about 70%, about 25% to about 60%, or about 25% to about 50%) based on all other components, as determined by HPLC or as measured by weight percentage of the solid content. In certain embodiments, the purity of the second cannabinoid (e.g., THC) in the SMB extract stream is about 35% to about 50% based on all other components, as determined by HPLC or as measured by weight percentage of the solid content.

In some embodiments, the method further comprises removing the primary raffinate stream to provide a cannabinoid oil stream. The primary raffinate stream can be removed by any suitable method. For example, the primary raffinate stream can be removed by evaporation (e.g., under reduced pressure, elevated temperature, or a combination thereof), membrane permeation (e.g., nano-filtration), or a combination thereof.

The method can further comprise polishing at least a portion of the cannabinoid oil stream, wherein the polishing comprises mixing the cannabinoid oil stream with a non-polar solvent (e.g., pentanes, hexanes, or heptanes) to provide a polishing zone feed stream, agitating the polishing zone feed stream for a first period of time, allowing the agitated polishing zone feed stream to settle for a second period of time, and filtering (e.g., collecting) the settled polishing zone feed stream to provide a filtered non-polar solution having a higher purity of the cannabinoid than in the cannabinoid oil stream as measured by weight percentage of the solids content.

In some embodiments, the method further comprises removing the filtered non-polar solution to provide an evaporated cannabinoid oil stream. The filtered non-polar solution can be removed by any suitable method. For example, the filtered non-polar solution can be removed by evaporation (e.g., under reduced pressure, elevated temperature, or a combination thereof), membrane permeation (e.g., nano-filtration), or a combination thereof.

The method can further comprise washing the evaporated cannabinoid oil stream with a wash solvent to provide a washed cannabinoid oil stream. The evaporated cannabinoid oil stream can be washed any suitable number of times. For example, the evaporated cannabinoid oil can be washed one or more times, two or more times, three or more times, or four or more times. In certain embodiments, the evaporated cannabinoid oil stream is washed more than once.

The wash solvent can be any suitable solvent (e.g., water, ethanol, acetone, ethyl acetate, acetonitrile, pentanes, hexanes, heptanes, methanol, propanol, or a combination thereof). In certain embodiments, the wash solvent comprises methanol, water, or mixtures thereof.

In some embodiments, the method further comprises drying the washed cannabinoid oil stream. The washed cannabinoid oil stream can be dried by any suitable method. For example, the washed cannabinoid can be dried with a desiccant, under reduced pressure, at an elevated temperature, or any combination thereof.

Typically, the washed cannabinoid oils stream is free of at least one of THC, THCV, THCA, waxes, lipids, and pigments. In some embodiments, the washed cannabinoid oil stream is free of THC and or THCA. In certain embodiments, the washed cannabinoid oil stream is THC free.

In some embodiments, at least a portion of the filtered non-polar solution is passed through an isolate chromatography zone comprising a first chromatography column and a second chromatography column to provide an isolate elute stream having a higher purity of the cannabinoid than in the filtered non-polar solution as measured by weight percentage of the solid content, wherein the first and second columns are connected in serial fluid communication.

The first chromatography column can comprise any suitable chromatographic resin. In some embodiments, the first chromatography column comprises OR-3 and/or OR-4. In certain embodiments, the first chromatography column comprises OR-3 (i.e., a hydrophilic resin comprising a spherical polar silica adsorbent having Si—OH groups, having an average particle diameter between about 60 and about 200 microns, having an average surface area between about 450 and about 550 m2/g, having an average pore volume of between about 0.7 and about 0.85 mL/g, and having a pore size between about 0.005 and about 0.0075 microns).

The second chromatography column comprises any suitable chromatographic resin. In some embodiments, the second chromatography column comprises OR-3 and/or OR-4. In certain embodiments, the second chromatography column comprises OR-4 (i.e., an activated alumina adsorbent having an average particle diameter between about 50 and about 200 microns, an average bulk density of about 0.85 g/mL, an average surface area between about 140 and about 170 $m^2/g$, and an average pore diameter greater than about 0.006 microns).

The method of some embodiments further comprises cooling the isolate stream to form a crystallized cannabinoid. The cannabinoid can be crystallized by any suitable method and to any suitable purity. In some embodiments, the method comprises cooling the isolate elute stream for a cooling period of time, to thereafter provide crystallized cannabidiol. The crystallized cannabidiol can have a purity of from about 90 wt. % to about 100 wt. % (e.g., about 92 wt. % to about 99 wt. %, about 95 wt. % to about 99 wt. %, or about 96 wt. % to about 98 wt. %) as determined by HPLC. In certain embodiments, the crystallized cannabidiol has a purity of from about 96 wt. % to about 98 wt. % as determined by HPLC.

In some embodiments, the method further comprises recrystallizing the crystallized cannabidiol. The crystallized cannabidiol can be recrystallized by any suitable method and to any suitable purity. For example, the recrystallized cannabidiol can have a purity of from about 95 wt. % to about 100 wt. % (e.g., about 96 wt. % to about 100 wt. %, about 97 wt. % to about 100 wt. %, about 98 wt. % to about 100 wt. %, or about 99 wt. % to about 100 wt. %). In certain embodiments, the recrystallized cannabidiol has a purity of greater than about 99 wt. % as determined by HPLC.

In some embodiments, the method comprises purification of cannabinoids extracted from dried hemp and *cannabis* leaves using single column chromatography, batch chromatography, and/or SMB chromatography. In some embodiments, the method employs passing a feedstock stream from a *cannabis* plant comprising at least one cannabinoid of interest and at least one impurity through a chromatographic resin selected from OR-1, OR-2, OR-2 prime, OR-3, OR-4, and/or OR-5.

The method comprises passing a feedstock stream from a *cannabis* plant containing at least one desired target cannabinoid of interest and at least one impurity through a chromatographic resin. Preferred embodiments provide chromatographic resins and protocols that provide a high purity Cannabidiol (CBD) product which is essentially free of tetrahydrocannabinol.

In some embodiments, the method comprises preparing a feedstock stream comprising the *cannabis* plant and a solvent; passing the feedstock stream through a chromatographic resin to provide an eluate stream having a higher purity of the cannabinoid than in the feedstock stream as measured by weight percentage of the solid content, the chromatographic resin comprising one or more of the following: a first resin comprising a modified activated carbon adsorbent having an average particle size range of from about 45 to about 1700 microns; a second resin comprising a modified hydrophobic adsorbent comprising a styrene-divinylbenzene (DVB) resin or a poly(methyl methacrylate) (PMMA) resin having an average bulk density of from about 0.4 g/mL to about 0.6 g/mL; a third resin comprising a hydrophobic resin having an average bulk density of from about 0.75 g/mL to about 0.85 g/mL; a fourth resin comprising a hydrophobic polystyrene-divinylbenzene adsorbent having a water content of from about 55% to about 65%; or a mixture thereof.

The feedstock stream comprises any suitable extract from any suitable *cannabis* plant material, and can be prepared by any suitable method described herein. In some embodiments, the feedstock stream comprises a hemp extract, a decolorized hemp extract, a decolorized and decarboxylated hemp extract, or any combination thereof. The feedstock stream of some embodiments further comprises any suitable solvent described herein (e.g., water, ethanol, acetone, ethyl acetate, acetonitrile, pentanes, hexanes, heptanes, methanol, propanol, or a combination thereof). Typically, the feedstock stream comprises ethanol. An exemplary list of suitable feedstock streams is as follows.

The method comprises passing a feedstock stream from a *cannabis* plant comprising the cannabinoid and at least one impurity through a chromatographic resin. The chromatographic resin can be any suitable chromatographic resin selected from OR-1, OR-2, OR-2 prime, OR'5, and any combination thereof. In certain embodiments, the chromatographic resin is OR-1 resin. In certain embodiments, the chromatographic resin is OR-2 resin. In certain embodiments, the chromatographic resin is OR-2 prime resin. In embodiments where the chromatographic resin is OR-2 prime resin, the resin can be a C18 resin. In certain embodiments, the chromatographic resin is OR-5 resin. In certain embodiments, the chromatographic resin is (i) a combination of OR-1 and OR-2 prime, (ii) a combination of OR-1 and OR-5, (iii) a combination of OR-2 prime and OR-5, or (iv) a combination of OR-1, OR-2 prime, and OR-5.

Typically, the chromatographic resin is contained in a container (e.g., a column). The container can be any suitable container. Generally the container is a column. The chromatographic resin can be in a single column, or in more than one column (e.g., two or more columns, three or more columns, four or more columns, five or more columns, six or more columns, seven or more columns, eight or more columns, nine or more columns, or ten or more columns). In some embodiments, the chromatographic resin is in a single column. In some embodiments, the chromatographic resin is in more than one column.

In some embodiments where the chromatographic resin is in more than one column, at least a portion of the more than one column can be arranged in an SMB configuration. Accordingly, the feedstock stream can be purified and/or processed and purified by an SMB chromatographic method described herein.

In other embodiments where the chromatographic resin is in more than one column, the chromatographic resin can be (i) a combination of OR-1 and OR-2 prime, (ii) a combination of OR-1 and OR-5, (iii) a combination of OR-2 prime and OR-5, or (iv) a combination of OR-1, OR-2 prime, and OR-5, wherein each of OR-1 resin, OR-2 prime resin, and OR-5 resin is in one or more separate columns.

In another aspect of the disclosure, a method is provided for the purification of a composition containing at least a first constituent (e.g., a desired target cannabinoid, such as for example, CBD) and a second constituent (e.g., at least one impurity and/or a second cannabinoid). The method comprises passing the composition through at least three chromatographic resins.

In some embodiments, the method comprises purifying a composition containing at least a first constituent (e.g., a desired target cannabinoid, such as for example, CBD) and a second constituent (e.g., at least one impurity and/or a second cannabinoid), the method comprising: passing a first feedstock stream through a first chromatographic resin to form a first eluate having a higher ratio of the first constituent to the second constituent than in the first feedstock stream; passing the first eluate through a second chromatographic resin to form a second eluate having a higher ratio of the first constituent to the second constituent than in the first eluate; passing a second feedstock stream through the second chromatographic resin to form a third eluate having a higher ratio of the first constituent to the second constituent than in the second feedstock stream; and passing the third eluate through a third chromatographic resin to form a fourth eluate having a higher ratio of the first constituent to the second constituent than in the third eluate.

The first constituent (e.g., a desired target cannabinoid, such as for example, CBD) and/or second constituent (e.g., at least one impurity and/or a second cannabinoid) can be recovered at any suitable moment (e.g., from the first eluate, from the second eluate, from the third eluate, from the fourth eluate, or a combination thereof). In some embodiments, the first constituent (e.g., a desired target cannabinoid, such as for example, CBD) is recovered from the second eluate and/or the fourth eluate. In certain embodiment, the first constituent is recovered from the second eluate and the fourth eluate.

In some embodiments, at least a portion of the first constituent (e.g., the desired target cannabinoid) from the first eluate adsorbs to the second chromatographic column. Without wishing to be bound by any particular theory, it is believed that an added benefit of the method, deemed "batch chromatography," described herein is that once a chromatographic resin is saturated with the second constituent (e.g., THC), the column can still be used to remove waxes, lipids, and/or pigments. In addition, any portion of the first constituent (e.g., CBD) adsorbed to the second chromatographic column may be recovered by passing a second feedstock stream through the second chromatographic resin to elute at least a portion of the adsorbed first constituent in the third eluate. Accordingly, the method can increase the longevity of a chromatographic resin, and increase the yield of the first constituent (e.g., CBD).

In some embodiments, the method increases the isolated yield of the first constituent (e.g., CBD) by at least about 15% (e.g., at least about 20%, at least about 25%, at least about 30%, at least about 35%, or at least about 40%) relative to a conventional method that does not pass a second feedstock stream through a used resin from a prior cycle with the first feedstock stream.

In some embodiments, the batch purification method comprises passing a first feedstock stream comprising a desired target cannabinoid (e.g., CBD) through two or more columns, wherein one of the columns is reused for a second feedstock stream and the result is an increase in yield of the cannabinoid (e.g., CBD). In this regard, the second feedstock stream and one or more further cycles will preferably produce a higher yield than the yield from the first cycle with the first feedstock stream.

In an illustrative embodiment, the method comprises: passing a first feedstock stream through a first chromatographic resin to form a first eluate having a higher ratio of CBD to THC than in the first feedstock stream; passing the first eluate through a second chromatographic resin to form a second eluate having a higher ratio of CBD to THC than in the first eluate; passing a second feedstock stream through the second chromatographic resin to form a third eluate having a higher ratio of CBD to THC than in the second feedstock stream; and passing the third eluate through a third chromatographic resin to form a fourth eluate having a higher ratio of CBD to THC than in the third eluate.

In another illustrative embodiment, the method comprises passing a first feedstock stream through a first chromatographic resin to form a first eluate having a higher purity of CBD than in the first feedstock stream. The first eluate is passed through a second chromatographic resin to form a second eluate having a higher purity of CBD than in the first eluate. For example, in some embodiments, the first and second resin can be for decoloring and/or dewaxing, as discussed herein, in either order. The second eluate can be passed through a third chromatographic resin to form a third eluate with a higher purity of CBD than in the second eluate (e.g., a higher ratio of CBD to THC). A second feedstock stream can then be passed through the second or third chromatographic resin (which is thusly reused) to form a fourth eluate having a higher purity of CBD than in the second feedstock stream. The fourth eluate can optionally be passed through a fourth chromatographic resin to form a fifth eluate having a higher purity of CBD than in the fourth eluate. In this regard, for example, the third chromatographic resin can be for polishing the first feedstock stream as discussed herein to enhance the CBD purity, and can be used for decoloring and/or dewaxing the second feedstock stream.

Typically, the first chromatographic resin and the second chromatographic resin are in a first serial fluid communication arrangement. The first serial fluid communication arrangement can have the first chromatographic resin and the second chromatographic resin only, or the first serial fluid communication arrangement can further comprise one or more additional chromatographic resins. The one or more additional chromatographic resins can be placed in any location in the first serial fluid communication arrangement. In some embodiments, the first chromatographic resin and the second chromatographic resin are interrupted by at least one of the one or more additional chromatographic resins. As used herein, the term "interrupted" can mean that there is one or more additional chromatographic resins between two chromatographic resins. In some embodiments, the first chromatographic resin and the second chromatographic resin are not interrupted by an additional chromatographic resin. Thus, the one or more additional chromatographic resins are not present or the one or more addition resins are added before the first chromatographic resin and/or after the second chromatographic resin.

Typically, the second chromatographic resin and the third chromatographic resin are in a second serial fluid communication arrangement. The second serial fluid communication arrangement can have the second chromatographic resin and the third chromatographic resin only, or the second serial fluid communication arrangement can further comprise one or more additional chromatographic resins. The one or more additional chromatographic resins can be placed in any location in the second serial fluid communication arrangement. In some embodiments, the second chromatographic resin and the third chromatographic resin are interrupted by at least one of the one or more additional chromatographic resins. In some embodiments, the second chromatographic resin and the third chromatographic resin are not interrupted by an additional chromatographic resin. Thus, the one or more additional chromatographic resins are not present or the one or more additional resins are before the second chromatographic resin and/or after the third chromatographic resin.

The method comprises a feedstock stream (e.g., a first feedstock stream and a second feedstock stream) containing at least a first constituent and a second constituent. In some embodiments, the feedstock stream comprises at least three constituents (e.g., at least four constituents, at least five constituents, at least six constituents, at least seven constituents, or at least eight constituents). Typically, at least three constituents of the feedstock stream are from a *cannabis* plant. In certain embodiments, the at least 3 constituents are selected from THC, CBD, pigments, and waxes.

The first feedstock stream and the second feedstock stream can be from the same or different source. Accordingly, the first feedstock stream and the second feedstock stream can come from the same or different batches of feedstock.

The first chromatographic resin, the second chromatographic resin, and the third chromatographic resin can be any suitable chromatographic resin. Typically, the first chromatographic resin, the second chromatographic resin, and the third chromatographic resin are a stationary phase described herein (i.e., OR-1, OR-2, OR-2 prime, or OR-5). The first chromatographic resin, the second chromatographic resin, and the third chromatographic resin can be the same or different. In some embodiments, the first chromatographic resin, the second chromatographic resin, and the third chromatographic resin are a same resin.

In embodiments where the first chromatographic resin, the second chromatographic resin, and the third chromatographic resin are a same resin, the resin can be a modified activated carbon adsorbent having an average particle size range of from about 45 microns to about 1700 microns and having an iodine number greater than about 900.

In embodiments where the first chromatographic resin, the second chromatographic resin, and the third chromatographic resin are a same resin, the resin can be a modified hydrophobic adsorbent comprising a styrene-divinylbenzene (DVB) resin having about 4% to about 8% crosslinking or a poly(methyl methacrylate) (PMMA) resin, an average particle size range of from about 25 microns to about 300 microns, an average bulk density of from about 0.4 g/mL to about 0.6 g/mL, an average surface area of from about 450 $m^2/g$ to about 550 $m^2/g$, and an average pore volume of from about 0.7 mL/g to about 0.9 mL/g.

In embodiments where the first chromatographic resin, the second chromatographic resin, and the third chromatographic resin are a same resin, the resin can be a hydrophobic resin having an average particle diameter of from about 25 to about 300 microns, an average bulk density of from about 0.75 to about 0.85 g/mL, an average surface area of from about 450 to about 500 $m^2/g$, and an average pore volume of from about 0.7 to about 0.9 mL/g.

In embodiments where the first chromatographic resin, the second chromatographic resin, and the third chromatographic resin are a same resin, the resin can be a hydrophobic polystyrene-divinylbenzene adsorbent having an average particle diameter of from about 250 to about 600 microns, an average bulk density of from about 0.6 g/mL to about 0.9 g/mL, and a water content of from about 55 to about 65%. In some embodiments, the method increases the isolated yield of the first constituent relative to a method comprising: passing a first feedstock stream through a first chromatographic resin to form a first eluate having a higher ratio of the first constituent to the second constituent than in the first feedstock stream; passing the first eluate through a second chromatographic resin to form a second eluate having a higher ratio of the first constituent to the second constituent than in the first eluate, under otherwise identical conditions.

In some embodiments, the methods described herein provide an isolated yield (i.e., a percent recovery) of at least about 50% or more (e.g., at least about 55% or more, at least about 60% or more, at least about 65% or more, at least about 70% or more, at least about 80% or more, at least about 85% or more, at least about 90% or more, or at least about 95% or more) of the cannabinoid (e.g., CBD and/or CBDA). In preferred embodiments, the methods described herein provide an isolated yield of from about 75% to about 100% (e.g., about 75% to about 90%, about 75% to about 85%, about 80% to about 100%, about 80% to about 90%, about 85% to about 100%, or about 85% to about 90%) of the cannabinoid (e.g., CBD and/or CBDA).

In some embodiments, the methods described herein provide a level of THC and/or THCA of less than about 2 wt. % (e.g., less than about 1.5 wt. %, less than about 1 wt. %, less than about 0.8 wt. %, less than about 0.6 wt. %, less than about 0.5 wt. %, less than about 0.4 wt. %, less than about 0.3 wt. %, less than about 0.2 wt. %, or less than about 0.1 wt. %) based on the amount of the cannabinoid (e.g., CBD or CBDA). In preferred embodiments, the methods described herein provide a level of THC and/or THCA of less than about 0.5 wt. % based on the amount of the cannabinoid (e.g., CBD or CBDA).

The disclosure is further illustrated by the following exemplary purification protocols.

Figure 10:
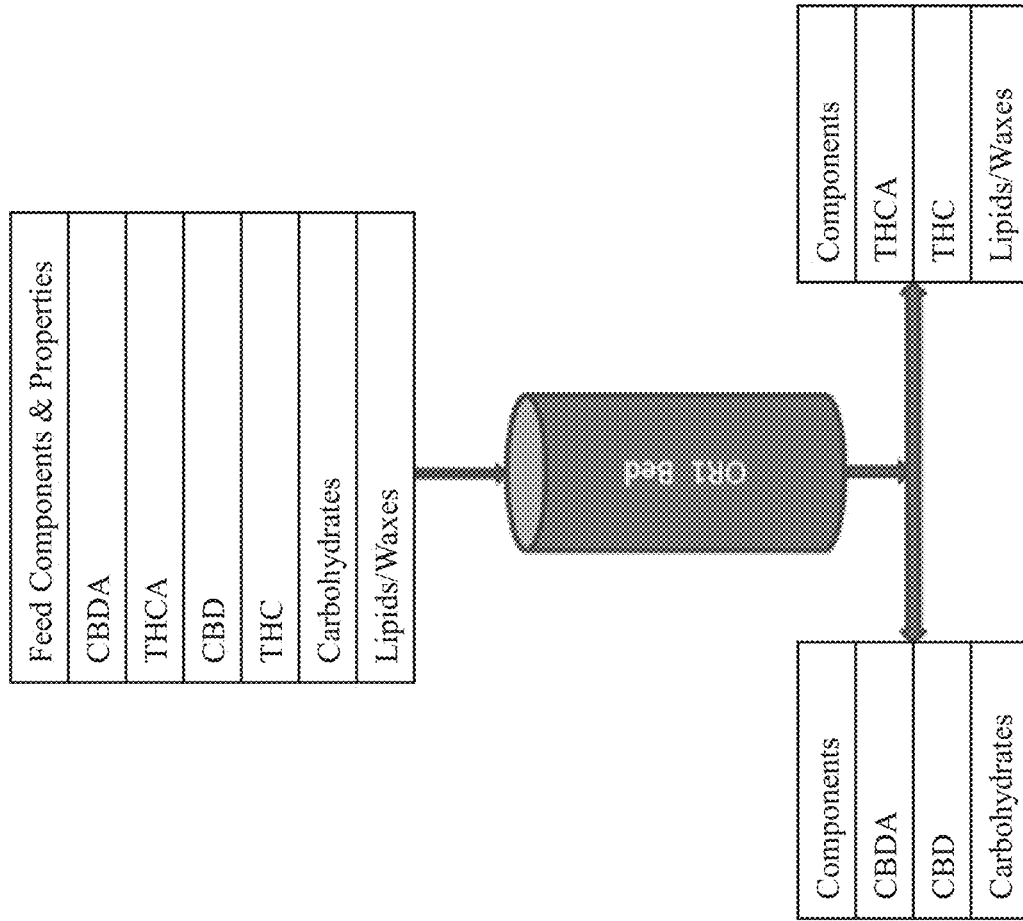
FIG. 10 is a schematic diagram for an OR-1 single column used for THC/A removal from a decolorized hemp extract in embodiments of the disclosure.

In embodiments, OR-1 can be used as a single column. The OR-1 single column can be used for THCA removal. As shown in FIG. 10, a hemp extract can be processed through a single column with OR-1 adsorbent to enrich CBD/CBDA with the removal of THC/THCA as well as Lipids and Waxes. Once the THC and THCA adsorption limit levels on the OR-1 stationary phase have been exceeded, the purification process is stopped. This CBD/CBDA material can then be decarboxylated, and the ethanol solvent can be removed. To the remaining CBD material, a liquid extraction using a non-polar alkane solvent can be performed to create an intermediately purified THC-free CBD product free of carbohydrates. The alkane solvent can be removed to create a final product of THC-free CBD, all using a single column.

Figure 11:
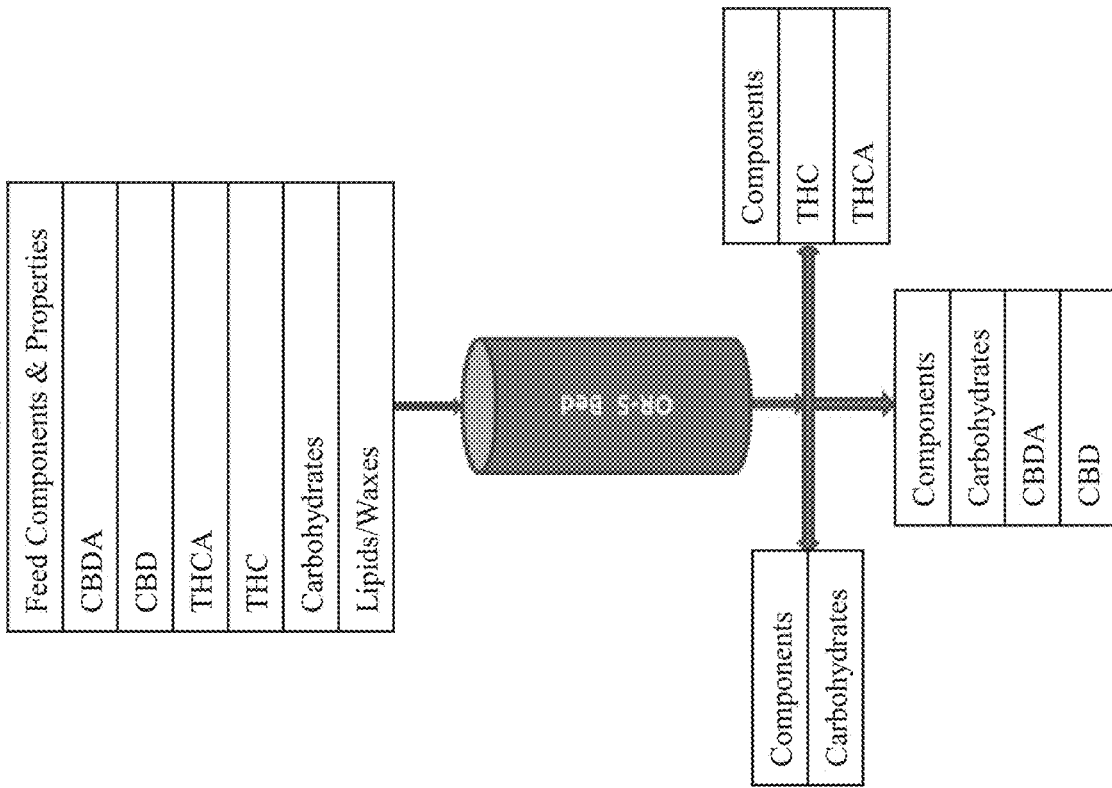
FIG. 11 is a schematic diagram for an OR-5 single column used for THC/THCA removal from a decolorized hemp extract in embodiments of the disclosure.

In embodiments, OR-5 can be used as a single column. The OR-5 single column can be used for THC/THCA removal. As shown in FIG. 11, a decolorized hemp extract can be processed through a single column packed with an OR-5 bed. After removal of the THC/THCA along with the Lipids and Waxes, the enriched CBD/CBDA stream contains Carbohydrates and other polar impurities. This material can be used directly for decarboxylation or other steps, or first the Carbohydrates can be removed from the enriched CBD/CBDA stream by liquid extraction using a non-polar alkane solvent.

Figure 12:
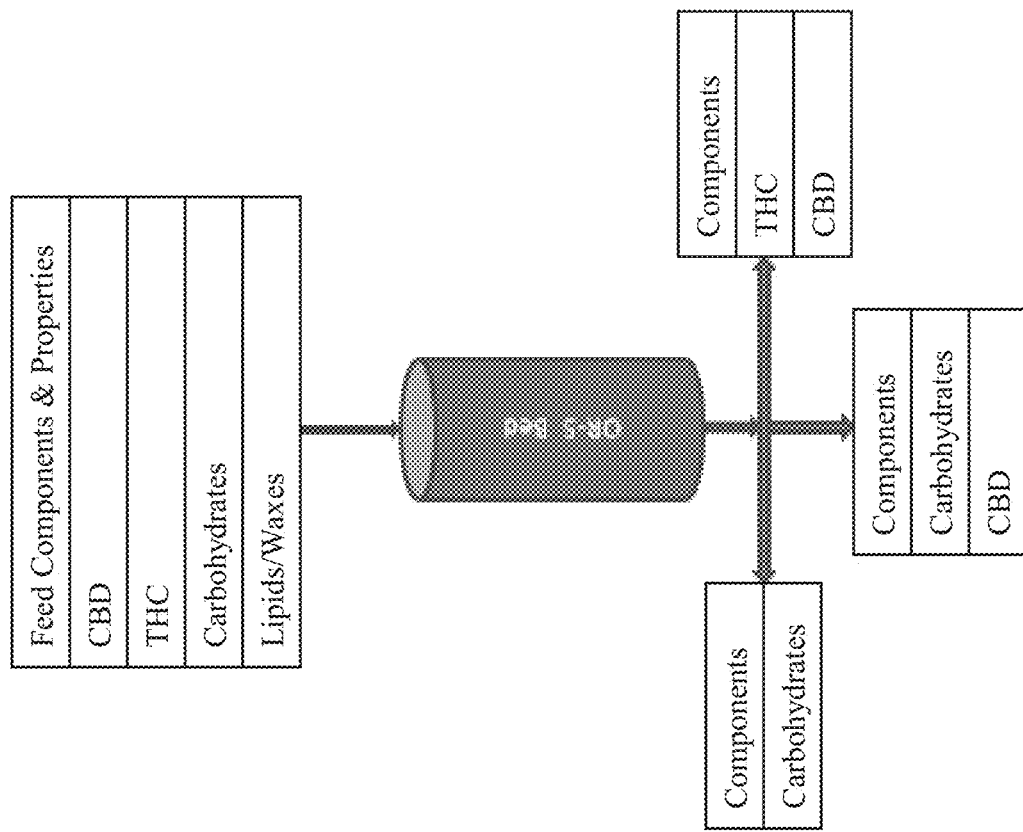
FIG. 12 is a schematic diagram for an OR-5 a single column used for THC removal from decolorized and decarboxylated hemp extract in embodiments of the disclosure.

In embodiments, OR-5 can be used as a single column. The OR-5 single column can be used for THC removal. As shown in FIG. 12, a decolorized as well as decarboxylated hemp extract comprising CBD and THC can be processed through a single column packed with an OR-5 bed. After removal of the THC along with the Lipids and Waxes, the enriched CBD stream contains Carbohydrates and other polar impurities. This material can be used directly for other steps, or first the Carbohydrates can be removed from the enriched CBD stream by liquid extraction using a non-polar alkane solvent. As shown in FIG. 12, the THC stream can also contain an amount of CBD.

In embodiments, OR-5 can be used as a single column. The OR-5 single column can be washed with ethanol for additional CBDA and CBD recovery. Initially, the OR-5 single column can be used for THC and THCA removal by passing a decolorized hemp extract through the OR-5 column as shown in FIG. 11. Then the OR-5 column is washed with ethanol to recover the CBDA and CBD that adsorbed to the OR-5 adsorbent for improvement in process recovery.

In embodiments, OR-5 can be used as a single column. The OR-5 single column can be washed with acetone for regeneration. Initially, the OR-5 single column can be used for THC and THCA removal by passing a decolorized hemp extract through the OR-5 column as shown in FIG. 11. Then the OR-5 column is washed with ethanol to recover the CBDA and CBD that adsorbed to the OR-5 adsorbent for improvement in process recovery. Following the ethanol wash, an acetone wash is conducted on the OR-5 column to regenerate the OR-5 adsorbent by eluting the THCA, THC, Lipids, Waxes, and Color that are adsorbed.

Figure 13:
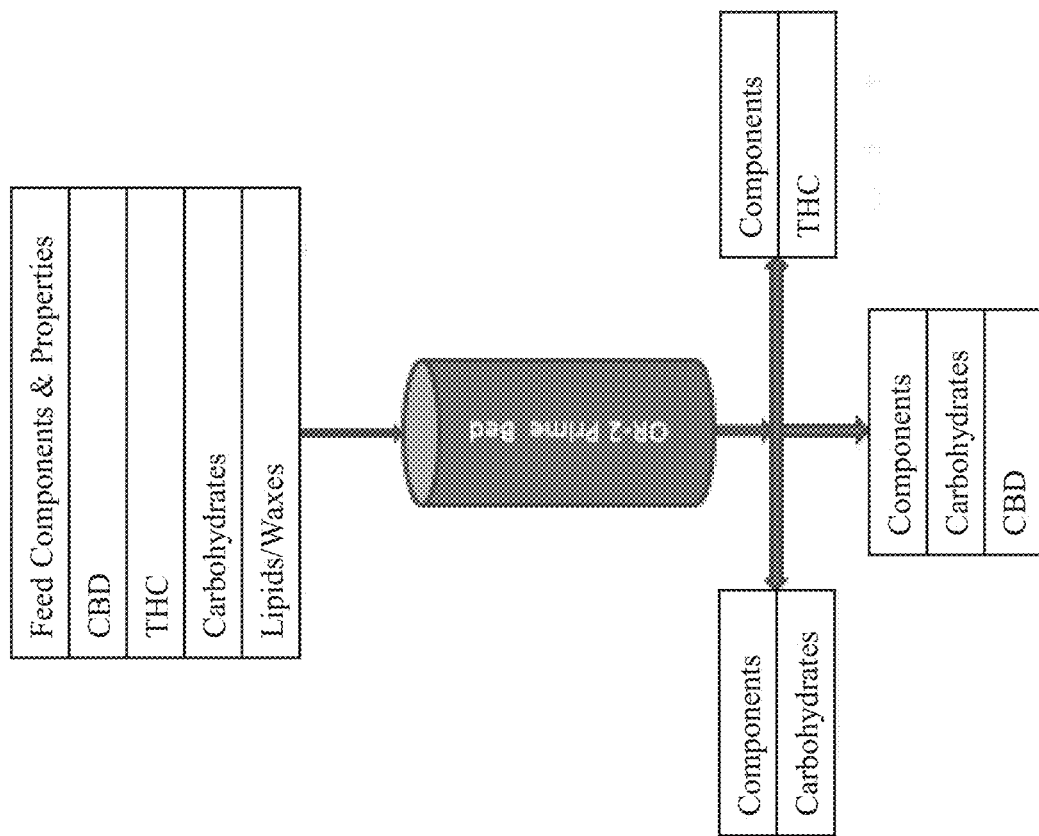
FIG. 13 is a schematic diagram for an OR-2 prime single column used for separation of CBD and THC from a decolorized and decarboxylated hemp extract in embodiments of the disclosure.

In embodiments, OR-2 prime can be used as a single column. The OR-2 prime single column can be used for separation of CBD and THC as illustrated in FIG. 13. The OR-2 prime column can be conditioned by washing with 60:40 (v/v) ethanol:water for 2-5 bed volumes. An OR-2 prime column feed is prepared by: using ethanol solvent to extract the desired compounds from industrial hemp leaves, then processing the extract through OR-1 chromatography to decolorize (remove Chlorophylls & Pigments). Decolorized hemp extract is then placed in a still to apply heat to activate/convert the acidic form of the cannabinols. Lastly, decolorized and decarboxylated hemp extract is admixed with water to create a (50-80)/(50-20) (v/v) ethanol:water solvent composition to create the feed liquid for the OR-2 prime column. The feed is loaded onto the OR-2 prime single column until CBD breakthrough is detected. The initial effluent fractions up to the CBD breakthrough point contain mainly carbohydrate impurities. Once CBD breakthrough is seen, elution with (50-60)/(50-40) ethanol:water is started and CBD and THC are continuously monitored in the effluent. Once CBD is measured to be negligible in the effluent, elution with 100% Ethanol is started for THC elution. The procedure is stopped when THC in effluent is measured to be negligible. The CBD-enriched material can be used directly for other steps, or first the Carbohydrates can be removed from the enriched CBD stream by liquid extraction using a non-polar alkane solvent. Using 100% ethanol as final desorbent, OR-2 prime is regenerated for repeatable, continuous use.

In embodiments, OR-5 can be used in a SMB technology system. The OR-5 SMB technology system can be used for THC/THCA removal from decolorized hemp extract. Decolorized hemp extract used as feed liquid is processed through an OR-5 single column acting as a guard bed. The initial effluent fractions are THCA and THC free. After a specific number of bed volumes, the capacity of this single OR-5 guard bed column for THCA and THC retention is exceeded. However, this guard bed column can still be utilized for reduction in Wax impurities. The effluent from the guard bed is then passed onto the SMB as feed liquid. Processing the effluent from the single column through SMB technology further purifies CBD and CBDA. OR-5 stationary phase is regenerated using an ethanolic mixture for continuous, repeatable chromatographic separation.

In embodiments, OR-5 can be used in a SMB technology system. OR-5 adsorbent in SMB technology can remove THC from decolorized and decarboxylated hemp extract. Decolorized and decarboxylated hemp extract used as feed liquid is processed through an OR-5 single column acting as a guard bed. The initial effluent fractions will be THC free. After a specific number of bed volumes, the capacity of this single OR-5 guard bed column for THC retention is exceeded. However, this guard bed column can still be utilized for reduction in Wax impurities. The effluent from the guard bed is then passed onto the SMB system as feed liquid. Processing the effluent from the single column through SMB technology further purifies CBD. OR-5 stationary phase is regenerated using an ethanolic mixture for continuous, repeatable chromatographic separation.

In embodiments, OR-2 prime adsorbent can be used in SMB technology. OR-2 prime adsorbent can be used in SMB technology to remove THC from decolorized and decarboxylated hemp extract. Decolorized and decarboxylated hemp extract is used as feed for processing through a SMB technology system with OR-2 prime adsorbent to produce THC-free CBD. OR-2 prime stationary phase can be regenerated using an ethanolic and water mixture (80:20 wt:wt, ethanol:water) for continuous, repeatable chromatographic separation.

In embodiments, OR-1 adsorbent can be used in batch chromatographic mode. OR-1 adsorbent can be used in batch chromatographic mode operations for removal of THC along with other impurities like non-polar Waxes/Lipids, and Color pigments from hemp extract used as feed liquid. The batch column chromatography method utilizes a single column in various positions for multiple streams of impurity reduction. The identified stationary phase that is favorable for the batch column method has the capability to remove the THC, Wax, and Colored pigment impurity streams. Furthermore, this stationary phase exhibits an affinity for retention of specific impurity streams based on its (the stationary phase) level of saturation from incoming feed liquid. The level of saturation can be determined based on the volume of the stationary phase bed that has been packed into a chromatography column, and the volume of feed liquid that has been passed through that bed. The result is a purified CBD output liquid that is free of THC. The batch mode of this chromatography sequence allows for increased recovery of CBD lost between successive steps. A fresh, unused unit column in the batch sequence can be used for THC removal, with the unfortunate consequence of CBD loss due to adsorption to the stationary phase. As this unit column in the batch sequence is used for additional impurity removal, a higher degree of affinity is found between the stationary phase and the impurity, compared to the stationary phase and CBD. Thus, CBD is displaced from the column into the output liquid streams, increasing CBD recovery to >85%. The collected output liquid is used in purification of the n+1th batch of columns. Impurities removed by adsorption to column in batch mode cause displacement of CBD into output liquid streams. This increases recovery of CBD to >90% by mass. Output liquid streams in batch steps used for Wax or Colored pigment removal contains CBD which was temporarily lost by column adsorption in the THC-removal step. Output liquid streams in batch steps used for Wax or Colored pigment removal contains recovered CBD which is purified in the n+1th batch of OR-1 columns. OR-1 column is fully exhausted and is not regenerated after the conclusion of the Colored pigment removal step. However, affordability of stationary phase allows for purchasing of large amounts to repack a fresh column for repetition of the batch process.

According to one embodiment of the disclosure and with reference to FIG. 1, a process is disclosed for the separation and purification of cannabidiol (CBD) from dried *cannabis* leaves from the *Cannabis sativa*, *Cannabis indica*, or *Cannabis ruderalis* plant are passed in line 50 to an extraction/filtration zone 100 and therein admixed with an effective amount of ethanol in line 52 and agitated by conventional means to provide a crude cannabinoid extract stream. Preferably, the crude cannabinoids are admixed with ethanol to provide a filtered crude cannabinoid stream which comprises from about 3.4 wt. % to about 4.0 wt. % total crude cannabinoids in the mixture. More preferably, the filtered crude cannabinoid stream comprises from about 3.4 wt. % to about 3.7 wt. % total cannabinoids in the mixture. The concentration of solids in the filtered crude cannabinoid stream varies from about 60 to about 80 g/l and is preferably about 75 g/l. The crude cannabinoid extract stream is then filtered in the first filtration zone of the extraction/filtration zone 100, in a series of successive filters of decreasing pore size, starting at a pore size of 100 microns and reducing to about 10 microns in 3 or more stages. Preferably, the successive filters comprise a 100 micron, a 20 micron, and a 10 micron filter. The 100 micron pore size filter comprises a bag filter made of felt for high capacity flow and capturing solids. The 20 and 10 micron pore size filters consist of cartridges comprising polyethylene and are pleated for providing higher surface area. The cartridges had O-rings on a fitting at the end for seating and are adapted to be disposed inside a cylindrical, stainless steel housing. The filtered liquid leaf extract stream, or filtered crude extract stream comprises cannabidiol (CBD), cannabidiolic acid (CBDA), tetrahydrocannabinol (THC), tetrahydrocannabinolic acid (THCA), other cannabinols, color bodies, impurities and ethanol. The filtered crude extract stream is green in color due to the presence of the color bodies and chlorophyll, is essentially free of particles, and is comprised of approximately 20-40 g/L of cannabidiol (CBD) and cannabidiolic acid (CBDA). The filtered crude extract stream is withdrawn from the extract/filtration zone 100 in line 54. The filtered crude extract stream in line 54 is passed to a decolorization zone 102 to remove at least a portion of color bodies and provide a decolorized crude extract stream in line 56. In the decolorization zone 102, the filtered crude extract stream was passed through a 10 μm filter to the top of a decolorization chromatographic column. The column was operated at a decolorization pressure of 2.72 atm to about 4.08 atm (40-60 psig) and a decolorization temperature ranging from 20-25° C. The decolorization chromatographic column was packed with adsorbent OR1, a modified activated carbon adsorbent which was heat treated to provide a highly hydrophobic adsorbent which is essentially free of hydroxyl groups, has an average particle diameter of between 177 and 250 microns, and an iodine number of above 900 mg/g. At least a portion of the color bodies are selectively retained on the decolorization chromatographic column adsorbent, shown as line 61; and, the recovered elute is withdrawn as a decolorized extract stream in line 56. Essentially all chlorophylls were removed from the filtered crude extract stream in line 61 following a decolorization wash, although some color bodies remain resulting in an amber color of the decolorized extract stream. The solids concentration in the decolorized extract stream is about 40-45% cannabidiol (CBD) and cannabidiolic acid (CBDA) and the concentration of total solids in the decolorized extract stream is approximately 20-35 g/L. The solids concentration was determined following evaporation of the ethanol from the decolorized extract stream to dryness. The decolorized extract stream in line 56 was passed to a first evaporation zone 104 to remove the ethanol solvent from the decolorized extract stream in line 56 to provide an evaporated extract stream in line 58 and a first recovered ethanol stream in line 63. In the first evaporation zone 104 the decolorized extract stream in line 56 was subjected to vacuum distillation, to remove essentially all of the solvent from the decolorized extract stream in line 56. The vacuum distillation was operated at a vacuum pressure of about −0.60 to about −0.74 atm (−18 to −22 in Hg) and a temperature of about 90 to about 110° C. At least a portion of ethanol solvent recovered from the vacuum distillation unit as a first recovered ethanol stream in line 63 was reused, i.e., recycled, as solvent for the extraction/filtration zone 100. Following removal of the ethanol solvent in line 63, the remaining cannabinoid oil comprising cannabidiol (CBD), cannabidiolic acid (CBDA), tetrahydrocannabinolic acid (THCA), tetrahydrocannabinol (THC), lipids and plant waxes, impurities and other cannabinoids was passed to an activation zone 106 and therein subjected to an activation step. The activation zone 106 could be a physically separate zone or the remaining cannabinoid oil in line 58 can be retained in the vacuum distillation vessel for heating. The activation step comprises a decarboxylation reaction wherein the remaining cannabinoid oil in line 58 was subjected to a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion. The decarboxylation reaction time was sufficient to fully decarboxylate essentially all of the acidic components to provide a decarboxylated cannabinoid oil comprising cannabidiol (CBD), tetrahydrocannabinol (THC), lipids and plant waxes, and other cannabinoids, and being essentially free of cannabidiolic acid (CBDA) and tetrahydrocannabinolic acid (THCA). During the course of the decarboxylation reaction, it was surprisingly discovered that at least a portion of impurities in the remaining cannabinoid oil in line 58 were aggregated into a sludge like material which floated on top of the decarboxylated cannabinoid oil. Thus, following the decarboxylation reaction, a first water wash step was performed to remove the aggregated impurities, by subjecting the decarboxylated cannabinoid oil to the water wash step, wherein a first water wash stream in line 53 is introduced to solubilize the impurities and to remove the aggregated impurities in line 57 from the decarboxylated cannabinoid oil stream in line 60. At the conclusion of the decarboxylation and water wash steps, the decarboxylated cannabinoid oil stream in line 60 is passed to a dewaxing zone 108. In the dewaxing zone, at least a portion of lipids and plant waxes are removed from the decarboxylated cannabinoid oil stream. In the dewaxing zone 108, the decarboxylated cannabinoid oil stream in line 60 is admixed with a solution in line 51 containing ethanol and water sufficient to provide a dewaxing solvent volume ratio of 80/20 solvent volume to volume of decarboxylated cannabinoid oil (800 L of ethanol and 200 L of water to make 1000 L of the mixture) and to provide a dewaxing feed stream. The dewaxing feed stream comprises about 40-45 g/L concentration of total solids (on a dry basis). It was discovered that the concentration of solids in the dewaxing feed stream should not exceed a dewaxing feed solids concentration 50 g/L on a dry basis. The dewaxing feed stream was passed to the top of a dewaxing column at a dewaxing column pressure of about 2.72 atm to about 4.08 atm (40-60 psi) and room temperature (20-25° C.). The dewaxing column was packed adsorbent OR1, a hydrophobic activated carbon adsorbent which is essentially free of hydroxyl groups, and has an average particle diameter of between 177 and 250 microns, and an iodine number of above 900 mg/g. The effluent from the dewaxing column, or dewaxed cannabinoid oil stream in line 62 comprises cannabidiol (CBD), tetrahydrocannabinol (THC), and other cannabinoids, and has a concentration of total solids in the dewaxed cannabinoid oil stream in line 62 of from 35 to 40 g/L, and comprises about 60 wt. % cannabidiol on a dry basis. The dewaxed cannabinoid oil stream in line 62 is withdrawn from the dewaxing zone 108 and passed via lines 62 to a simulated moving bed (SMB) zone 110 for reverse phase separation. The simulated moving bed zone 110 is further described herein below in connection with FIG. 2. The simulated moving bed zone 110 consists of 8 SMB adsorbent beds, and also comprises a rotary valve, an arrangement of valves and piping, and a valve control system, which for simplicity are not shown. Each of the simulated moving bed (SMB) adsorbent beds contain a simulated moving bed (SMB) stationary phase adsorbent consisting of OR2. OR2 is modified hydrophobic adsorbent comprising a styrene-divinylbenzene (DVB) resin having 4 to 8 percent crosslinking or a poly(methyl methacrylate) (PMMA) resin. The OR2 hydrophobic adsorbent has an average particle diameter of between 25 and 300 microns, an average bulk density (g/mL) of from 0.4 to 0.6, an average surface area ($m^2$/g) of from 450 to 550, and an average pore volume of from 0.70-0.90 (mL/g). In the simulated moving bed zone 110, a mobile phase desorbent stream is introduced via line 66. The simulated moving bed (SMB) zone 110 provides a primary raffinate stream in line 70, an extract stream in line 68, and a secondary raffinate stream in line 65. The secondary raffinate stream in line 65 is returned to the simulated moving bed zone to be admixed with the mobile phase desorbent stream to offset the need for desorbent. The extract stream comprises mobile phase desorbent, cannabidiol (CBD), and tetrahydrocannabinol (THC) and is passed to desorbent recovery. Following the removal of the mobile phase desorbent by vacuum distillation (not shown) the recovered mobile phase desorbent may be recycled to the simulated moving bed zone and the resulting solvent free extract stream is passed to waste disposal. The primary raffinate stream in line 70 comprises cannabidiol (CBD), dewaxing solvent, and is essentially free of tetrahydrocannabinol (THC), and comprises an average primary raffinate solids concentration of 5.0-7.0 g/L and has an average cannabidiol (CBD) purity of 80-87% w/w and an average THC content of 0.0% wt. %. The primary raffinate stream in line 70 is passed to a second evaporation zone 114, operating at a second evaporation temperature of about 80-100° C. and a second evaporation pressure of about −0.53 to −0.67 atm (−16 to −20 in Hg) to separate the primary raffinate stream into a high purity cannabinoid oil stream in line 72 and a second recovered solvent stream on line 73. At least a portion of the high purity cannabinoid oil stream can be withdrawn via lines 72 and 85 as a high purity cannabidiol oil (CBD) product, or the remainder of the high purity cannabinoid oil stream is passed for further purification via lines 72 and 74 to a polishing zone 115. In the polishing zone 115, the high purity cannabinoid oil stream in line 74, which is essentially free of any solvent, was further processed to remove polar impurities. The high purity cannabinoid oil stream in line 72 is passed to a polishing zone 115, wherein the high purity cannabinoid oil stream is admixed with a sufficient amount of a non-polar solvent, such as hexane, introduced in line 75, to provide a polishing zone feed stream having a cannabidiol (CBD) oil concentration of about 10-30 wt. % cannabidiol (CBD) oil. The polishing zone feed stream is agitated and allowed to settle at room temperature for a period of 120 to 720 minutes to allow the polar compounds, such as sugars and carbohydrates, to precipitate from the supernatant non-polar solution, and the supernatant non-polar solution is passed to a second filtration zone 116 via lines 76 and 78 to separate the precipitate the sugars and carbohydrates from the supernatant non-polar solution to provide a filtered supernatant non-polar solution in line 80. The filtered supernatant non-polar solution in line 80 is passed to a third evaporation zone 118 to recover essentially all of the non-polar solvent to provide recovered non-polar solvent, comprising hexane, in line 82 and to provide an evaporated cannabinoid oil stream in line 84. At least a portion of the recovered non-polar solvent in line 82 may be returned to the polishing zone 115 to be admixed with the non-polar solvent to provide makeup non-polar solvent. The evaporated cannabinoid oil stream in line 84 is passed to a wash zone 119, wherein the evaporated cannabinoid oil stream is alternately washed up to at least 3 times, first with an ethanol wash stream comprising 100 wt. % ethanol introduced via line 86 in an alcohol wash ratio of 1:3 L of ethanol to Kg of evaporated cannabinoid oil; and second, with a fourth water wash stream in line 87 using a water wash ratio of 1:3 L of water to Kg of cannabinoid oil, and wherein after each wash step, the washed cannabinoid oil is evaporated to dryness. At the conclusion of the last water wash and drying steps, a phytocannabinoid rich oil, essentially free of tetrahydrocannabinol (THC) is withdrawn in line 90. Being essentially free of tetrahydrocannabinol (THC) means that the concentration of tetrahydrocannabinol (THC) in the phytocannabinoid rich oil is less than 0.001 wt. %, or non-detectable (ND).

The phytocannabinoid rich oil composition is described herein below in Tables 1 and 2. Table 1 shows the composition of the cannabinoids in the Phytocannabinoid rich oil, and Table 2 shows the residual solvent analysis. No detectable solvent was present in the phytocannabinoid rich oil product, and the phytocannabinoid rich oil product is free of any THC.

TABLE 1

Cannabinoid profile of Phytocannabinoid rich oil

| Compound | Amount reported % |
|---|---|
| THC | 0 |
| THCV | 0 |
| CBG | 0-4% |
| CBD | 70-86% |
| CBN | 0-3% |
| THCA | 0 |
| CBDA | 0 |
| CBDV | 0-1% |
| Other | 30-10% |

TABLE 2

Residual Solvent Analysis of Phytocannabinoid rich oil

| Solvent | Amount Reported |
|---|---|
| Ethanol | ND |
| Isopropanol | ND |
| Hexane | ND |
| Ethyl Acetate | ND |
| Heptane | ND |

ND—None Detected

Alternatively, the supernate hexane solution in line 78 can be further processed to provide a cannabinoid isolate product. Accordingly, the supernate non-polar solution in line 76, or the filtered supernate non-polar solution in lines 81 and 92 is passed to an isolate chromatography zone 120 via line 92. The isolate chromatography zone 120 comprises a first isolate chromatography column 121 and a second isolate chromatography column 122, wherein the first and the second isolate chromatography columns (121, 122) are serially connected and in serial fluid communication. The supernate hexane solution in line 78 or the filtered supernate hexane solution in line 81 is passed to the top of the first isolate chromatography column 121 via line 92 and the effluent from the first isolate chromatography column 121 is withdrawn in line 94 and passed to the top of the second isolate chromatography column 122. The effluent from the second isolate chromatography column 122 is withdrawn via line 96 from the bottom of the isolate chromatography column 122. The first isolate chromatography column 121 can be one or more physical column containing the OR3 adsorbent, and the second isolate chromatography column 122 can be one or more physical column containing the OR4 adsorbent. OR3 is a modified hydrophilic adsorbent comprising a spherical polar silica adsorbent having a high level of silanol (Si—O—H) groups, having an average particle diameter of between 60 and 200 microns, having an average surface area of between 450 and 550 m$^2$/g, having an average pore volume of between 0.7 and 0.85 mL/g, and having a pore size of between 50 to 75 Angstroms (0.005-0.0075 microns). OR4 is an activated alumina adsorbent having an average particle diameter of between 50 and 200 microns, an average bulk density of 0.85 g/ml, an average surface area of between 140-170 m$^2$/g, and an average pore diameter of greater than 60 Angstroms (0.006 microns). The supernate non-polar solution in line 92 is passed sequentially through the first and second isolate chromatography columns (121, 122) to provide an isolate elute stream in line 96. The isolate elute stream comprises non-polar solvent, cannabidiol, and a minor amount of other cannabinoids. The isolate elute stream in line 96 is passed to a crystallization zone 124, wherein the isolate elute stream in line 96 is subjected to a freezer temperature of equal to or less than about −20° C. for a freezer period of about 24 to about 72 hours to permit primary high purity cannabidiol crystals, containing from about 96 to about 98 wt. % cannabidiol to form. The primary high purity cannabidiol (CBD) crystals are harvested and re-dissolved into a crystal isolate solution by admixing the primary high purity cannabidiol crystals with hexane to provide the crystal isolate solution comprising 20-30% by weight cannabidiol CBD oils. The crystal isolate solution is placed into stainless steel receptacles and allowed to stand at room temperature for a period of 24-72 hours to permit secondary high purity CBD crystals to again form. The secondary high purity CBD crystals formed, comprise about 99% CBD by weight. These secondary high purity CBD crystals are harvested and passed via line 98 to a rotary evaporation zone 126. In the rotary evaporation zone 126, the secondary crystals are heated until molten, and any residual hexane in the secondary high purity CBD crystals is evaporated. The secondary high purity CBD crystals typically melt at about 70° C., although the crystal melting point will vary depending upon the vacuum pressure in the flask of the rotary evaporator. Following evaporation of the hexane from the secondary high purity crystals, a third water wash stream introduced via line 99, using 200 g of water for every 1 Kg of secondary high purity crystals, is carried out in the rotary evaporation zone. Following the third water wash, any remaining water is removed by evaporation to complete dryness and the washed secondary high purity crystals are allowed to solidify to provide a solid CBD aggregate, which is essentially free of any detectable amount of THC. The solidification temperature is generally about 37° C. The solid CBD aggregate in line 130 was harvested. The solid CBD aggregate may be granulated or crushed into powder to provide a powdered CBD isolate product which is essentially free of THC. The resulting powdered CBD isolate is described by Tables 3 and 4. Table 3 describes the CBD purity of the isolate, while Table 4 describes the residual solvent analysis of the CBD isolate powder.

TABLE 3

Cannabinoid profile of Isolates

| Compound | Amount Reported |
|---|---|
| THC | 0 |
| THCV | 0 |
| CBG | 0 |
| CBD | 99.7% w/w |
| CBN | 0 |
| THCA | 0 |
| CBDA | 0 |
| CBDV | 0 |
| Other | 0.3 |

TABLE 4

Residual Solvent Analysis of CBD Isolates

| Solvent | Amount Reported |
|---|---|
| Ethanol | ND |
| Isopropanol | ND |
| Hexane | ND |
| Ethyl Acetate | ND |
| Heptane | ND |

Figure 2:
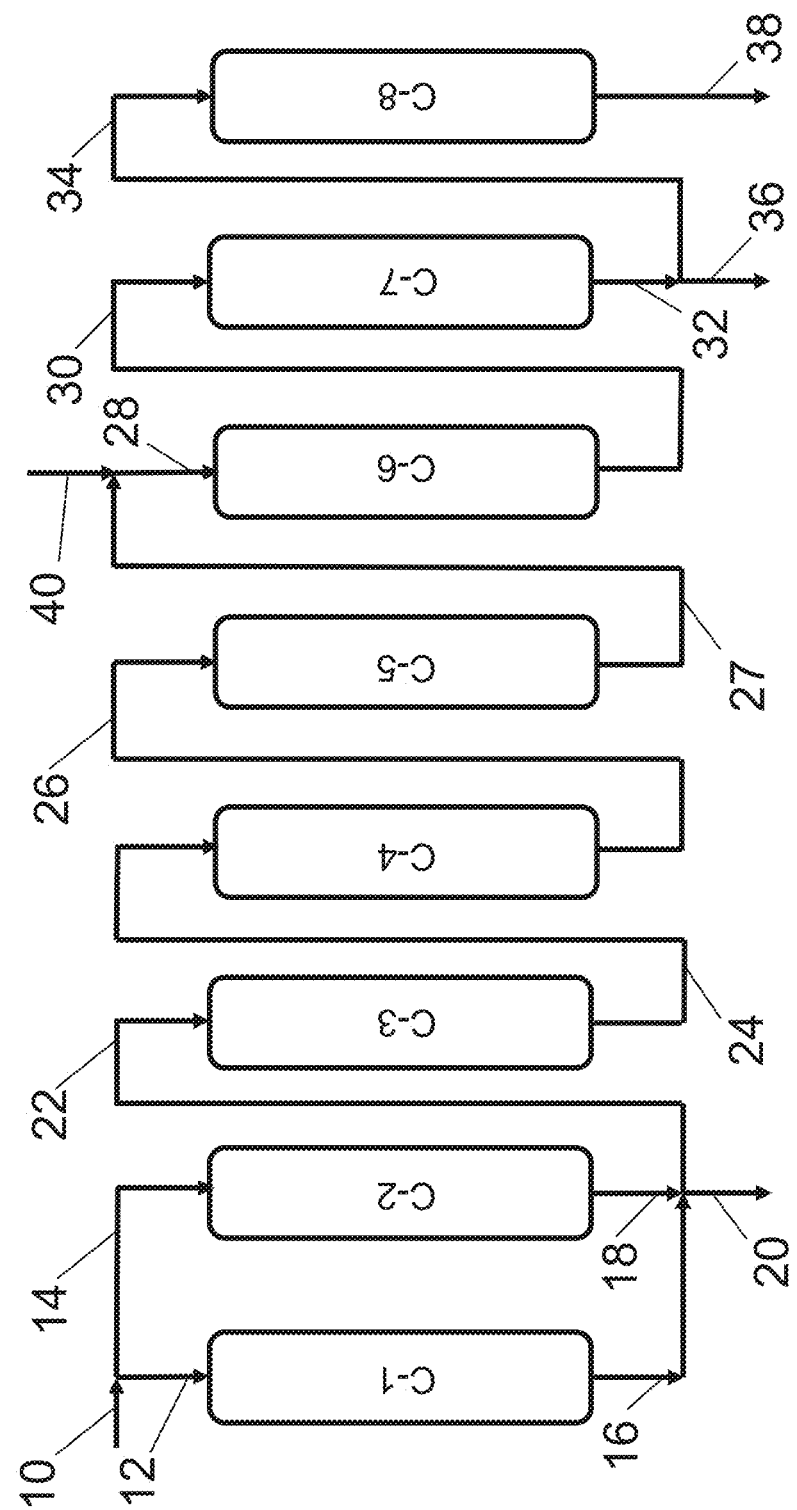
FIG. 2 is a schematic process flow diagram illustrating a configuration of the simulated moving bed cycle for a simulated moving bed zone in one embodiment of the disclosure.

According to one embodiment of the disclosure and with reference to FIG. 2, the simulated moving bed system is a continuous simulated moving bed system which continuously processes the dewaxed cannabinoid oil stream in line 10 to provide a primary raffinate stream in line 36. There were eight adsorption beds arranged in series and connected through a proprietary pneumatic valve array (not shown). The SMB scheme shown in FIG. 2 is a 2-3-2-1 arrangement, wherein 2 adsorbent beds (C-1, C-2) were operated in a desorption zone, 3 adsorbent beds (C-3, C-4, C-5) were operated in a rectification zone, 2 adsorbent beds (C-6, C-7) were operated in an adsorption zone, and 1 adsorbent bed (C-8) was operated in a concentration zone for raffinate. The independently working and programmable 72-valve array contains no moving parts, occupies only 3 μl per valve, and responds within 100 ms. Fluid flow is controlled by four independent pumps. The valve switching and pump flow rates are controlled via the SembaPro Software. The eight adsorbent beds (C-1, C-2, C-3, C-3, C-4, C-5, C-6, C-7, and C-8) were cylinders of 304 stainless steel, each adsorbent bed having an inside column diameter of 15 cm (6 inch) and a column length of 90 cm (36 inches), and each adsorbent bed contained about 10 Kg of OR2 adsorbent. The rotary valve system was operated on a cycle, wherein bed switching occurred at every 10-20 minute intervals. The eight adsorption beds were arranged in serial fluid communication such that fluid introduced at the top of any adsorbent bed n continued to the next highest adsorbent bed n+1 by passing the effluent from the bottom of adsorbent bed n to the top of adsorbent bed n+1. The adsorbent beds were operated in four zones, zone 1 (desorption), zone 2 (rectification), zone 3 (adsorption), and zone 4 (concentration), whereby the SMB feedstock stream, or dewaxed hemp oil stream, or cannabinoid oil stream in line 40 was loaded on to zone 3 (C-6) by introducing the SMB feedstock stream via lines 40 and 28 to adsorbent bed C-6. In zone 3, cannabidiol (CBD) was selectively adsorbed in adsorbent beds C-6 and C-7, and the primary raffinate stream was withdrawn in lines 32 and 36 from adsorbent bed C-7. The primary raffinate had with an average primary raffinate solids concentration of 5.0-7.0 g/L and an average cannabidiol (CBD) purity of 80-87% w/w and an average THC purity of 0.0% w/w. The primary raffinate in line 68 can be passed to an evaporation zone (not shown) to recover the solvent; and, following evaporation of the primary raffinate stream to dryness, provides a high purity cannabidiol (CBD) oil stream which is essentially free of THC. At least a portion of the primary raffinate steam in line 32 was passed to zone 4 comprising adsorbent bed C-8 in line 34 and a secondary raffinate stream was withdrawn from adsorbent bed C-8 in line 38. The secondary raffinate is withdrawn in line 38 at a very small flow rate compared to the flow rate of the primary raffinate flow rate and comprises essentially no cannabidiol (CBD) or THC oils. The secondary raffinate stream can be directly returned to zone 1 to offset the amount of the mobile phase desorbent in line 10. In the same step, a polar mobile phase desorbent in line 10, comprising an 80:20 volume mixture of ethanol and water, was simultaneously introduced to zone 1, comprising adsorbent beds C-1 and C-2, via lines 12 and 14, respectively. The mobile phase was passed through zone 1 in parallel through adsorbent beds C-1 and C-2, and the effluent of adsorbent beds C-1 and C-2 was withdrawn in lines 16 and 18, respectively, and combined to form an SMB extract stream in line 20. The SMB extract stream comprises the mobile phase desorbent, THC and CBD. The SMB extract stream line 20 is passed to a second evaporation zone for solvent recovery (not shown). A portion of the SMB extract stream in line 22 was passed to zone 2 (comprising adsorbent beds C-3, C-4, and C-5) and introduced to the top of adsorbent bed C-3, and continuing serially through adsorbent beds C-3, C-4, and C-5 via lines 24, and 26, respectively. The effluent withdrawn from the bottom of adsorbent bed C-5 was passed to the top of adsorbent bed C-6 in line 27, and admixed with the SMB feedstock stream in line 40 before being passed to adsorbent bed C-6 in line 28. At the completion of each SMB cycle, the adsorbent beds was advanced to move countercurrent to the SMB feedstock, whereby adsorbent bed C-2 shifts to the left to the position previously occupied by C-1 and C-1 was shifted to the position previously occupied by adsorbent bed C-8.

In another embodiment, the disclosure includes the steps of extracting crude *cannabis* from dry hemp leaves. The steps of the leaf extraction comprise:
  i) combining dry hemp leaves with a first portion of food grade ethanol to provide a first leaf/solvent mixture and agitating the first leaf/solvent mixture;
  ii) soaking the first leaf/solvent mixture for an effective soaking time to form a first ethanol layer;
  iii) decanting the first ethanol layer to provide a first decant stream and a first portion of wet leaves;
  iv) combining a second portion of food grade ethanol with the first portion of wet leaves to provide a second leaf/solvent mixture and agitating the second leaf/solvent mixture and decanting a second ethanol layer to provide a second decant stream and residual leaves; and,
  v) pressing the residual leaves to provide a third decant stream and combining the first decant stream, the second decant stream and the third decant streams to provide the crude *cannabis* extract stream.

The leaf extraction process is carried out at atmospheric pressure and room temperature of about 25° C. The first leaf mixture is allowed to soak for an effective soaking time comprising about 8 to 12 hours. Preferably, the combined decant streams should have a solids concentration of between about 23 to about 30 g/Liter. More preferably the combined decant streams should have a maximum solids concentration less than about 30 g/Liter.

EMBODIMENTS

Principles of the present disclosure are incorporated in the following embodiments:

Embodiment (1). A method for the purification of cannabidiol (CBD) in a crude *cannabis* extract stream to provide at least one high purity cannabidiol product selected from the group consisting of a high purity cannabinoid oil stream, a phytocannabinoid rich oil, a solid CBD aggregate and mixtures thereof being essentially free of tetrahydrocannabinol, said process comprising (a) passing the crude *cannabis* extract stream comprising debris and small particles, cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a first filtration zone comprising a series of successive filters of decreasing pore size, starting at a pore size of 100 microns and reducing to about 10 microns in 3 or more stages to remove debris and small particles in a progressive filtration step to provide a filtered crude cannabinoid stream; (b) passing the filtered crude cannabinoid stream comprising cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a decolorization zone comprising a 10 µm filter and a decolorization chromatographic column containing a modified activated carbon adsorbent which was heat treated to provide a highly hydrophobic adsorbent which is essentially free of hydroxyl groups, has an average particle diameter of between 177 and 250 microns, and an iodine number of above 900 mg/g and operated at a decolorization pressure of 2.72 atm to about 4.08 atm (40-60 psig) and a decolorization temperature ranging from 20-25° C. to remove at least a portion of color bodies and essentially all of the chlorophyll to provide a decolorized extract stream; (c) passing the decolorized extract stream to a first evaporation zone operated at a first vacuum pressure of −0.60 to about −0.74 atm (−18 to −22 in Hg) and a temperature of about 90 to about 110° C. to remove at least a portion of the ethanol to provide an evaporated extract stream which is essentially free of ethanol; (d) passing the evaporated extract stream comprising cannabidiol (CBD), cannabidiolic acid (CBDA), tetrahydrocannabinolic acid (THCA), tetrahydrocannabinol (THC), sugars and carbohydrates, lipids, plant waxes, impurities and other cannabinoids to an activation zone and therein subjected to a carboxylation reaction at a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion, said decarboxylation reaction time being sufficient to fully decarboxylate essentially all of the cannabidiolic acid (CBDA) and tetrahydrocannabinolic acid (THCA) to provide a decarboxylated cannabinoid oil comprising cannabidiol (CBD), tetrahydrocannabinol (THC), lipids, plant waxes, and other cannabinoids, and being essentially free of cannabidiolic acid (CBDA) and tetrahydrocannabinolic acid (THCA), and water washing the decarboxylated cannabinoid oil to remove at least a portion of the impurities to provide a washed decarboxylated cannabinoid oil; (e) admixing the washed decarboxylated cannabinoid oil with a dewaxing solvent having a dewaxing solvent volume ratio of 80 volume units of ethanol to 20 volume units water to provide a dewaxing feed stream and passing the dewaxing feed stream to a dewaxing zone containing a dewaxing column at a dewaxing column pressure of about 2.72 atm to about 4.08 atm (40-60 psi) and room temperature (20-25° C.), said dewaxing column containing a hydrophobic activated carbon adsorbent which is essentially free of hydroxyl groups, and having an average particle diameter of between 177 and 250 microns, and an iodine number of above 900 mg/g to remove at least a portion of the lipids and plant waxes and to provide a dewaxed cannabinoid oil stream comprising cannabidiol (CBD), tetrahydrocannabinol (THC), sugars and carbohydrates, color bodies, and other cannabinoids; (f) passing the dewaxed cannabinoid oil stream and a mobile phase desorbent stream consisting of a mixture of food grade ethanol and water to a reversed phase simulated moving bed zone comprising a plurality of adsorbent beds containing a modified hydrophobic adsorbent comprising a styrene-divinylbenzene (DVB) resin having about 4% to about 8% crosslinking or a poly(methyl methacrylate) (PMMA) resin, said modified hydrophobic adsorbent having an average particle diameter of between 25 and 300 microns, an average bulk density (g/mL) of from 0.4 to 0.6, an average surface area ($m^2/g$) of from 450 to 550, and an average pore volume of from 0.70-0.90 (mL/g) to provide a primary raffinate stream comprising cannabidiol (CBD), mobile phase desorbent, sugars and carbohydrates, color bodies, and other cannabinoids and being essentially free of tetrahydrocannabinol (THC), an extract stream comprising mobile phase desorbent, cannabidiol (CBD), and tetrahydrocannabinol (THC), and a secondary raffinate stream comprising mobile phase desorbent, cannabidiol (CBD) which is admixed with the mobile phase desorbent and returned to the reversed phase simulated moving bed zone; (g) passing the primary raffinate to a second evaporation zone to remove mobile phase desorbent to provide a second recovered solvent stream comprising the mobile phase desorbent and to provide the high purity cannabinoid oil stream having an average cannabidiol purity of greater than 80 wt. % and being essentially free of tetrahydrocannabinol (THC); (h) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids; (i) passing a portion of the supernatant non-polar solution to a second filtration zone to remove the precipitate and to provide a filtered supernatant non-polar solution; (j) passing the filtered supernatant non-polar solution to a third evaporation zone to remove at least a portion of the non-polar solvent to provide an evaporated cannabinoid oil stream and a recovered non-polar solvent stream, and returning at least a portion of the recovered non-polar solvent stream to the polishing zone to be admixed with the non-polar solvent; (k) passing the evaporated cannabinoid oil stream to a wash zone and alternately washing the evaporated cannabinoid oil stream first with an ethanol wash stream comprising pure ethanol in a washing ratio of 1:3 liters of ethanol to kilograms of evaporated cannabinoid oil, and second with a fourth water wash stream in a water wash ratio of 1:3 liters of water to kilograms of evaporated cannabinoid oil, and wherein following each step, washed cannabinoid oil is evaporated to dryness to provide a phytocannabinoid rich oil which is essentially free of tetrahydrocannabinol (THC) and comprising greater than 80 wt. % cannabinoid (CBD); (1) passing a portion of the supernatant non-polar solution to a isolate chromatography zone comprising a first isolate chromatography column and a second isolate chromatography column being in serial fluid communication and wherein the first isolate chromatography column contains a modified hydrophilic adsorbent comprising a spherical polar silica adsorbent having a high level of silanol groups, an average particle diameter of between 60 and 200 microns, an average surface area of between 450 to 550 $m^2/g$ an average pore volume of between 0.7 and 0.85 mL/g and a pore size of between 0.005 and 0.0075 microns, wherein the second isolate chromatography column contains an activated alumina adsorbent having an average particle diameter of between 50 to 200 microns, an average bulk density of 0.85 g/mL, an average surface area of between 140 and 170 $m^2/g$, and an average pore diameter of greater than 0.006 microns to provide an isolate elute stream comprising cannabidiol (CBD), non-polar solvent and other cannabinoids; (m) passing the isolate elute stream to a crystallization zone, wherein the isolate elute stream is subjected to a freezer temperature of equal to or less than about −20° C. for a freezer period of about 24 to about 72 hours to permit primary high purity cannabidiol crystals, containing from about 96 wt. % to about 98 wt. % cannabidiol to form, harvesting the primary high purity cannabidiol (CBD) crystals and admixing the primary high purity cannabidiol crystals with hexane to provide the crystal isolate solution comprising 20-30% by weight cannabidiol CBD oils, and retaining the crystal isolate solution at room temperature for a period of 24-72 hours to permit secondary high purity CBD crystals to form and harvesting the secondary high purity CBD crystals; (n) passing the secondary high purity CBD crystals to a rotary evaporation zone wherein the secondary high purity crystals are heated until molten to evaporate any residual non-polar and washed with a third water wash stream at least three times in the rotary evaporation, wherein at the completion of each wash step the secondary high purity crystals are dried to complete dryness to provide a solid CBD aggregate which is essentially free of tetrahydrocannabinol (THC) and has a cannabidiol purity of greater than 99 wt. %; and, (o) withdrawing at least one high purity cannabidiol product being essentially free of tetrahydrocannabinol (THC) a stream selected from the group consisting of the high purity cannabinoid oil stream, the phytocannabinoid rich oil, the solid CBD aggregate and mixtures thereof.

Embodiment (2). The method of embodiment (1) further comprising passing solid CBD aggregate to a granulator to provide a powdered high purity CBD product which has a cannabidiol purity of greater than 99 wt. % and is essentially free of tetrahydrocannabinol.

Embodiment (3). The method of embodiment (1) or (2), wherein the primary raffinate stream has a solids concentration of about 5 to about 7 grams per liter.

Embodiment (4). The method of any one of embodiments (1)-(3), wherein the modified hydrophobic adsorbent comprises a styrene-divinylbenzene (DVB) resin having about 4% to about 8% crosslinking.

Embodiment (5). The method of any one of embodiments (1)-(4), wherein the mobile phase desorbent stream consists of a mixture of food grade ethanol and water having an ethanol to water ratio of 80 parts to 20 parts ethanol volume/volume.

Embodiment (6). The method of any one of embodiments (1)-(5), wherein the reverse phase simulated moving bed zone comprises is a 2-3-2-1 arrangement, wherein 2 adsorbent beds are operated in a desorption zone, 3 adsorbent beds are operated in a rectification zone, 2 adsorbent beds are operated in an adsorption zone, and 1 adsorbent bed is operated in a concentration zone.

Embodiment (7). A method for the purification of cannabidiol (CBD) in a crude *cannabis* extract stream to provide at least one high purity cannabidiol product being essentially free of tetrahydrocannabinol, said process comprising (a) passing the crude *cannabis* extract stream comprising debris and small particles, cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a first filtration zone comprising a series of successive filters of decreasing pore size, starting at a pore size of 100 microns and reducing to about 10 microns in 3 or more stages to remove debris and small particles in a progressive filtration step to provide a filtered crude cannabinoid stream; (b) passing the filtered crude cannabinoid stream comprising cannabidiol, tetrahydrocannabinol, cannabidiolic acid, tetrahydrocannabinolic acid, other cannabinols, chlorophylls, color bodies, sugars and carbohydrates, lipids, plant waxes, impurities, and ethanol to a decolorization zone comprising a 10 μm filter and a decolorization chromatographic column containing a modified activated carbon adsorbent which was heat treated to provide a highly hydrophobic adsorbent which is essentially free of hydroxyl groups, has an average particle diameter of between 177 and 250 microns, and an iodine number of above 900 mg/g and operated at a decolorization pressure of 2.72 atm to about 4.08 atm (40-60 psig) and a decolorization temperature ranging from 20-25° C. to remove at least a portion of color bodies and essentially all of the chlorophyll to provide a decolorized extract stream; (c) passing the decolorized extract stream to a first evaporation zone operated at a first vacuum pressure of −0.60 to about −0.74 atm (−18 to −22 in Hg) and a temperature of about 90 to about 110° C. to remove at least a portion of the ethanol to provide an evaporated extract stream which is essentially free of ethanol; (d) passing the evaporated extract stream comprising cannabidiol (CBD), cannabidiolic acid (CBDA), tetrahydrocannabinolic acid (THCA), tetrahydrocannabinol (THC), sugars and carbohydrates, lipids, plant waxes, impurities and other cannabinoids to an activation zone and therein subjected to a carboxylation reaction at a decarboxylation temperature of about 90 to about 120° C. and a decarboxylation pressure of about −0.6 atm to 0.74 atm for a decarboxylation reaction time of about 5 to about 8 hours, or sufficient time for the decarboxylation reaction to occur and proceed to completion, said decarboxylation reaction time being sufficient to fully decarboxylate essentially all of the cannabidiolic acid (CBDA) and tetrahydrocannabinolic acid (THCA) to provide a decarboxylated cannabinoid oil comprising cannabidiol (CBD), tetrahydrocannabinol (THC), lipids, plant waxes, and other cannabinoids, and being essentially free of cannabidiolic acid (CBDA) and tetrahydrocannabinolic acid (THCA), and water washing the decarboxylated cannabinoid oil to remove at least a portion of the impurities to provide a washed decarboxylated cannabinoid oil; (e) admixing the washed decarboxylated cannabinoid oil with a dewaxing solvent having a dewaxing solvent volume ratio of 80 volume units of ethanol to 20 volume units water to provide a dewaxing feed stream and passing the dewaxing feed stream to a dewaxing zone containing a dewaxing column at a dewaxing column pressure of about 2.72 atm to about 4.08 atm (40-60 psi) and room temperature (20-25° C.), said dewaxing column containing a hydrophobic activated carbon adsorbent which is essentially free of hydroxyl groups, and having an average particle diameter of between 177 and 250 microns, and an iodine number of above 900 mg/g to remove at least a portion of the lipids and plant waxes and to provide a dewaxed cannabinoid oil stream comprising cannabidiol (CBD), tetrahydrocannabinol (THC), sugars and carbohydrates, color bodies, and other cannabinoids; (f) passing the dewaxed cannabinoid oil stream and a mobile phase desorbent stream consisting of a mixture of food grade ethanol and water to a reversed phase simulated moving bed zone comprising a plurality of adsorbent beds containing a modified hydrophobic adsorbent comprising a styrene-divinylbenzene (DVB) resin having about 4% to about 8% cross-linking or a poly(methyl methacrylate) (PMMA) resin, said modified hydrophobic adsorbent having an average particle diameter of between 25 and 300 microns, an average bulk density (g/mL) of from 0.4 to 0.6, an average surface area (m²/g) of from 450 to 550, and an average pore volume of from 0.70-0.90 (mL/g) to provide a primary raffinate stream comprising cannabidiol (CBD), mobile phase desorbent, sugars and carbohydrates, color bodies, and other cannabinoids and being essentially free of tetrahydrocannabinol (THC), an extract stream comprising mobile phase desorbent, cannabidiol (CBD), and tetrahydrocannabinol (THC), and a secondary raffinate stream comprising mobile phase desorbent, cannabidiol (CBD) which is admixed with the mobile phase desorbent and returned to the reversed phase simulated moving bed zone; (g) passing the primary raffinate to a second evaporation zone to remove mobile phase desorbent to provide a second recovered solvent stream comprising the mobile phase desorbent and to provide a high purity cannabinoid oil stream having an average cannabidiol purity of greater than 80 wt. % and being essentially free of tetrahydrocannabinol (THC); and, (h) withdrawing the high purity cannabinoid oil stream as the at least one high purity cannabidiol product having an average cannabidiol purity of greater than 80 wt. %.

Embodiment (8). The method of embodiment (7), further comprising (a) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids; (b) passing a portion of the supernatant non-polar solution to a second filtration zone to remove the precipitate and to provide a filtered supernatant non-polar solution; (c) passing the filtered supernatant non-polar solution to a third evaporation zone to remove at least a portion of the non-polar solvent to provide an evaporated cannabinoid oil stream and a recovered non-polar solvent stream, and returning at least a portion of the recovered non-polar solvent stream to the polishing zone to be admixed with the non-polar solvent; (d) passing the evaporated cannabinoid oil stream to a wash zone and alternately washing the evaporated cannabinoid oil stream first with an ethanol wash stream comprising pure ethanol in a washing ratio of 1:3 liters of ethanol to kilograms of evaporated cannabinoid oil, and second with a fourth water wash stream in a water wash ratio of 1:3 liters of water to kilograms of evaporated cannabinoid oil, and wherein following each step, washed cannabinoid oil is evaporated to dryness to provide a phytocannabinoid rich oil which is essentially free of tetrahydrocannabinol (THC) and comprising greater than 80 wt. % cannabinoid (CBD); and, (e) withdrawing the phytocannabinoid rich oil as the high purity cannabidiol product having an average cannabidiol purity of greater than 80 wt. %.

Embodiment (9). The method of embodiment (7) or (8), further comprising (a) passing at least a portion of the high purity cannabinoid oil stream to a polishing zone and therein admixing the high purity cannabinoid oil stream with a non-polar solvent stream comprising hexane and therein allowing the admixture to settle to form a precipitate comprising sugars and carbohydrates and a supernatant non-polar solution comprising cannabidiol (CBD), color bodies, and other cannabinoids; (b) passing a portion of the supernatant non-polar solution to a isolate chromatography zone comprising a first isolate chromatography column and a second isolate chromatography column being in serial fluid communication and wherein the first isolate chromatography column contains a modified hydrophilic adsorbent comprising a spherical polar silica adsorbent having a high level of silanol groups, an average particle diameter of between 60 and 200 microns, an average surface area of between 450 to 550 $m^2/g$ an average pore volume of between 0.7 and 0.85 mL/g and a pore size of between 0.005 and 0.0075 microns, wherein the second isolate chromatography column contains an activated alumina adsorbent having an average particle diameter of between 50 to 200 microns, an average bulk density of 0.85 g/mL, an average surface area of between 140 and 170 $m^2/g$, and an average pore diameter of greater than 0.006 microns to provide an isolate elute stream comprising cannabidiol (CBD), non-polar solvent and other cannabinoids; (c) passing the isolate elute stream to a crystallization zone, wherein the isolate elute stream is subjected to a freezer temperature of equal to or less than about −20° C. for a freezer period of about 24 to about 72 hours to permit primary high purity cannabidiol crystals, containing from about 96 wt. % to about 98 wt. % cannabidiol to form, harvesting the primary high purity cannabidiol (CBD) crystals and admixing the primary high purity cannabidiol crystals with hexane to provide the crystal isolate solution comprising 20-30% by weight cannabidiol CBD oils, and retaining the crystal isolate solution at room temperature for a period of 24-72 hours to permit secondary high purity CBD crystals to form and harvesting the secondary high purity CBD crystals; (d) passing the secondary high purity CBD crystals to a rotary evaporation zone wherein the secondary high purity crystals are heated until molten to evaporate any residual non-polar and washed with a third water wash stream at least three times in the rotary evaporation, wherein at the completion of each wash step the secondary high purity crystals are dried to complete dryness to provide a solid CBD aggregate which is essentially free of tetrahydrocannabinol (THC) and has a cannabidiol purity of greater than 99 wt. %; and, (e) withdrawing the solid CBD aggregate as the high purity cannabidiol product having an average cannabidiol purity of greater than 99 wt. %.

Embodiment (10). The method of any one of embodiments (1)-(6), further comprising further comprising the following leaf extraction steps prior to step a): (a) combining dry hemp leaves with a first portion of food grade ethanol to provide a first leaf/solvent mixture and agitating the first leaf/solvent mixture; (b) soaking the first leaf/solvent mixture for an effective soaking time to form a first ethanol layer; (c) decanting the first ethanol layer to provide a first decant stream and a first portion of wet leaves; (d) combining a second portion of food grade ethanol with the first portion of wet leaves to provide a second leaf/solvent mixture and agitating the second leaf/solvent mixture and decanting a second ethanol layer to provide a second decant stream and residual leaves; and, (e) pressing the residual leaves to provide a third decant stream and combining the first decant stream, the second decant stream and the third decant streams to provide the crude *cannabis* extract stream.

Embodiment (11). The method of any one of embodiments (1)-(6) or (10), wherein the effective soaking time comprises about 8 to 12 hours.

Embodiment (12). The method of any one of embodiments (1)-(6), (10), or (11), further comprising passing a portion of the supernatant non-polar solution to a second filtration zone to remove the precipitate and to provide a filtered supernatant non-polar solution and passing the filtered supernatant non-polar solution to the isolate chromatography zone.

Embodiment (13). A method of separating a cannabinoid from a *cannabis* plant, the *cannabis* plant including the cannabinoid and at least one impurity, the method comprising: combining the *cannabis* plant and a solvent to form a crude *cannabis* extract stream; processing the crude *cannabis* extract stream into a simulated moving bed (SMB) feedstock stream by removing at least a portion of at least one impurity in the crude *cannabis* extract stream; and passing the SMB feedstock stream through a SMB zone to provide a primary raffinate stream having a higher purity of the cannabinoid than in the SMB feedstock stream as measured by weight percentage of the solid content and a SMB extract stream having a lower purity of the cannabinoid than in the SMB feedstock stream as measured by weight percentage of the solid content.

Embodiment (14). The method of embodiment (13), wherein the *cannabis* plant is selected from *Cannabis sativa, Cannabis indica, Cannabis rudralis*, and mixtures thereof.

Embodiment (15). The method of embodiment (13) or (14), wherein the *cannabis* plant comprises dried hemp, *cannabis* leaves, or a mixture thereof.

Embodiment (16). The method of any one of embodiments (13)-(15), wherein the solvent comprises ethanol.

Embodiment (17). The method of any one of embodiments (13)-(16), wherein said at least one impurity comprises at least one of color bodies, acidic components, lipids, and *cannabis* plant waxes, and wherein processing the crude *cannabis* extract stream includes at least one of decolorizing the crude *cannabis* extract stream to remove at least a portion of the color bodies from the crude *cannabis* extract stream, activating the crude *cannabis* extract stream to remove at least a portion of the acidic components from the crude *cannabis* extract stream, and dewaxing the crude *cannabis* extract stream to remove at least a portion of the lipids and *cannabis* plant waxes from the crude *cannabis* extract stream.

Embodiment (18). The method of any one of embodiments (13)-(17), wherein processing the crude *cannabis* extract stream into the SMB feedstock stream includes passing the crude *cannabis* extract stream through a first chromatographic resin, and passing the SMB feedstock stream through the SMB zone includes passing the SMB feedstock stream through a second chromatographic resin, the second chromatographic resin being different from the first chromatographic resin.

Embodiment (19). The method of any one of embodiments (13)-(18), wherein the SMB zone comprises a plurality of adsorbent beds, each bed containing a modified hydrophobic adsorbent comprising a poly(methyl methacrylate) (PMMA) resin or a styrene-divinylbenzene (DVB) resin having 4 percent to 8 percent crosslinking.

Embodiment (20). The method of embodiment (19), wherein the plurality of adsorbent beds are arranged in serial fluid communication such that fluid introduced at a top of any adsorbent bed (n) passes to the next highest adsorbent bed (n+1).

Embodiment (21). The method of embodiment (20), further comprising: advancing each adsorbent bed, such that adsorbent bed n+1 becomes adsorbent bed n after advancing, and adsorbent bed n prior to advancing becomes adsorbent bed n+x after advancing, wherein adsorbent bed n+x is the highest adsorbent bed in the serial fluid communication arrangement.

Embodiment (22). The method of embodiment (20), wherein there are eight adsorbent beds in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a concentration zone, respectively.

Embodiment (23). The method of any one of embodiments (13)-(22), wherein the cannabinoid is cannabidiol (CBD).

Embodiment (24). The method of any one of embodiments (13)-(23), wherein said at least one impurity of the crude *cannabis* extract stream comprises a second cannabinoid selected from cannabidiolic acid (CBDA), cannabigerol (CBG), cannabinol (CBN), tetrahydrocannabinol (THC), tetrahydrocannabinolic acid (THCA), and combinations thereof.

Embodiment (25). The method of any one of embodiments (13)-(24), wherein said at least one impurity of the crude *cannabis* extract stream comprises tetrahydrocannabinol (THC), and wherein the primary raffinate stream is essentially free of THC.

Embodiment (26). The method of embodiment (25), wherein the average mass recovery of CBD in the primary raffinate stream is 80 wt. % or more.

(27) The method of embodiment (25), wherein the CBD of the primary raffinate stream has an average purity of 35% to 50% as determined by HPLC.

Embodiment (28). The method of any one of embodiments (13)-(27), further comprising: removing the primary raffinate stream to provide a cannabinoid oil stream.

Embodiment (29). The method of embodiment (28), further comprising: mixing the cannabinoid oil stream with a non-polar solvent to provide a polishing zone feed stream; agitating the polishing zone feed stream for a first period of time; allowing the agitated polishing zone feed stream to settle for a second period of time; and filtering the settled polishing zone feed stream to provide a filtered non-polar solution having a higher purity of the cannabinoid than in the cannabinoid oil stream as measured by weight percentage of the solids content.

Embodiment (30). The method of embodiment (29), further comprising: removing the filtered non-polar solution to provide an evaporated cannabinoid oil stream.

Embodiment (31). The method of embodiment (30), further comprising: washing the evaporated cannabinoid oil stream with a wash solvent to provide a washed cannabinoid oil stream.

Embodiment (32). The method of embodiment (31), wherein washing the evaporated cannabinoid oil stream includes washing the evaporated cannabinoid oil stream more than once.

Embodiment (33). The method of embodiment (31), wherein the wash solvent comprises methanol, water, or mixtures thereof.

Embodiment (34). The method of any one of embodiments (31)-(33), further comprising: drying the washed cannabinoid oil stream.

Embodiment (35). The method of any one of embodiments (31)-(34), wherein the washed cannabinoid oil stream is THC free.

Embodiment (36). The method of any one of embodiments (29)-(35), further comprising: passing at least a portion of the filtered non-polar solution through an isolate chromatography zone comprising a first chromatography column and a second chromatography column to provide an isolate elute stream having a higher purity of the cannabinoid than in the filtered non-polar solution as measured by weight percentage of the solid content, wherein the first and second columns are connected in serial fluid communication.

Embodiment (37). The method of embodiment (36), wherein the first chromatography column comprises a hydrophilic resin comprising a spherical polar silica adsorbent having Si—OH groups, an average particle diameter between 60-200 microns, an average surface area between 450-550 m$^2$/g, an average pore volume of between 0.7-0.85 mL/g, and a pore size between 0.005-0.0075 microns.

Embodiment (38). The method of embodiment (36) or (37), wherein the second chromatography column comprises an activated alumina adsorbent having an average particle diameter between 50-200 microns, an average bulk density of 0.85 g/mL, an average surface area between 140-170 m$^2$/g, and an average pore diameter greater than 0.006 microns.

Embodiment (39). The method of any one of embodiments (36)-(38), further comprising: cooling the isolate elute stream for a cooling period of time, to thereafter provide crystallized cannabidiol.

Embodiment (40). The method of embodiment (39), wherein the crystallized cannabidiol has a purity of from about 96 wt. % to about 98 wt. % as determined by HPLC.

Embodiment (41). The method of embodiment (39) or (40), further comprising: recrystallizing the crystallized cannabidiol.

Embodiment (42). The method of embodiment (41), wherein the recrystallized cannabidiol has a purity of greater than 99 wt. % as determined by HPLC.

Embodiment (43). A method of separating a cannabinoid from a *cannabis* plant containing the cannabinoid and at least one impurity, the method comprising: preparing a feedstock stream comprising the *cannabis* plant and a solvent; passing the feedstock stream through a chromatographic resin to provide an eluate stream having a higher purity of the cannabinoid than in the feedstock stream as measured by weight percentage of the solid content, the chromatographic resin comprising one or more of the following: a first resin comprising a modified activated carbon adsorbent having an average particle size range of from about 45 to about 1700 microns; a second resin comprising a modified hydrophobic adsorbent comprising a styrene-divinylbenzene (DVB) resin or a poly(methyl methacrylate) (PMMA) resin; a third resin comprising a hydrophobic resin having an average particle diameter of from about 25 microns to about 300 microns; a fourth resin comprising a hydrophobic polystyrene-divinylbenzene adsorbent having an average particle diameter of from about 250 microns to about 600 microns, or a mixture thereof.

Embodiment (44). The method of embodiment (43), wherein the cannabinoid is CBD, CBDA, or a mixture thereof.

Embodiment (45). The method of embodiment (43) or (44), wherein the at least one impurity is waxes, lipids, pigments, or mixtures thereof.

Embodiment (47). The method of any one of embodiments (43)-(45), wherein said at least one impurity of the crude *cannabis* extract stream comprises a second cannabinoid selected from cannabigerol (CBG), cannabinol (CBN), tetrahydrocannabinol (THC), tetrahydrocannabinolic acid (THCA), and combinations thereof.

Embodiment (48). The method of any one of embodiments (43)-(47), wherein the feedstock stream comprises a hemp extract, a decolorized hemp extract, a decolorized and decarboxylated hemp extract, or any combination thereof.

Embodiment (49). The method of embodiment (48), wherein the feedstock stream is hemp extract.

Embodiment (50). The method of embodiment (48), wherein the feedstock stream is decolorized hemp extract.

Embodiment (51). The method of embodiment (48), wherein the feedstock stream is decolorized and decarboxylated hemp extract.

Embodiment (52). The method of any one of embodiments (43)-(51), wherein the chromatographic resin is the first resin comprising a modified activated carbon adsorbent having an average particle size range of from about 45 to about 1700 microns and having an iodine number greater than about 900.

Embodiment (53). The method of any one of embodiments (43)-(51), wherein the chromatographic resin is the second resin comprising a modified hydrophobic adsorbent comprising a styrene-divinylbenzene (DVB) resin having about 4% to about 8% crosslinking or a poly(methyl methacrylate) (PMMA) resin, an average particle size range of from about 25 microns to about 300 microns, an average bulk density of from about 0.4 g/mL to about 0.6 g/mL, an average surface area of from about 450 $m^2/g$ to about 550 $m^2/g$, and an average pore volume of from about 0.7 mL/g to about 0.9 mL/g.

Embodiment (54). The method of any one of embodiments (43)-(51), wherein the chromatographic resin is the third resin comprising a hydrophobic resin having an average particle diameter of from about 25 microns to about 300 microns, an average bulk density of from about 0.75 g/mL to about 0.85 g/mL, an average surface area of from about 450 $m^2/g$ to about 500 $m^2/g$, and an average pore volume of from about 0.7 mL/g to about 0.9 mL/g.

Embodiment (55). The method of any one of embodiments (43)-(54), wherein the hydrophobic resin of the third resin is a C18 resin.

Embodiment (56). The method of any one of embodiments (43)-(51), wherein the chromatographic resin is the fourth resin comprising a hydrophobic polystyrene-divinylbenzene adsorbent having an average particle diameter of from about 250 microns to about 600 microns, an average bulk density of from about 0.6 g/mL to about 0.9 g/mL, and a water content of from about 55% to about 65%.

Embodiment (57). The method of any one of embodiments (43)-(56), wherein the chromatographic resin is in a single column.

Embodiment (58). The method of any one of embodiments (43)-(56), wherein the chromatographic resin is in more than one column.

Embodiment (59). The method of embodiment (58), wherein at least a portion of the more than one columns are arranged in a SMB configuration.

Embodiment (60). The method of embodiment (59), further comprising passing a first feedstock stream through a first chromatographic resin to form a first eluate having a higher purity of the cannabinoid than in the first feedstock stream as measured by weight percentage of the solid content; passing the first eluate through a second chromatographic resin to form a second eluate having a higher purity of the cannabinoid than in the first eluate as measured by weight percentage of the solid content; passing a second feedstock stream through the second chromatographic resin to form a third eluate having a higher purity of the cannabinoid than in the second feedstock stream as measured by weight percentage of the solid content; and passing the third eluate through a third chromatographic resin to form a fourth eluate having a higher purity of the cannabinoid than in the third eluate as measured by weight percentage of the solid content.

Embodiment (61). The method of any one of embodiments (43)-(60), wherein the chromatographic resin is (i) a combination of the first resin and the third resin, (ii) a combination of the first resin and the fourth resin, (iii) a combination of the third resin and the fourth resin, or (iv) a combination of the first resin, the third resin, and the fourth resin.

Embodiment (62). The method of embodiment (61), wherein each of the first resin, the third resin, and the fourth resin is in one or more separate columns.

Embodiment (63). The method of any one of embodiments (43)-(62), wherein the feedstock stream comprises ethanol.

Embodiment (64). The method of any one of embodiments (43)-(63), wherein said at least one impurity of the crude *cannabis* extract stream comprises THC and THCA and the resin is the first resin.

Embodiment (65). The method of any one of embodiments (43)-(64), further comprising regeneration of the chromatographic resin for subsequent separations.

Embodiment (66). The method of embodiment (65), wherein the regeneration comprises washing the chromatographic resin with a regeneration solution comprising less than 5 wt. % water.

Embodiment (67). The method of embodiment (66), wherein the regeneration solution comprises ethanol, acetone, or a combination thereof.

Embodiment (68). A method of purifying a composition containing at least a first constituent and a second constituent, the method comprising: passing a first feedstock stream through a first chromatographic resin to form a first eluate having a higher ratio of the first constituent to the second constituent than in the first feedstock stream; passing the first eluate through a second chromatographic resin to form a second eluate having a higher ratio of the first constituent to the second constituent than in the first eluate; passing a second feedstock stream through the second chromatographic resin to form a third eluate having a higher ratio of the first constituent to the second constituent than in the second feedstock stream; and passing the third eluate through a third chromatographic resin to form a fourth eluate having a higher ratio of the first constituent to the second constituent than in the third eluate.

Embodiment (69). The method of embodiment (68), wherein at least a portion of the first constituent from the first eluate adsorbs to the second chromatographic column.

Embodiment (70). The method of embodiment (69), further comprising eluting at least a portion of the adsorbed first constituent in the third eluate.

Embodiment (71). The method of any one of embodiments (68)-(70), wherein the first chromatographic resin and the second chromatographic resin are in a first serial fluid communication arrangement.

Embodiment (72). The method of embodiment (71), wherein the first serial fluid communication arrangement further comprises one or more additional chromatographic resins.

Embodiment (73). The method of embodiment (72), wherein the first chromatographic resin and the second chromatographic resin are interrupted by at least one of the one or more additional chromatographic resins.

Embodiment (74). The method of embodiment (72), wherein the first chromatographic resin and the second chromatographic resin are not interrupted by an additional chromatographic resin.

Embodiment (75). The method of any one of embodiments (68)-(74), wherein the second chromatographic resin and the third chromatographic resin are in a second serial fluid communication arrangement.

Embodiment (76). The method of embodiment (75), wherein the second serial fluid communication arrangement further comprises one or more additional chromatographic resins.

Embodiment (77). The method of embodiment (76), wherein the second chromatographic resin and the third chromatographic resin are interrupted by at least one of the one or more additional chromatographic resins.

Embodiment (78). The method of embodiment (76), the second chromatographic resin and the third chromatographic resin are not interrupted by an additional batch of chromatographic resin.

Embodiment (79). The method of any one of embodiments (68)-(78), wherein the first feedstock stream comprises at least 3 constituents.

Embodiment (80). The method of embodiment (79), wherein the first feedstock stream comprises at least 4 constituents.

Embodiment (81). The method of embodiment (79) or (80), wherein the at least 3 constituents are from a *cannabis* plant.

Embodiment (82). The method of embodiment (81), wherein the at least 3 constituents are selected from THC, CBD, pigments, and waxes.

Embodiment (83). The method of any one of embodiment (68)-(82), wherein the first chromatographic resin, the second chromatographic resin, and the third chromatographic resin are a same resin.

Embodiment (84). The method of embodiment (83), wherein the same resin is selected from: a first resin comprising a modified activated carbon adsorbent having an average particle size range of from about 45 to about 1700 microns; a second resin comprising a modified hydrophobic adsorbent comprising a styrene-divinylbenzene (DVB) resin or a poly(methyl methacrylate) (PMMA) resin having an average bulk density of from about 0.4 g/mL to about 0.6 g/mL; a third resin comprising a hydrophobic resin having an average bulk density of from about 0.75 g/mL to about 0.85 g/mL; or a fourth resin comprising a hydrophobic polystyrene-divinylbenzene adsorbent having a water content of from about 55% to about 65%.

Embodiment (85). The method of any one of embodiments (68)-(84), wherein the method increases the isolated yield of the first constituent relative to a method comprising: passing a first feedstock stream through a first chromatographic resin to form a first eluate having a higher ratio of the first constituent to the second constituent than in the first feedstock stream; passing the first eluate through a second chromatographic resin to form a second eluate having a higher ratio of the first constituent to the second constituent than in the first eluate, under otherwise identical conditions.

Embodiment (86). The method of any one of embodiments (68)-(85), further comprising regeneration of at least one of the first chromatographic resin, the second chromatographic resin, and the third chromatographic resin for subsequent separations.

Embodiment (87). The method of embodiment (86), wherein the regeneration comprises washing the chromatographic resin with a regeneration solution comprising less than 5 wt. % water.

Embodiment (88). The method of embodiment (87), wherein the regeneration solution comprises ethanol, acetone, or a combination thereof.

Embodiment (89). The method of any one of embodiments (84)-(88), wherein the same resin is the first resin comprising a modified activated carbon adsorbent having an average particle size range of from about 45 to about 1700 microns and having an iodine number greater than about 900.

Embodiment (90). The method of any one of embodiments (84)-(88), wherein the same resin is the second resin comprising a modified hydrophobic adsorbent comprising a styrene-divinylbenzene (DVB) resin having about 4% to about 8% crosslinking or a poly(methyl methacrylate) (PMMA) resin, an average particle size range of from about 25 microns to about 300 microns, an average bulk density of from about 0.4 g/mL to about 0.6 g/mL, an average surface area of from about 450 $m^2/g$ to about 550 $m^2/g$, and an average pore volume of from about 0.7 mL/g to about 0.9 mL/g.

Embodiment (91). The method of any one of embodiments (84)-(88), wherein the same resin is the third resin comprising a hydrophobic resin having an average particle diameter of from about 25 microns to about 300 microns, an average bulk density of from about 0.75 g/mL to about 0.85 g/mL, an average surface area of from about 450 $m^2/g$ to about 500 $m^2/g$, and an average pore volume of from about 0.7 mL/g to about 0.9 mL/g.

Embodiment (92). The method of any one of embodiments (84)-(88), wherein the hydrophobic resin of the third resin is a C18 resin.

Embodiment (93). The method of any one of embodiments (84)-(88), wherein the same resin is the fourth resin comprising a hydrophobic polystyrene-divinylbenzene adsorbent having an average particle diameter of from about 250 microns to about 600 microns, an average bulk density of from about 0.6 g/mL to about 0.9 g/mL, and a water content of from about 55% to about 65%.

The foregoing exemplary embodiments of the disclosure numbered 1-91 are non-limiting. Other exemplary embodiments are apparent from the entirety of the description herein. As will be apparent to those of skill in the art upon reading this disclosure, each of the individually numbered embodiments may be used or combined with any of the preceding or following individually numbered aspects.

EXAMPLES

The following examples are provided to illustrate the present disclosure. These examples are shown for illustrative purposes, and any disclosures embodied therein should not be limited thereto.

Example 1—Extraction of Cannabis Leaves with Ethanol

Figure 3:
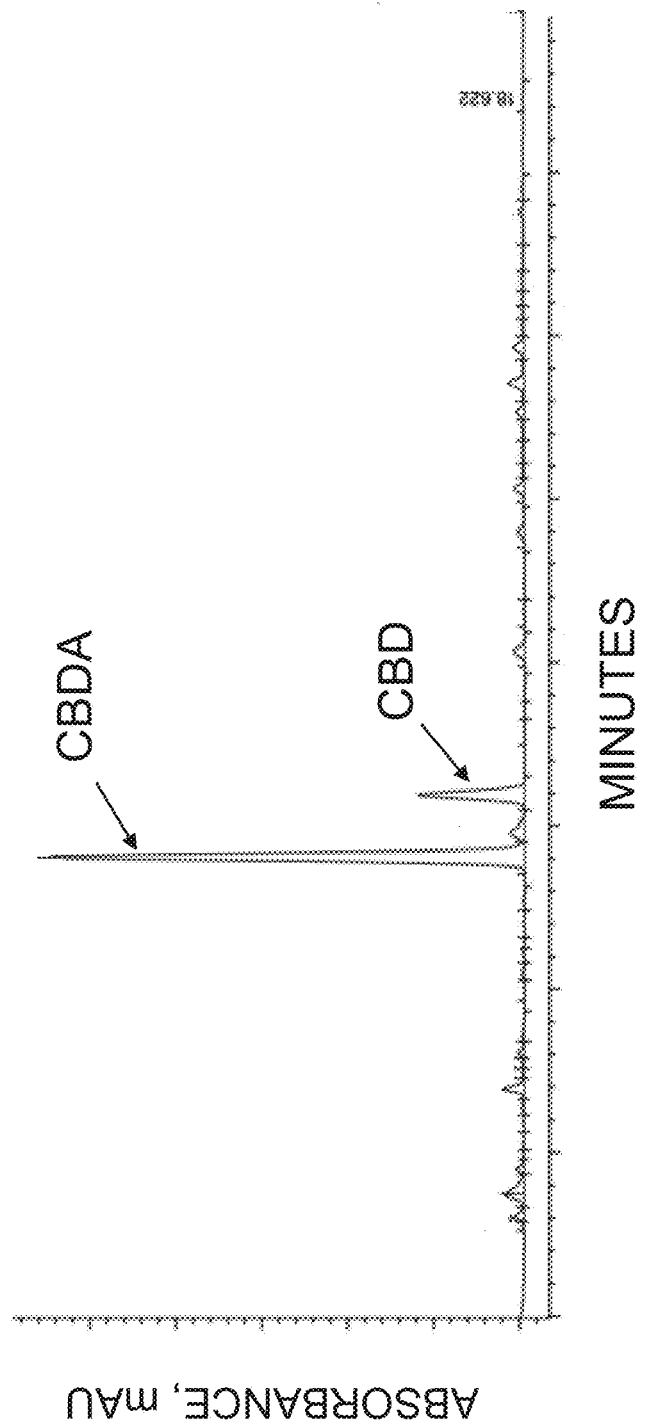
FIG. 3 is a High Performance Liquid Chromatography (HPLC) chromatographic area plot showing the results of a composition analysis of cannabinoids in the extract of dried hemp leaves.
Figure 8:
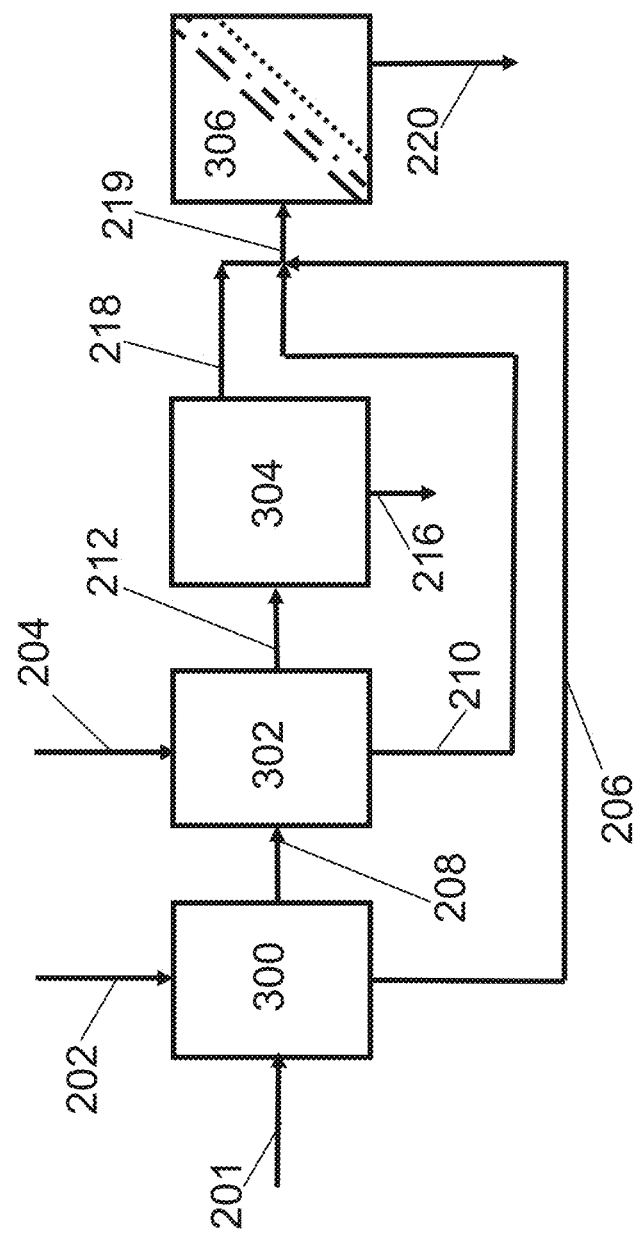
FIG. 8 is a schematic process flow diagram of the leaf extraction and filtration steps in one embodiment of the disclosure.

FIG. 8 is a schematic process flow diagram of the leaf extraction and filtration steps of embodiments of the disclosure. With reference to FIG. 8, about 150 Kg of dried cannabis leaves, shown in 201, was added to a 1000 Liter tote 300 and about 600 Liters of food grade ethanol (200 proof) was introduced to the tote 300 via line 202 to create a leaf/solvent mixture. The leaf/solvent mixture was agitated using a pneumatic mixer for a period of two hours at room temperature of about 25° C. at atmospheric pressure and allowed to stand overnight for an effective time (about 8 to 12 hours) to form a first ethanol layer. The first ethanol layer over the wet leaves was removed as a first decant stream in line 206. Shown as a second extraction step in tote 302, which may physically be the same as tote 300. A second portion of ethanol comprising 400 Liters of food grade ethanol was introduced via line 204 and again the leaf/solvent mixture was agitated in a second mixing step using a pneumatic mixer for a period of two hours at room temperature of about 25° C. at atmospheric pressure in a second extraction step. At the conclusion of the second mixing step, a second decant stream in line 210 was withdrawn and the remaining wet leaves were passed to a screw type extraction press (VINCENT Model CP10 available from Vincent Corporation, Tampa, Fla.) wherein the solids were pressed or squeezed, resulting in a third liquid decant stream in line 218 and used or spent leaves. The used or spend leaves shown as stream 216 are withdrawn and passed to waste disposal. The first, second and third decant streams (206, 210 and 218) were combined and passed to a filtration zone 306 as a liquid leaf extract stream in line 219. Following extraction the solid concentration of the liquid leaf extract stream comprised of 35-40% cannabidiol and cannabidiolic acid. The solid concentration of total solids (as measured following evaporation of the solvent from the liquid leaf extract stream) in the liquid leaf extract stream was approximately 25-30 g/L. The liquid leaf extract stream or crude cannabis extract stream was decanted and filtered in the filtration zone 306 to remove solid particles, by passing the liquid leaf extract stream through three successive filters of decreasing pore size: 100 micron, 20 micron, and 10 micron. The 100 micron pore size filter comprised a bag made of felt for high capacity flow and capturing solids. The 20 and 10 micron pore size filters were cartridges comprising polyethylene and were pleated for higher surface area. The cartridges had O-rings on a fitting at the end for seating inside a stainless steel cylindrical housing. The filtered liquid leaf extract stream was green in color, was essentially free of particles, and comprised approximately 20-40 g/L of cannabidiol (CBD) and cannabidiolic acid (CBDA). FIG. 3 illustrates a High Performance Liquid Chromatography (HPLC) chromatographic area plot showing the results of a composition analysis of cannabinoids in the filtered liquid extract stream. Table 5 shows the composition of the filtered liquid extract stream or filtered crude cannabinoid stream from the extract of industrial hemp leaves.

TABLE 5

Extracted Material from Industrial Hemp Leaves

| Compound | Amount Reported, wt. % |
|---|---|
| THC | 0.1 |
| THCV | 0.0 |
| CBG | 1.0 |
| CBD | 4.0 |
| CBN | 1.0 |
| THCA | 1.8 |
| CBDA | 25.0 |
| CBDV | 0.0 |
| Other | 67.1 |
| Total | 100.0 |

Example 2—Removal of Chlorophylls and Other Impurities

Figure 4:
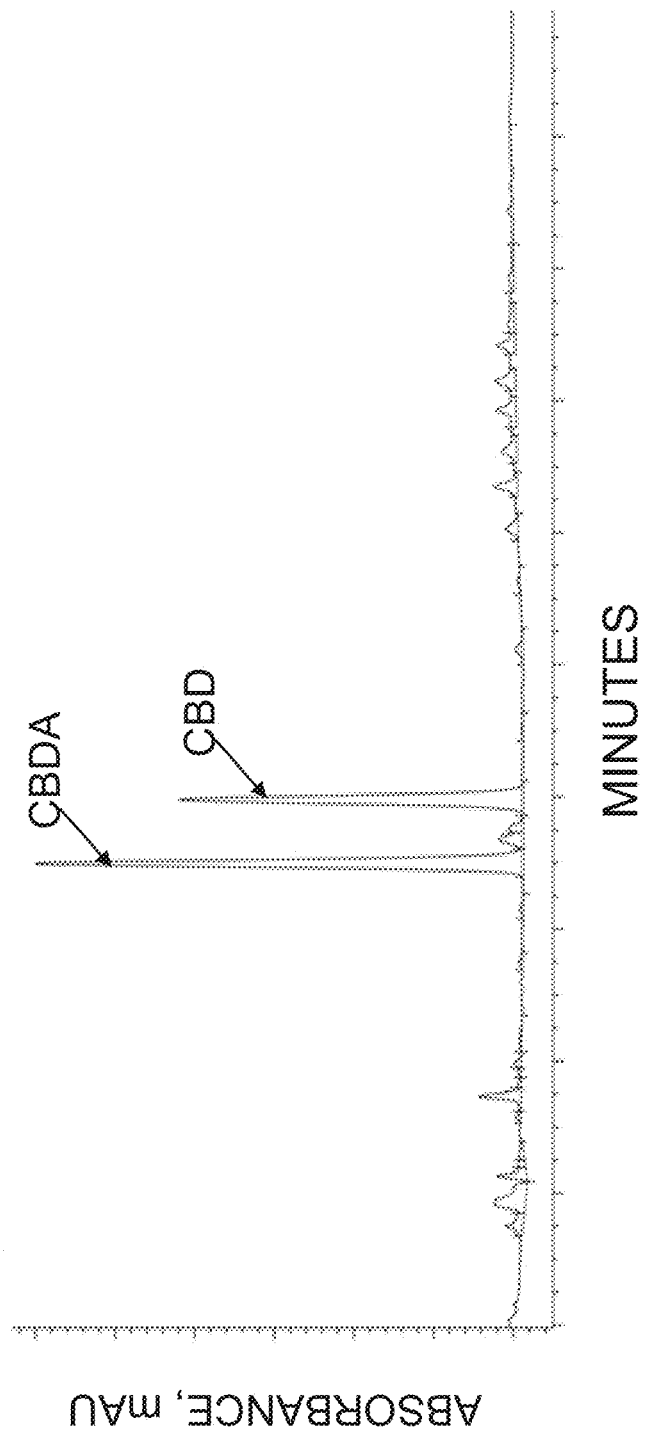
FIG. 4 is a High Performance Liquid Chromatography (HPLC) chromatographic area plot showing the results of a composition analysis of the cannabinoids in decolorized extract.

The green, filtered liquid extract stream, or filtered crude cannabinoid stream of Example 1 was loaded into a column chromatography zone to remove chlorophylls and other impurities. The filtered liquid leaf extract stream was passed through a 10 um filter to the top of a decolorization chromatographic column. The decolorization chromatographic column was comprised of polypropylene, having an inside diameter of 60 cm and a length of 183 cm (24 inches by 72 inches) and having an internal volume of 450 L (119 gal). The column was operated at a decolorization pressure of 2.72 atm to about 4.08 atm (40-60 psig) and a decolorization temperature ranging from 20-25° C. The flow rate used for the decolorization chromatographic column was between 2-3 L/min. The decolorization chromatographic column was packed with OR1 adsorbent. OR1 is a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. Essentially all chlorophylls were removed from the filtered liquid extract stream, and the resulting concentration of the solids in the extract stream was about 40-45% cannabidiol (CBD) and cannabidiolic acid (CBDA) and the concentration of total solids in the stream was approximately 20-35 g/L concentration. An HPLC trace of cannabinoids present within decolorized hemp leaf extract, or decolorized crude extract stream is shown in FIG. 4. In FIG. 4, the cannabidiol (CBD) and cannabidiolic acid (CBDA) composition peaks are essentially unchanged from FIG. 3. Thus, no chemical change occurred during the decolorization process, however the color observed in the resulting decolorized extract stream changed from green to amber. Table 6 shows the composition of the decolorized extract stream.

TABLE 6

Composition of Decolorized Extract Stream

| Compound | Amount Reported, wt. % |
|---|---|
| THC | 0.11 |
| THCV | 0.0 |
| CBG | 1.1 |
| CBD | 4.4 |
| CBN | 1.1 |
| THCA | 1.98 |

TABLE 6-continued

Composition of Decolorized Extract Stream

| Compound | Amount Reported, wt. % |
|---|---|
| CBDA | 35.0 |
| CBDV | 0.0 |
| Other | 63.81 |
| Total | 100.00 |

Example 3—Activation or Conversion of CBDA in to CBD and THCA into THC

Figure 5:
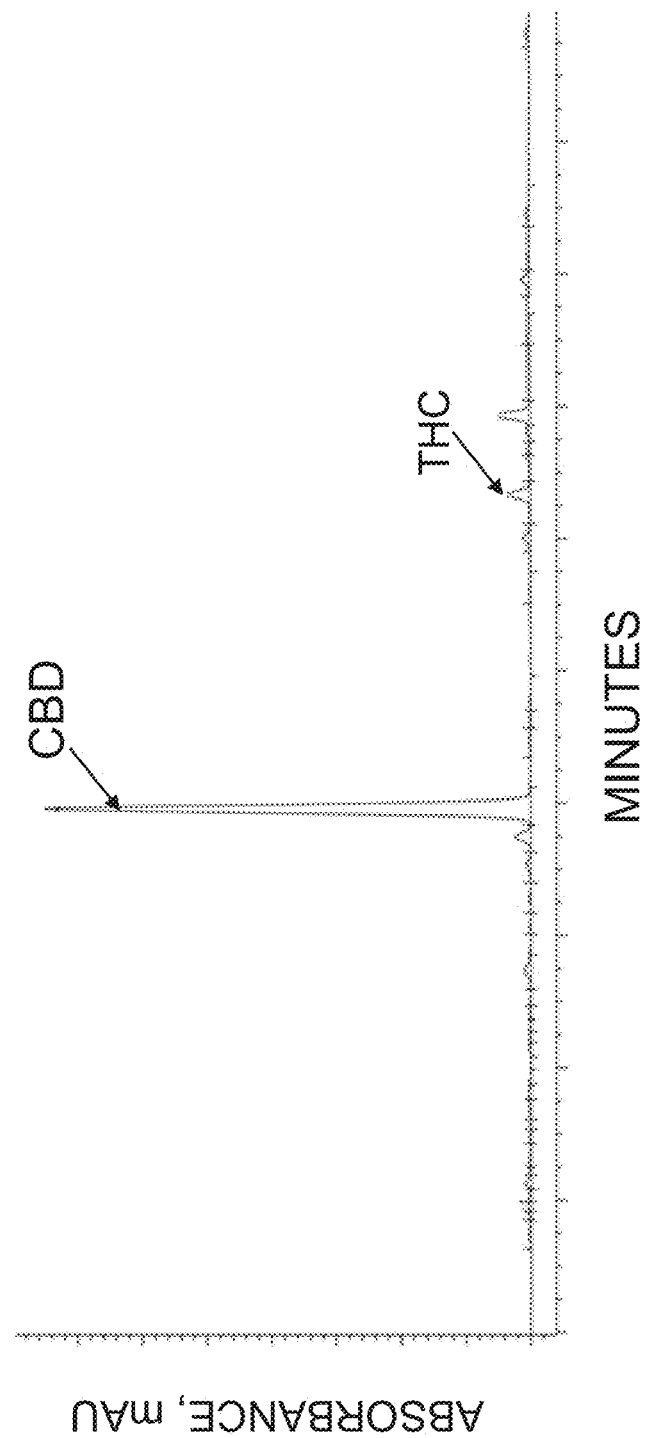
FIG. 5 is a High Performance Liquid Chromatography (HPLC) chromatographic area plot showing the results of a composition analysis of cannabinoids in activated extract.

The decolorized hemp leaf extract stream prepared in Example 2 was passed to a vacuum distillation unit, to remove essentially all of the solvent from the mixture. The vacuum distillation condenser had a 240 L capacity. This unit was operated at a vacuum pressure of −0.602 to −0.735 atm (−18 to −22 in Hg) and a temperature of 90-110° C. At least a portion of ethanol solvent recovered from the vacuum distillation unit was reused as solvent for the hemp leaf extraction step, described in Example 1. Following removal of the solvent, the resulting oil was retained in the vacuum distillation vessel at a decarboxylation temperature of 90 to 120° C. and a decarboxylation pressure of about −0.6 to 0.74 atm for an additional 5 to 8 hours, to permit sufficient time for the decarboxylation reaction to occur. The decarboxylation reaction time was sufficient to fully decarboxylate essentially all of the acidic components to provide a decarboxylated hemp oil. During the course of the decarboxylation reaction it was observed that some of the impurities in the feed were aggregated into a sludge like material which floated on top of the decarboxylated hemp oil. The aggregated impurities were removed, by subjecting the decarboxylated hemp oil to a water wash step to solubilize the impurities and remove the impurities from the decarboxylated hemp oil. FIG. 5 is an HPLC trace of cannabinoids present within decarboxylated hemp oil. In FIG. 5. A CBD peak was observed, but there was no CBDA peak present. The absence of a CBDA peak showed that the decarboxylation reaction of CBDA to CBD has proceeded to completion. The THC peak appears more prominently in FIG. 5 than before, which indicates that any THCA, although present in very small amounts in the decarboxylated hemp oil, has also been converted to THC. Table 7 shows the composition of the activated or decarboxylated cannabinoid oil stream.

TABLE 7

Composition of Decarboxylated Cannabinoid Oil

| Compound | Amount Reported, wt. % |
|---|---|
| THC | 2.09 |
| THCV | 0.0 |
| CBG | 1.1 |
| CBD | 40.0 |
| CBN | 1.1 |
| THCA | 0.0 |
| CBDA | 0.0 |
| CBDV | 0.0 |
| Other | 55.41 |
| Total | 100.00 |

Example 4—Dewaxing and Impurity Removal from Decarboxylated Hemp Oil

Figure 6:
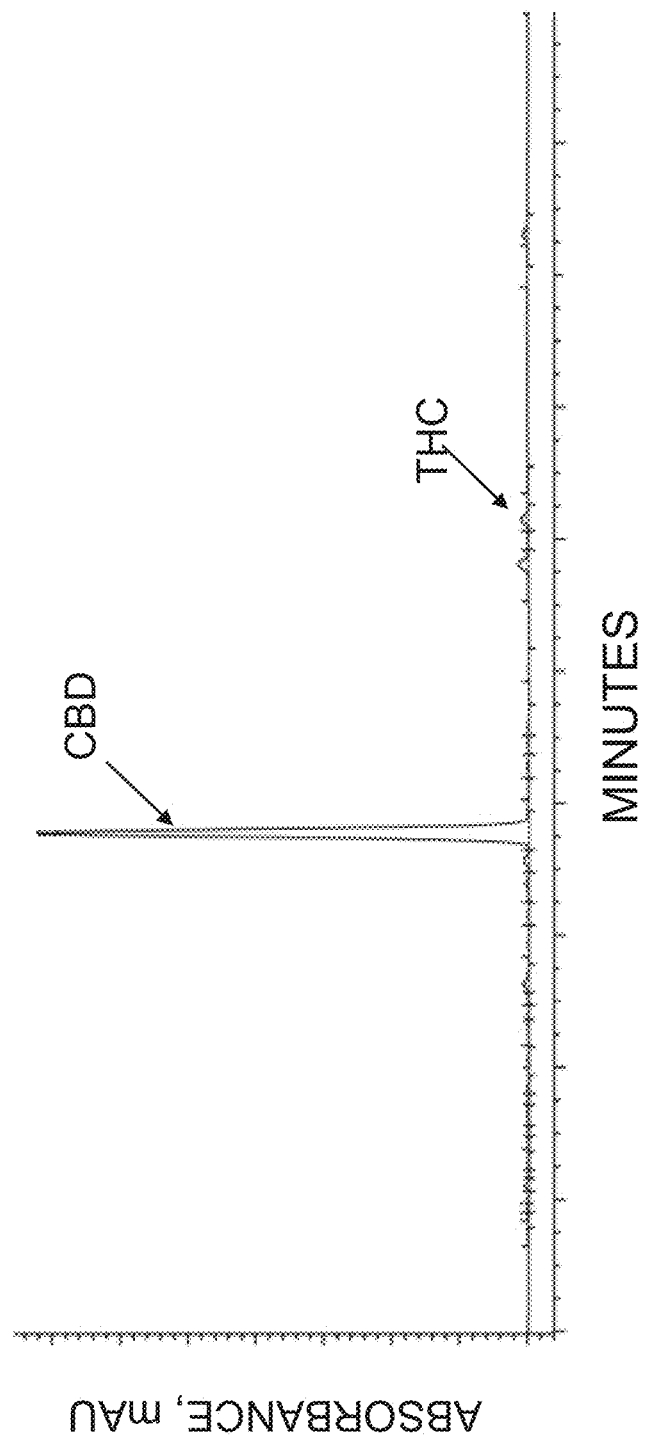
FIG. 6 is a High Performance Liquid Chromatography (HPLC) chromatographic area plot showing the results of a composition analysis of cannabinoids in dewaxed activated extract.

In the dewaxing zone, lipids and plant waxes were removed from the dewaxing feed stream. The decarboxylated hemp oil of Example 3 was reconstituted in a dewaxing solution containing ethanol and water in a volume ratio of 80/20 (Combine 800 cc of alcohol to 200 cc to prepare 1 Liter of dewaxing solvent) to provide a dewaxing feed stream having 40-45 g/L concentration of total solids. It was discovered that the concentration of solids in the dewaxing feed stream should not exceed 50 g/L of concentration. The dewaxing feed stream was passed to the top of a dewaxing column at a dewaxing flow rate of 2-3 L/min and a dewaxing column pressure of 2.72 to 4.08 atm (40-60 psi) and room temperature (20-25° C.). The dewaxing column was comprised of polypropylene, having an inside diameter of 60 cm and a length of 183 cm (24 inches by 72 inches) and having an internal volume of 450 L (119 gal). The dewaxing column was packed with OR1 adsorbent. OR1 is a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. The effluent from the dewaxing column, or dewaxed hemp oil stream had a concentration of total solids in the dewaxed hemp oil stream of from 35 to 40 g/L, and comprised of about 60 wt. % cannabidiol. FIG. 6 shows the cannabinoid makeup of the dewaxed hemp oil stream. In FIG. 6, the concentration of tetrahydrocannabinol (THC) is significantly reduced compared to the amount of THC in the decarboxylated hemp oil as shown in FIG. 5. Table 8 shows the composition of the dewaxed cannabidiol oil.

TABLE 8

Composition of Dewaxed Cannabidiol Oil

| Compound | Amount Reported, wt. % |
|---|---|
| THC | 2.0 |
| THCV | 0.0 |
| CBG | 1.1 |
| CBD | 55.0 |
| CBN | 1.1 |
| THCA | 0.0 |
| CBDA | 0.0 |
| CBDV | 0.0 |
| Other | 40.8 |
| Total | 100.0 |

Example 5—THC Removal and CBD Enrichment by SMB Process

The simulated moving bed (SMB) process step for the removal of THC from a mixture of THC and CBD in the dewaxed hemp oil stream was demonstrated in a specially configured eight-bed SMB system for reversed phase separation. A lab scale SMB unit (OCTAVE-300 unit, available from Semba Biosciences, Inc., Madison, Wis.) was used for the separation and was configured as shown in FIG. 2. The Semba Octave-300 Chromatography System is a bench top automated liquid chromatography platform designed for preparative-scale purification of chemical and biological compounds. According to FIG. 2, there were eight adsorption beds arranged in series and connected through a proprietary pneumatic valve array (not shown). The SMB scheme shown in FIG. 2 is a 2-3-2-1 arrangement, wherein 2 adsorbent beds (C-1, C-2) were operated in a desorption zone, 3 adsorbent beds (C-3, C-4, C-5) were operated in a rectification zone, 2 adsorbent beds (C-6, C-7) operated in an adsorption zone, and 1 adsorbent bed (C-8) is operated in a concentration zone for raffinate. The independently working and programmable 72-valve array contains no moving parts, occupies only 3 µl per valve, and responds within 100 ms. Fluid flow is controlled by four independent pumps. The valve switching and pump flow rates are controlled via the SembaPro Software. The eight adsorbent beds (C-1, C-2, C-3, C-3, C-4, C-5, C-6, C-7, and C-8) were cylinders of 304 stainless steel, each adsorbent bed having an inside column diameter of 22 mm and a column length of 300 mm, and each adsorbent bed contained about 51.3 grams of adsorbent OR2. OR2 was modified hydrophobic adsorbent comprising a styrene-divinylbenzene (DVB) resin having 4 to 8 percent crosslinking or a poly(methyl methacrylate) (PMMA) resin. The OR2 hydrophobic adsorbent had an average particle diameter of between 25 and 300 microns, an average bulk density (g/mL) of from 0.4 to 0.6, an average surface area ($m^2$/g) of from 450 to 550, and an average pore volume of from 0.70-0.90 (mL/g) The rotary valve system was operated on a cycle, wherein bed switching occurred at every 10-20 minute intervals. The eight adsorption beds were arranged in serial fluid communication such that fluid introduced at the top of any adsorbent bed n continued to the next highest adsorbent bed n+1 by passing the effluent from the bottom of adsorbent bed n to the top of adsorbent bed n+1. The adsorbent beds were operated in four zones, zone 1, zone 2, zone 3, and zone 4, whereby the SMB feedstock stream, or dewaxed hemp oil stream in line 40 was loaded on to zone 3 (C-6) by introducing the SMB feedstock stream via lines 40 and 28 to adsorbent bed C-6. In zone 3, CBD was selectively adsorbed in adsorbent beds C-6 and C-7, and a primary raffinate stream was withdrawn in lines 32 and 36 from adsorbent bed C-7. At least a portion of the primary raffinate steam in line 32 was passed to zone 4 comprising adsorbent bed C-8 in line 34 and a secondary raffinate stream was withdrawn from adsorbent bed C-8 in line 38. The secondary raffinate comprised essentially no CBD or THC oils and was directly returned to zone 1 to offset the amount of the mobile phase desorbent in line 10. The flow rate of the secondary raffinate was about 2 wt. % of the flow rate of the primary raffinate. In the same step, a polar mobile phase desorbent in line 10, comprising an 80:20 volume mixture of ethanol and water, was simultaneously introduced to zone 1, comprising adsorbent beds C-1 and C-2, via lines 12 and 14, respectively. The mobile phase was passed through zone 1 in parallel through adsorbent beds C-1 and C-2, and the effluent of adsorbent beds C-1 and C-2 was withdrawn in lines 16 and 18, respectively, and combined to form an SMB extract stream in line 20. A portion of the SMB extract stream in line 22 was passed to zone 2 (comprising adsorbent beds C-3, C-4, and C-5) and introduced to the top of adsorbent bed C-3, and continuing serially through adsorbent beds C-3, C-4, and C-5 via lines 24, and 26, respectively. The effluent withdrawn from the bottom of adsorbent bed C-5 was passed to the top of adsorbent bed C-6 in line 27, and admixed with the SMB feedstock stream in line 40 before being passed to adsorbent bed C-6 in line 28. At the completion of each SMB cycle, the adsorbent beds was advanced to move countercurrent to the SMB feedstock, whereby adsorbent bed C-2 shifts to the left to the position previously occupied by C-1 and C-1 was shifted to the position previously occupied by adsorbent bed C-8.

SMB Feed

The decarboxylated hemp oil stream of Example 4 was admixed with an 80:20 mixture of water and food grade ethanol to provide an SMB feedstock stream having 40-60 w/w % CBD purity and 0.4-1.0 w/w % THC purity. The SMB feedstock stream was passed at an average SMB flow rate of 0.15-0.30 L/min to a guard column of 304 stainless steel. The guard column was cylindrical and had an inside column diameter of 15 cm (6 inch) and a column length of 90 cm (36 inches). The guard column was packed with OR2 adsorbent. OR2 is modified hydrophobic adsorbent comprising a styrene-divinylbenzene (DVB) resin having 4 to 8 percent crosslinking or a poly(methyl methacrylate) (PMMA) resin. The OR2 hydrophobic adsorbent has an average particle diameter of between 25 and 300 microns, an average bulk density (g/mL) of from 0.4 to 0.6, an average surface area ($m^2$/g) of from 450 to 550, and an average pore volume of from 0.70-0.90 (mL/g). The guard column provides some additional color removal and also removes any particulates from the SMB feedstock prior introducing the SMB feedstock to the SMB zone. The guard column was cleaned and regenerated regularly, about every 1 to 2 weeks. After being passed through a guard column, and with reference to FIG. 2, the SMB feedstock in line 40 was passed to the top of adsorbent bed C-6 via lines 40 and 28.

Mobile Phase Desorbent

The mobile phase desorbent used in the SMB zone was a mixture of ethanol in water. The ethanol was Food Grade Ethanol (Proof 200) and the water was deionized water. The mobile phase desorbent comprised a ratio of ethanol:water of 80:20 volume/volume. The mobile phase desorbent, with reference to FIG. 2, in line 10 passed to the tops of adsorbent beds C-1 and C-2 at a desorbent rate 2.0-3.0 L/min.

Stationary Phase

The stationary phase adsorbent in the SMB zone was OR2. OR2 is modified hydrophobic adsorbent comprising a styrene-divinylbenzene (DVB) resin having 4 to 8 percent crosslinking or a poly(methyl methacrylate) (PMMA) resin. The OR2 hydrophobic adsorbent had an average particle diameter of between 25 and 300 microns, an average bulk density (g/mL) of from 0.4 to 0.6, an average surface area ($m^2$/g) of from 450 to 550, and an average pore volume of from 0.70-0.90 (mL/g)

Process Parameters

The operating parameters of the SMB zone are shown in Table 9

TABLE 9

-SMB Operating Parameters-

| PARAMETER | VALUE | UNIT |
|---|---|---|
| Step Time | 10-20 | Minutes |
| Temperature | 20-25 | ° C. |
| Feed Rate (line 40)* | 0.23-0.50 | L/Min |
| Desorbent (line 12) | 1.27-2.0 | L/Min |
| Desorbent (line 14) | 1.27-2.0 | L/Min |
| Zone 2 Return (line 22) | 0.92-1.50 | L/Min |
| Extract (line 16) | 1.27-2.0 | L/Min |
| Extract (line 18) | 1.27-2.0 | L/Min |
| Primary Raffinate (line 36) | 0.99-1.50 | L/Min |
| Secondary Raffinate (line 38) | 0.16-0.25 | L/Min |

*Line numbers refer to FIG. 2

Figure 7:
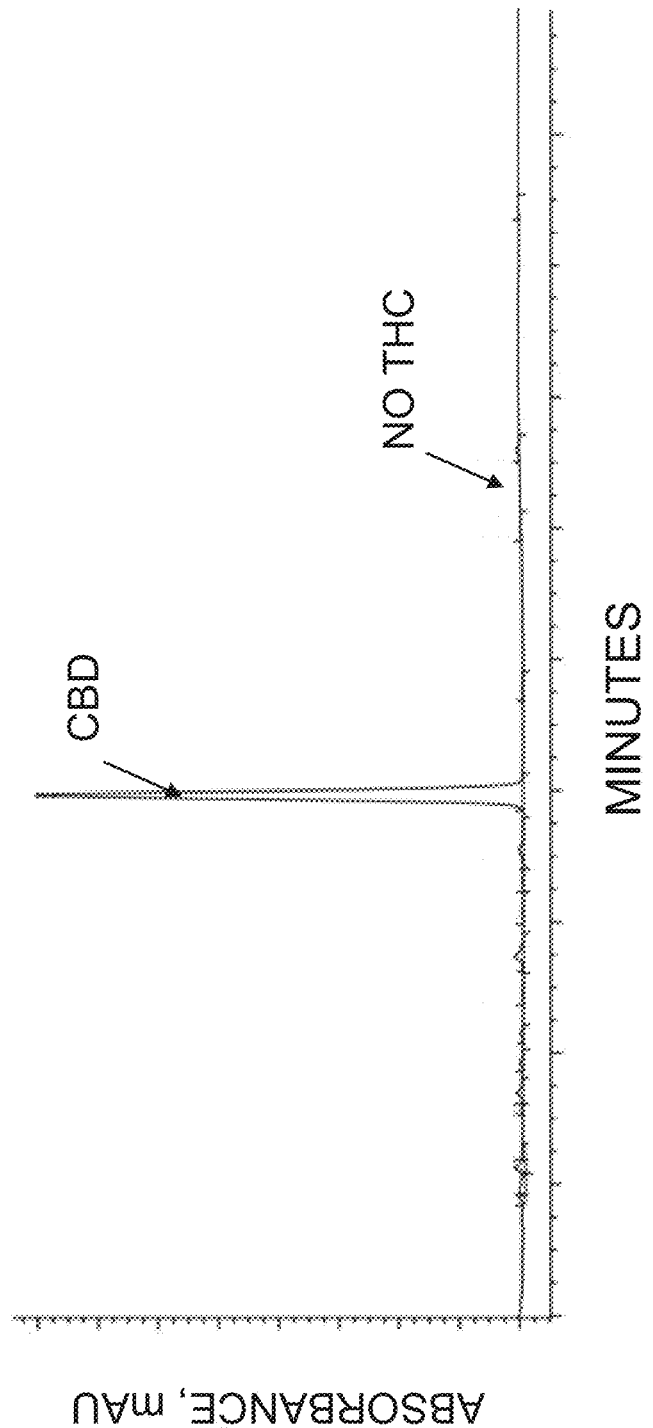
FIG. 7 is a High Performance Liquid Chromatography (HPLC) chromatographic area plot showing the results of a composition analysis of cannabinoids in polished activated extract.

The primary raffinate, withdrawn in line 36 was withdrawn at an average flow rate of 1.0-3.0 L/min. The primary raffinate had with an average concentration of solids of 5.0-7.0 g/L and an average CBD purity of 80-87% w/w and an average THC purity of 0.0% w/w. The primary raffinate was passed to an evaporation zone to recover the solvent and, following evaporation of the primary raffinate to dryness provides a THC free CBD oil stream which is essentially free of THC. FIG. 7 is an HPLC trace of the THC free CBD oil stream which shows the presence of CBD and the absence of any THC. The extract stream, withdrawn in line 20 was withdrawn at a rate of 1.0-2.0 g/L and comprised an average cannabinoid CBD purity of 35-40 w/w % and an average THC purity of 15-24 w/w %. A portion of the extract was passed to the top of zone 2 (C-3) at a rate of 1.0-2.0 L/min.

In a representative example of the SMB process described hereinabove, with a mobile phase desorbent comprising 80 vol. % ethanol:20 vol. % water; and an SMB feed rate of 11.66 Kgs per day of dewaxed cannabidiol oil having 55.0 wt. % CBD and 2.0 wt. % THC (See Table 8, hereinabove) the primary raffinate stream was withdrawn at a rate of 9.3 Kgs per day and comprised 65.0 wt. % CBD and 0.0 wt. % THC; the extract stream was withdrawn at a rate of 2.3 Kgs per day and comprised 14.35 wt. % CBD and 10.12 wt. % THC; and, the secondary raffinate was withdrawn at a rate of 0.098 Kgs per day and comprised 39.0 wt. % CBD and 0.30 wt. % THC. All of the above percentages were expressed on a solvent free basis. The compositions of the primary raffinate stream, the secondary raffinate stream and the extract stream were determined on a solvent free basis. The unreported portion of these streams was considered to be other cannabinoids. The primary raffinate composition following solvent removal is shown in Table 10.

TABLE 10

Composition of Primary Raffinate (Solvent Free Basis)

| Compound | Amount Reported, wt. % |
|---|---|
| THC | 0.00 |
| THCV | 0.0 |
| CBG | 0.1 |
| CBD | 65.0 |
| CBN | 0.1 |
| THCA | 0.0 |
| CBDA | 0.0 |
| CBDV | 0.0 |
| Other | 34.8 |
| Total | 100.0 |

Example 6—Polishing Step

In a polishing step, the dewaxed hemp oil stream of Example 4, wherein the lipids and plant waxes were removed, was passed to a polishing chromatography column. The polishing chromatographic column was comprised of polypropylene, having an inside diameter of 60 cm and a length of 183 cm (24 inches by 72 inches) and having an internal volume of 450 L (119 gal). The column was operated at a polishing pressure of 2.72 atm to about 4.08 atm (40-60 psig) and a polishing temperature ranging from 20-25° C. The flow rate used for the polishing chromatographic column was between 2-3 L/min. The polishing chromatographic column was packed with OR1 adsorbent. OR1 was a modified activated carbon adsorbent which was heat treated to provide a highly hydrophobic adsorbent which is essentially free of hydroxyl groups, and has an average particle diameter of between 177 and 250 microns, and an iodine number (a measure of the micropore content of the activated carbon) of above 900 mg/g. Dewaxed extract was passed to the polishing chromatography column and the eluent stream was observed for the breakthrough of tetrahydrocannabinol (THC). Once THC breakthrough was observed using high performance liquid chromatography (HPLC), the passing of the dewaxed hemp oil stream was discontinued, and the effluent of the polishing chromatography column was collected to provide a CBD polished oil stream. The CBD polished oil stream withdrawn from the polishing chromatography column comprised no THC and comprised a cannabidiol (CBD) concentration of about 70-75% on a solvent free, dry weight basis. The concentration of total solids in the effluent of the polishing chromatography column was about 15-30 g/L. Like the THC free CBD oil stream from the SMB zone, an HPLC chromatogram of the showed no peak for THC. An HPLC analysis of the effluent of the polishing chromatography column showed a large quantity of CBD was present, thus indicating that the majority of the sample was CBD. There were also other terpenes and minor cannabinoids present in the oil that were not THC or CBD.

Example 7—CBD Enrichment by Removing Polar Compounds

The CBD polished oil stream of Example 6 was further processed to remove polar impurities. Although, after the polishing step, the purity of CBD in the material is already high, this step increased the CBD purity by another 5-10% in the CBD polished oil stream, resulting in 80-85% CBD purity. The CBD polished oil stream was passed to a first evaporation zone wherein the solvent was evaporated. The product stream was passed to a vacuum distillation vessel which was operated at a first evaporation zone temperature of about 80-100° C. and a first evaporation zone pressure of −0.53 to −0.67 atm (−16 to −20 in Hg). Following evaporation of the solvent, the remaining oil portion was re-dissolved to provide a non-polar solution using hexane as a non-polar solvent. In normal operation, about 30 Kg of the remaining oil portion from the evaporated CBD polished oil stream was added to 100 L of hexane. The normal yield of polished CBD oil was about 90-95 wt. % of the polished oil material passed to the first evaporation zone. The purity of the polished CBD oil after removal of the polar impurities generally increased by about 5 wt. %). Table 11 shows the effect of the polishing step on the CBD oil.

TABLE 11

Effect of Polishing Step on CBD Oil Purity

| | Starting material | Resulting material in solution |
|---|---|---|
| Weight | 30 Kg | 27-28 Kg |
| Hexane Volume | 0 L | 100 L |
| CBD Purity | 75-80% | 80-85% |

The solution was prepared at a concentration of 10-30% by weight. The solution was agitated and allowed to rest at room temperature for a period of 120 to 720 minutes to allow the polar compounds to settle out. The supernatant hexane solution was decanted to remove solution comprising the CBD oil from the solid polar compounds that had precipitated.

Example 8—Preparation of Phytocannabinoid Rich Oil

The supernatant hexane solution of Example 7 was passed to a second evaporation zone to remove all of the polar solvent, hexane. The second evaporation zone used a rotary evaporator operating at a second evaporator temperature of about 35-45° C., a second evaporator pressure of about 0 to about −0.0148 atm (0-15 mbar vacuum), for a second evaporator time of about 2-3 hours). The polar solvent, hexane, was evaporated and an evaporated CBD oil was recovered. The evaporated CBD oil was washed with ethanol, three times using an ethanol wash stream comprising food grade ethanol in washing ratio of 1:3 Liters of ethanol to Kg of oil ratio for each wash. After the ethanol wash, the oil was washed in a water wash step with water using a water wash ratio of 1:3 Liters of water to Kg of oil. Washes were carried out inside the flask of the rotary evaporator and the resulting solutions were evaporated to complete dryness after each wash to provide a THC free Phytocannabinoid rich oil product. The resultant THC free Phytocannabinoid rich oil is described in Tables 12 and 13, where Table 12 describes the range of composition of the cannabinoids in the Phytocannabinoid Rich Oil, and Table 13 describes the residual solvent analysis in the Phytocannabinoid Rich Oil. No detectable solvent was found to present in the THC free Phytocannabinoid rich oil product as described in Table 13.

TABLE 12

THC free Cannabinoid profile of Phytocannabinoid Rich Oil

| Compound | Amount reported % |
|---|---|
| THC | 0 |
| THCV | 0 |
| CBG | 0-4% |
| CBD | 70-86% |
| CBN | 0-3% |
| THCA | 0 |
| CBDA | 0 |
| CBDV | 0-1% |
| Other | 30-10% |

TABLE 13

Residual Solvent Analysis of THC free Phytocannabinoid Rich Oil

| Solvent | Amount Reported |
|---|---|
| Ethanol | ND |
| Isopropanol | ND |
| Hexane | ND |
| Ethyl Acetate | ND |
| Heptane | ND |

ND—None-Detected

Example 9—Preparation of CBD Isolate

The supernatant hexane solution of Example 7 can also be processed to provide a CBD isolate product. The CBD isolate product was prepared by passing the supernate hexane solution to an isolate chromatography zone comprising two isolate chromatographic columns connected in serial fluid communication. Each chromatographic column was filled with a selective adsorbent. The adsorbent in the first chromatographic column was OR3, and the adsorbent in the second chromatographic column was OR4, and the total mass of adsorbent in both the first and the second chromatographic columns determined the total amount of supernatant hexane solution which could be loaded. The two adsorbents OR3 and OR4 are described hereinabove. The amount of supernatant hexane solution passed to the isolate chromatography zone was determined by the amount of CBD material in the supernatant solution and the total mass of the two adsorbents; that is, 12-16 Kg of CBD material per Kilogram of the total mass of the two adsorbents (OR3 and OR4) of the supernatant hexane solution was passed a first of two isolate chromatographic columns. As supernatant hexane solution was passed to the columns the resulting isolate elute solution was collected. The resulting isolate elute solution, comprised about 20-30% of CBD oil by weight. The resulting isolate elute solution was placed into stainless steel receptacles and placed inside a freezer at a freezer temperature of −20° C. for a freezer period of 24-72 hours. In the freezer, at the freezer temperature was maintained below about −20° C., and high purity CBD crystals, containing 96-98% CBD by weight were formed. The high purity CBD crystals were harvested and re-dissolved into a crystal isolate solution with hexane and comprising 20-30% by weight CBD oils. The crystal isolate solution was placed into stainless steel receptacles and allowed to stand at about room temperature for a period of 24-72 hours. High purity CBD crystals formed, comprising about 99% CBD by weight. These high purity CBD crystals were harvested and placed inside of a flask of a rotary evaporator. The crystals were heated until molten, and the residual hexane was evaporated. The high purity CBD crystals typically melted at about 70° C., although the crystal melting point varied depending upon the vacuum pressure in the flask of the rotary evaporator. Following evaporation of the hexane from the high purity CBD crystals, a water wash, using 200 g of water for every 1 Kg of crystals to be washed, was carried out in the evaporator flask of the rotary evaporator. Following the water wash, the evaporation continued until any remaining water was removed by evaporation to complete dryness; and, the CBD isolate was allowed to solidify. The solidification temperature was about 37° C. The solidified CBD isolate was harvested and crushed into powder to provide a powdered CBD isolate. The resulting powdered CBD isolate is described herein below in Tables 14 and 15. Table 14 describes the CBD purity of the isolate, while Table 15 describes the residual solvent analysis of the CBD isolate powder.

TABLE 14

Cannabinoid Profile Of Isolates

| Compound | Amount Reported, wt. % |
|---|---|
| THC | 0 |
| THCV | 0 |
| CBG | 0 |
| CBD | 99.7 |
| CBN | 0 |
| THCA | 0 |
| CBDA | 0 |
| CBDV | 0 |
| Other | 0.3 |
| Total | 100.0 |

TABLE 15

Residual Solvent Analysis of CBD Isolates

| Solvent | Amount Reported |
|---|---|
| Ethanol | ND |
| Isopropanol | ND |

TABLE 15-continued

Residual Solvent Analysis of CBD Isolates

| Solvent | Amount Reported |
| --- | --- |
| Hexane | ND |
| Ethyl Acetate | ND |
| Heptane | ND |

Example 10—OR-1 Single Column for THCA Removal

Figure 14:
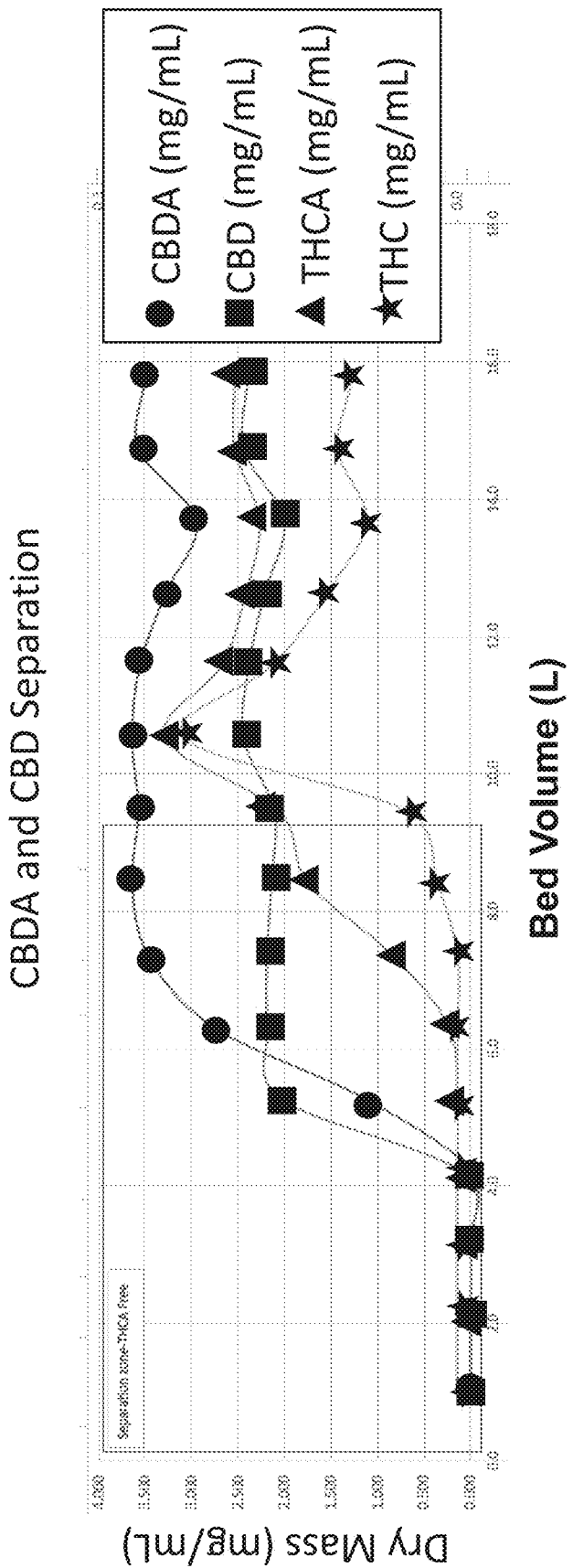
FIG. 14 is a graph showing the separation zone between CBDA/CBD and THCA in an OR-1 single column in Example 10.

The hemp extract of Example 1 can be used as feed to purify CBDA and CBD by removal of THCA and THC using OR-1 adsorbent in a single column. In a lab scale run, 18 mg of hemp extract was dissolved for every mL of solvent (95/5 v/v Ethanol/Heptane, from Pharmco-Aaper). The column, measuring 22 mm diameter and 300 mm in length, was connected to a single pump (SSI, 0-100 mL). The flow rate was set to 4.0 mL per minute and the system was maintained at 25° C. The graph in FIG. 14 shows the separation zone between CBDA/CBD and THC/THCA in OR-1 single column chromatography. As is apparent from FIG. 14, OR-1 single column chromatography provides separation of CBDA and CBD from THC and THCA.

Example 11—OR-5 Single Column for THCA Removal

Figure 15:
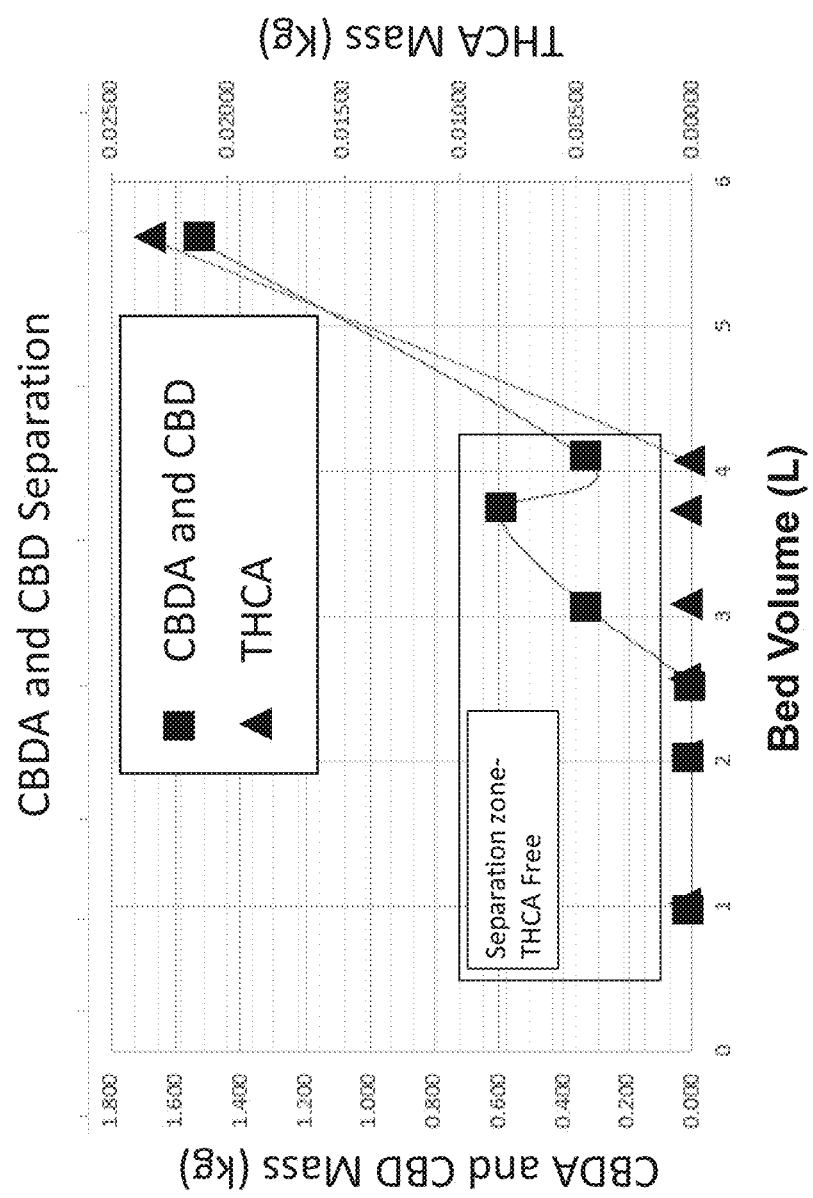
FIG. 15 is a graph showing the separation zone between CBDA+CBD and THCA in an OR-5 single column chromatography in Example 11.

The decolorized hemp extract of Example 2 can be used as feed to purify CBDA and CBD and to remove THCA and THC using OR-5 as adsorbent in a single column. In a pilot scale run, 17.6 mg of decolorized extract was dissolved for every mL of solvent (95/5 v/v Ethanol/Heptane, from Pharmco-Aaper). The column, measuring 20 in. in diameter and 48 in. in length, was connected to a single pump (Tuthill, 0-4 L/min). The flow rate was set to 1.0 L per minute and the system was maintained at 25° C. The graph in FIG. 15 shows the separation zone between CBDA+CBD and THCA in OR-5 single column chromatography. As is apparent from FIG. 15, OR-5 single column chromatography provides separation of CBDA and CBD from THCA.

Example 12—OR-5 Single Column for THC Removal

The decolorized and decarboxylated hemp extract of Example 3 can be used as feed to purify CBD by removing THC using OR-5 as adsorbent in a single column. In the pilot scale run, 66.8 mg of decolorized extract was dissolved for every mL of solvent (95/5 v/v Ethanol/Heptane, from Pharmco-Aaper). The column, measuring 20 in. in diameter and 48 in. in length, was connected to a single pump (Tuthill, 0-4 L/min). The flow rate was set to 1.0 L per minute and the system was maintained at 25° C. The data in Table 16 show the mass of CBD and THC that was loaded on the single OR-5 column, and the mass of CBD and THC that was collected in the effluent from the single OR-5 column.

TABLE 16

Recovery of CBD and THC After OR-5 Single Column Chromatography

| Stream | Total Mass (kg) | CBD Mass (kg) | THC Mass (kg) |
| --- | --- | --- | --- |
| Decolorized and Decarboxylated feed | 28.39 | 19.526 | 0.48 |
| Effluent collected | 14.365 | 5.38 | 0.096 |

As is apparent from the results set forth in Table 16, the relative ratio of CBD to THC has increased, demonstrating the OR-5 provides separation of CBD from THC.

Example 13—OR-5 Single Column with Ethanol Wash for CBDA+CBD Recovery

Figure 16:
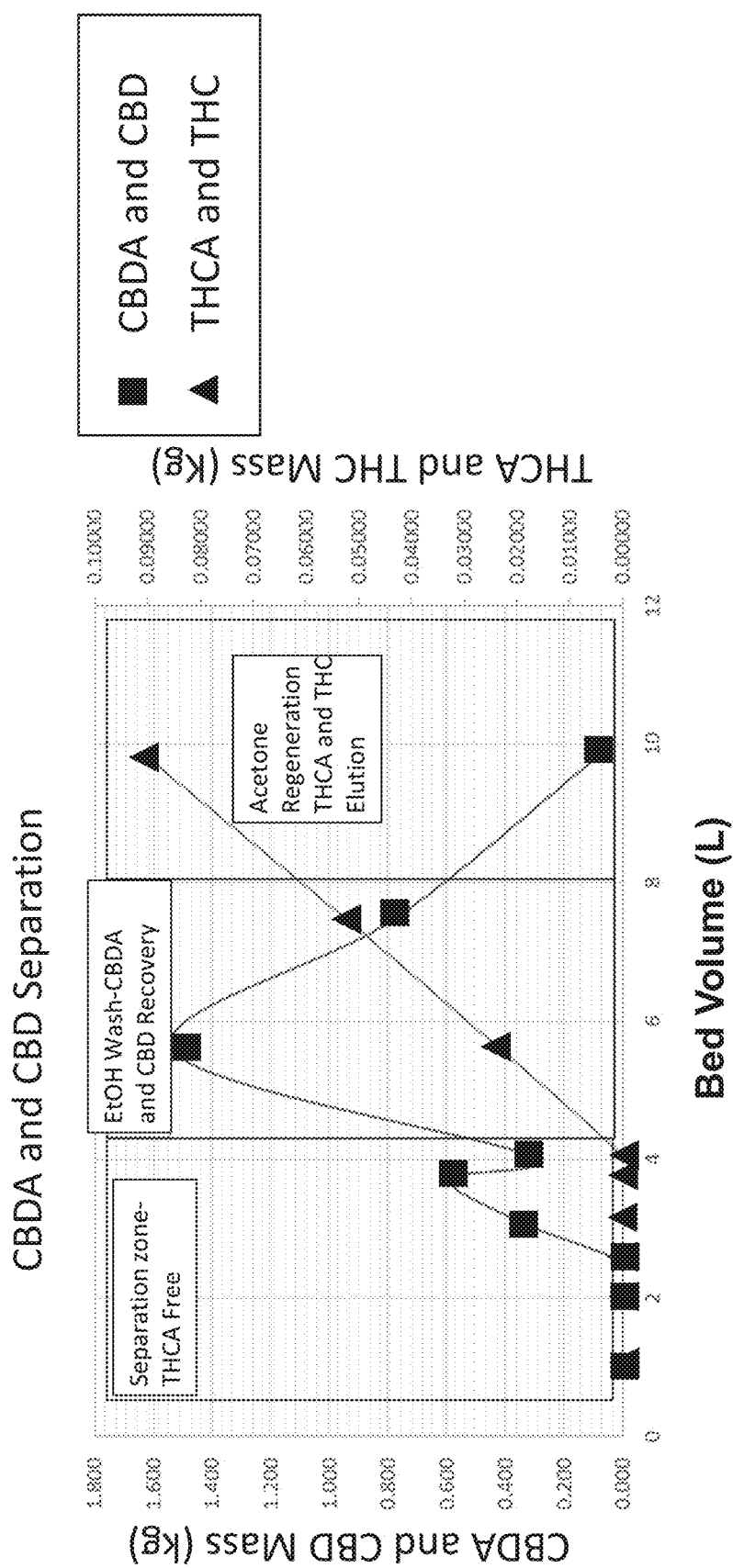
FIG. 16 is a graph showing the recovery of CBDA+CBD after chromatography on an OR-5 single column with an ethanol wash, followed by acetone regeneration in Example 13.

The decolorized hemp extract of Example 2 can be used as feed to purify CBDA and CBD and to remove THCA & THC using OR-5 as adsorbent in a single column. To improve recovery for CBDA+CBD from the single column, an ethanol wash can be conducted. In the pilot scale run, 17.6 mg of decolorized extract was dissolved for every mL of solvent (95/5 v/v Ethanol/Heptane, from Pharmco-Aaper). The column, measuring 20 in. in diameter and 48 in. in length, was connected to a single pump (Tuthill, 0-4 L/min). After loading the feed and collecting THCA-free product, an ethanol wash was conducted to recover the CBDA and CBD adsorbed on the single column. The graph in FIG. 16 shows the recovery of CBDA+CBD after chromatography on an OR-5 single column with an ethanol wash. As is apparent from FIG. 16, the OR-5 column provides separation of CBD and CBDA from THC. In addition, the OR-5 column can be washed with an ethanol wash to recover adsorbed CBDA and CBD.

Example 14—OR-5 Single Column Regeneration with Acetone Wash for THCA Elution The decolorized hemp extract of Example 2 can be used as feed to purify CBDA and CBD and to remove THCA & THC using OR-5 as adsorbent in a single column. To improve recovery for CBDA+CBD from the single column, an ethanol wash can be conducted. After recovering the CBDA+CBD, a wash with acetone can be used for the single column regeneration. In the pilot scale run, 17.6 mg of decolorized extract was dissolved for every mL of solvent (95/5 v/v Ethanol/Heptane, from Pharmco-Aaper). The column, measuring 20 in. in diameter and 48 in. in length, was connected to a single pump (Tuthill, 0-4 L/min). After loading the feed and collecting THCA-free product, an ethanol wash was used to recover the CBDA and CBD adsorbed on the single column. A wash with acetone was used for regeneration and THCA elution. The flow rate was set to 1.0 L per minute and the system was maintained at 25° C. The graph in FIG. 16 shows the separation zone between CBDA+CBD and THCA, followed by the acetone regeneration zone. As is apparent from FIG. 16, the OR-5 column provides separation of CBD and CBDA from THC. In addition, the OR-5 column can be regenerated with an acetone wash to recover any adsorbed THCA and THC.

Example 15—OR-5 SMB Technology for THC and THCA Removal

The decolorized hemp extract of Example 2 can be used as feed to purify CBDA and CBD, and to remove THCA &

THC, using SMB technology with OR-5 as the adsorbent. In the pilot scale run, 8.8 mg of decolorized extract was dissolved for every mL of solvent (95/5 v/v Ethanol/Heptane, from Pharmco-Aaper). Eight columns, each measuring 6 in. in diameter and 36 in. in length, were connected to the Simulated Moving Bed instrument (from Semba Bioscience—WI, USA). Four pumps (0-2.5 lpm) were also connected to the SMB Instrument. The SMB Step time was set at 1320 sec. and the system was maintained at 25° C. The flow rates for the above-mentioned streams are tabulated in Table 17, while the mass percent of each bulk stream is given in Table 18.

TABLE 17

Flow Rates for the Zones in SMB of Example 15

|  | Flow rate (L/min) |
|---|---|
| Desorbent (Zone 1 In) | 1.5 |
| Feed Extract In (Zone 2 In) | 0.8 |
| Intermediate Flow (Zone 3 In) | 0.8 |
| Primary Raffinate (Zone 3 Out) | 0.88 |
| Secondary Raffinate (Zone 4 Out) | 0.6 |

TABLE 18

Mass Percent in Each Bulk Stream in SMB of Example 15

| SMB Outputs | Mass Percent (%) | | | |
|---|---|---|---|---|
|  | CBDA | CBD | THCA | THC |
| Extract | 4.64 | 25.93 | 42.92 | 99.28 |
| Primary Raffinate | 95.09 | 74.07 | 53.18 | 0 |
| Secondary Raffinate | 0.26 | 0 | 3.9 | 0.72 |

As is apparent from the results set forth in Table 18, the majority of the CBDA and CBD is present in the primary raffinate, whereas the majority of the THC is found in the extract stream.

Example 16—OR-5 SMB Technology for THC Removal

The decolorized and decarboxylated hemp extract of Example 3 can be used as feed to purify CBD and to remove THC using SMB technology with OR-5 as the adsorbent. In the pilot scale run, 64.1 mg of decolorized and decarboxylated extract was dissolved for every mL of solvent (95/5 v/v Ethanol/Heptane, from Pharmco-Aaper). Eight columns, measuring 6 in. in diameter and 36 in. in length, were connected to the Simulated Moving Bed instrument (from Semba Bioscience—WI, USA). Four pumps (0-2.5 lpm from Tuthil) were also connected to the SMB Instrument. The columns were figured to run in a 2-3-2-1 scheme. The SMB Step time was set at 1210 sec and the system was maintained at 25° C. The flow rates for the above-mentioned streams are tabulated in Table 19, while the mass percent of each bulk stream is given in Table 20.

TABLE 19

Flow Rates for the Zones in SMB of Examples 16 and 17

|  | Flow rate (L/min) |
|---|---|
| Desorbent (Zone 1 In) | 1.2 |
| Feed | 0.41 |
| Extract In (Zone 2 In) | 1.05 |
| Intermediate Flow (Zone 3 In) | 1.05 |
| Primary Raffinate (Zone 3 Out) | 0.53 |
| Secondary Raffinate (Zone 4 Out) | 0.9 |

TABLE 20

Mass Percent in Each Bulk Stream in SMB of Example 16

| SMB Outputs | Mass Percent (%) | |
|---|---|---|
|  | CBD | THC |
| Extract | 2.88 | 23.60 |
| Primary Raffinate | 84.69 | 43.15 |
| Secondary Raffinate | 12.42 | 33.25 |

As is apparent from the results set forth in Table 20, the majority of the CBDA and CBD is present in the primary raffinate.

Example 17—OR-5 SMB Technology for Wax and Lipids Removal

Figure 17:
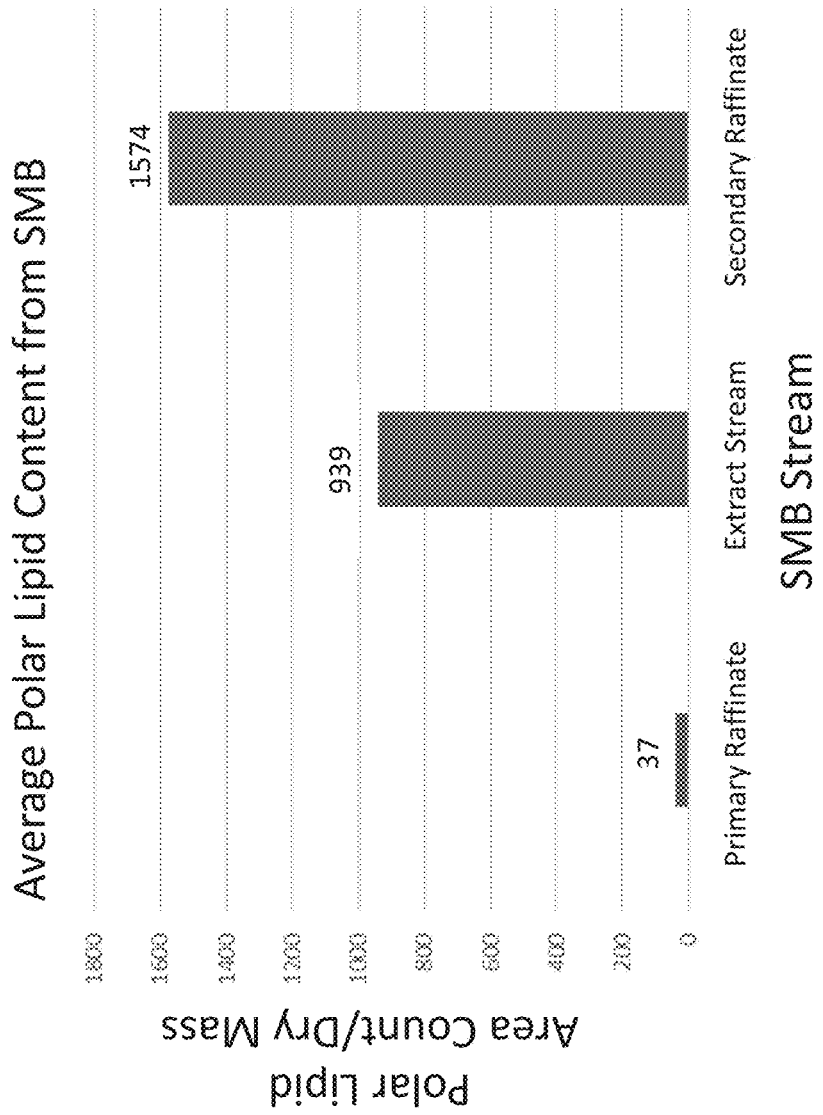
FIG. 17 is a graph showing the PL content of the waste streams from SMB technology with OR-5 as the adsorbent (Extract-XT and Secondary raffinate-SR), which contain 98.5% of the lipids and waxes, while the CBD product is contained in the Primary raffinate (PR), in Example 17.

The decolorized and decarboxylated hemp extract of Example 3 can be used as feed to purify CBD and to remove lipids and waxes along with THC using SMB technology with OR-5 as the adsorbent. In the pilot scale run, 64.1 mg of decolorized and decarboxylated extract was dissolved for every mL of solvent (95/5 v/v Ethanol/Heptane, from Pharmco-Aaper). Eight columns, measuring 6 in. in diameter and 36 in. in length, were connected to the Simulated Moving Bed instrument (from Semba Bioscience—WI, USA). Four pumps (0-2.5 lpm from Tuthil) were also connected to the SMB Instrument. The columns were figured to run in a 2-3-2-1 scheme. The SMB Step time was set at 1210 sec and the system was maintained at 25° C. The flow rates for the above-mentioned streams are tabulated in Table 19. As shown in the graph in FIG. 17, the waste streams (Extract-xt and Secondary raffinate-sr) contain 98.5% of the lipids and waxes, while the CBD product is contained in the Primary raffinate (pr).

Example 18—OR-2 Prime Adsorbent in SMB Technology for THC Removal

The decolorized and decarboxylated hemp extract of Example 3 can be used as feed to purify CBD and to remove THC using SMB technology with C18 as the adsorbent. In the pilot scale run, 35.0 mg of decolorized and decarboxylated extract was dissolved for every mL of solvent (80/20 v/v ethanol:water, from Pharmco-Aaper). Eight columns, measuring 6 in. in diameter and 36 in. in length, were connected to the Simulated Moving Bed instrument (from Semba Bioscience—WI, USA). Four pumps (0-2.5 lpm from Tuthill) were also connected to the SMB Instrument. The SMB Step time was set at 480 sec. and the system was maintained at 60° C. The flow rates for the above-mentioned streams are tabulated in Table 21, while the mass percent of each bulk stream is given in Table 22.

TABLE 21

Flow Rates for the Zones in SMB of Example 18

| | Flow rate (L/min) |
|---|---|
| Desorbent (Zone 1 In) | 2.54 |
| Feed | 0.30 |
| Extract In (Zone 2 In) | 1.62 |
| Intermediate Flow (Zone 3 In) | 0.99 |
| Primary Raffinate (Zone 3 Out) | 0.99 |
| Secondary Raffinate (Zone 4 Out) | 0.23 |

TABLE 22

Mass Percent in Each Bulk Stream in SMB of Example 18

| | Mass Percent (%) | |
|---|---|---|
| SMB Outputs | CBD | THC |
| Extract | 11.1 | 88.04 |
| Primary Raffinate | 88.35 | 11.8 |
| Secondary Raffinate | 0.6 | 0.13 |

As is apparent from the results set forth in Table 22, the majority of the CBDA and CBD is present in the primary raffinate, whereas the majority of the THC is found in the extract stream.

Figure 18:
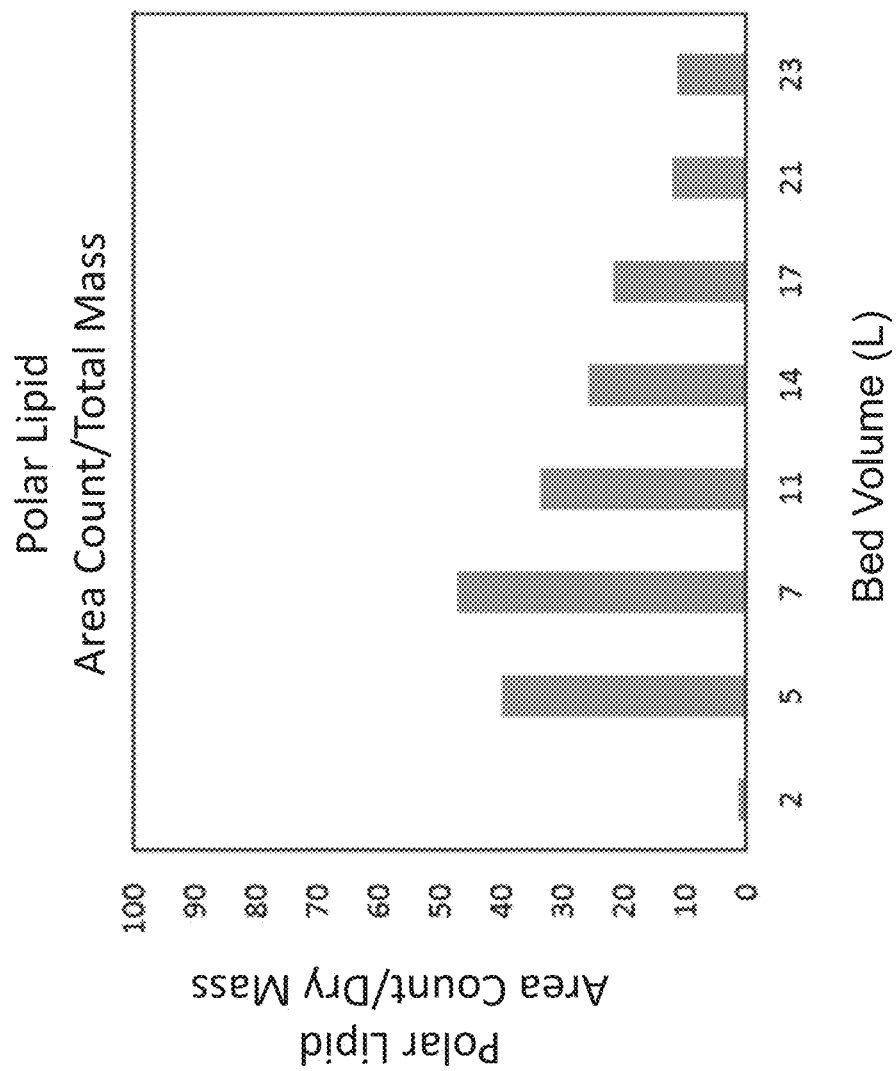
FIG. 18 is a graph showing the polar lipids per dry mass breakthrough versus the bed volumes of feed processed in Example 19.

Example 19—OR-1 Batch Chromatographic Mode Operations for Wax and Polar Lipids Removal The decolorized and decarboxylated hemp extract of Example 3 can be used as feed to purify CBD by removal of THC along with polar lipids and waxes using OR-1 adsorbent in a batch chromatographic mode. In the pilot scale run, 30-40 mg of hemp extract was dissolved for every mL of solvent (95/5 v/v Ethanol/Heptane, from Pharmco-Aaper). The column, measuring 18 in. in diameter and 40 in. in length, was connected to a single pump (0-2.5 lpm from Tuthill). The flow rate was set to 0.5 L per minute and the system was maintained at 25° C. The graph in FIG. 18 shows the polar lipids per dry mass breakthrough versus the bed volumes of feed processed.

Example 20—OR-1 Batch Chromatographic Mode Operations for THC Removal

Figure 19:
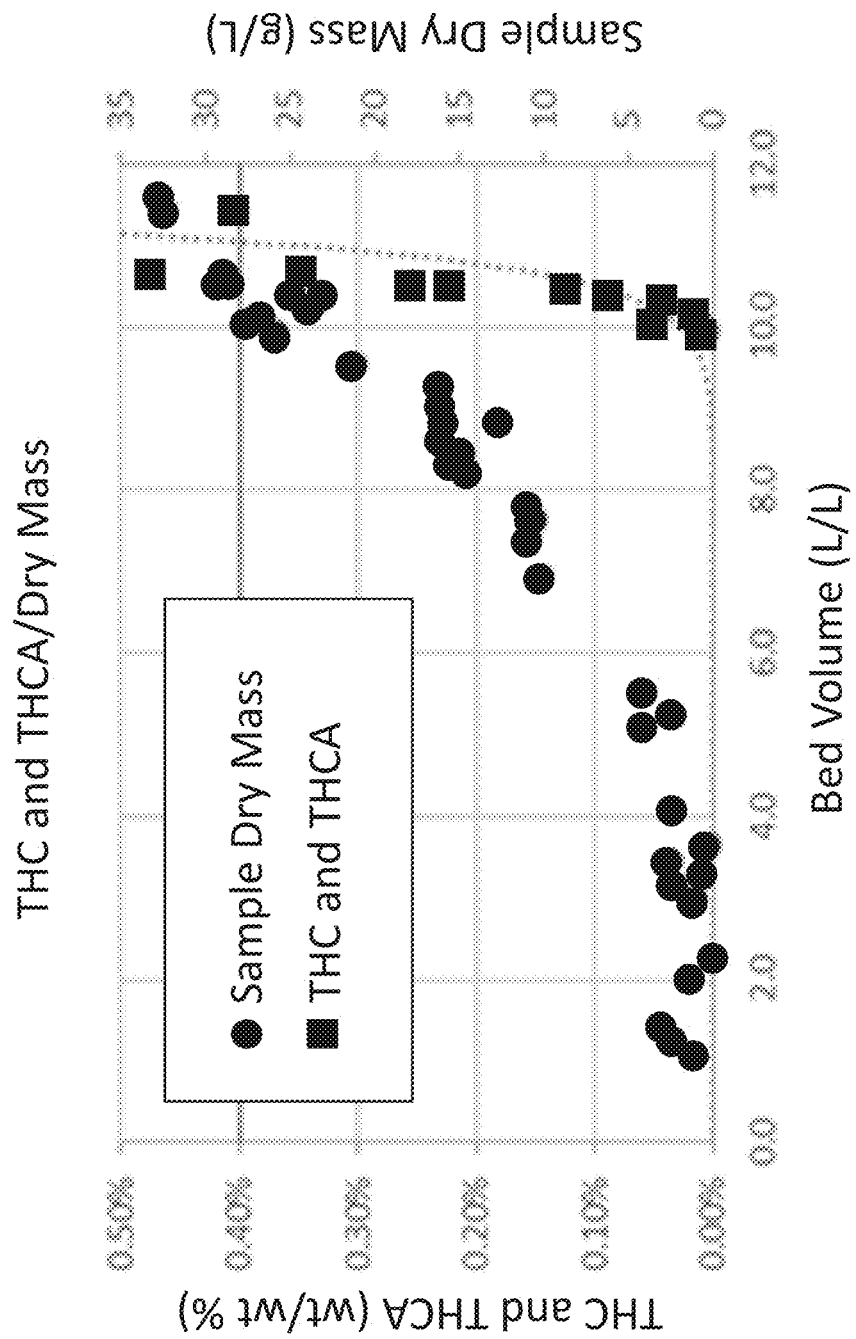
FIG. 19 is a graph showing a plot of THC+THCA (THC+A) in weight % versus bed volume of feed processed in an OR-1 adsorbent in a batch chromatographic mode in Example 20.

The decolorized and decarboxylated hemp extract of Example 3 can be used as feed to purify CBD by removal of THC along with polar lipids and waxes using OR-1 adsorbent in a batch chromatographic mode. In the pilot scale run, 15-30 mg of hemp extract was dissolved for every mL of solvent (95/5 v/v Ethanol/Heptane, from Pharmco-Aaper). The column, measuring 18 in. in diameter and 48 in. in length, was connected to a single pump (0-2.5 lpm from Tuthill). The flow rate was set to 0.5 L per minute and the system was maintained at 25° C. The graph in FIG. 19 shows a plot of THC+THCA (THC+A) in weight % versus bed volume of feed processed. The product collected from bed volume 0 up to bed volume 10 is characterized as THC-free CBD product.

Example 21—OR-2 Prime Single Column for Separation of CBD and THC

Figure 20:
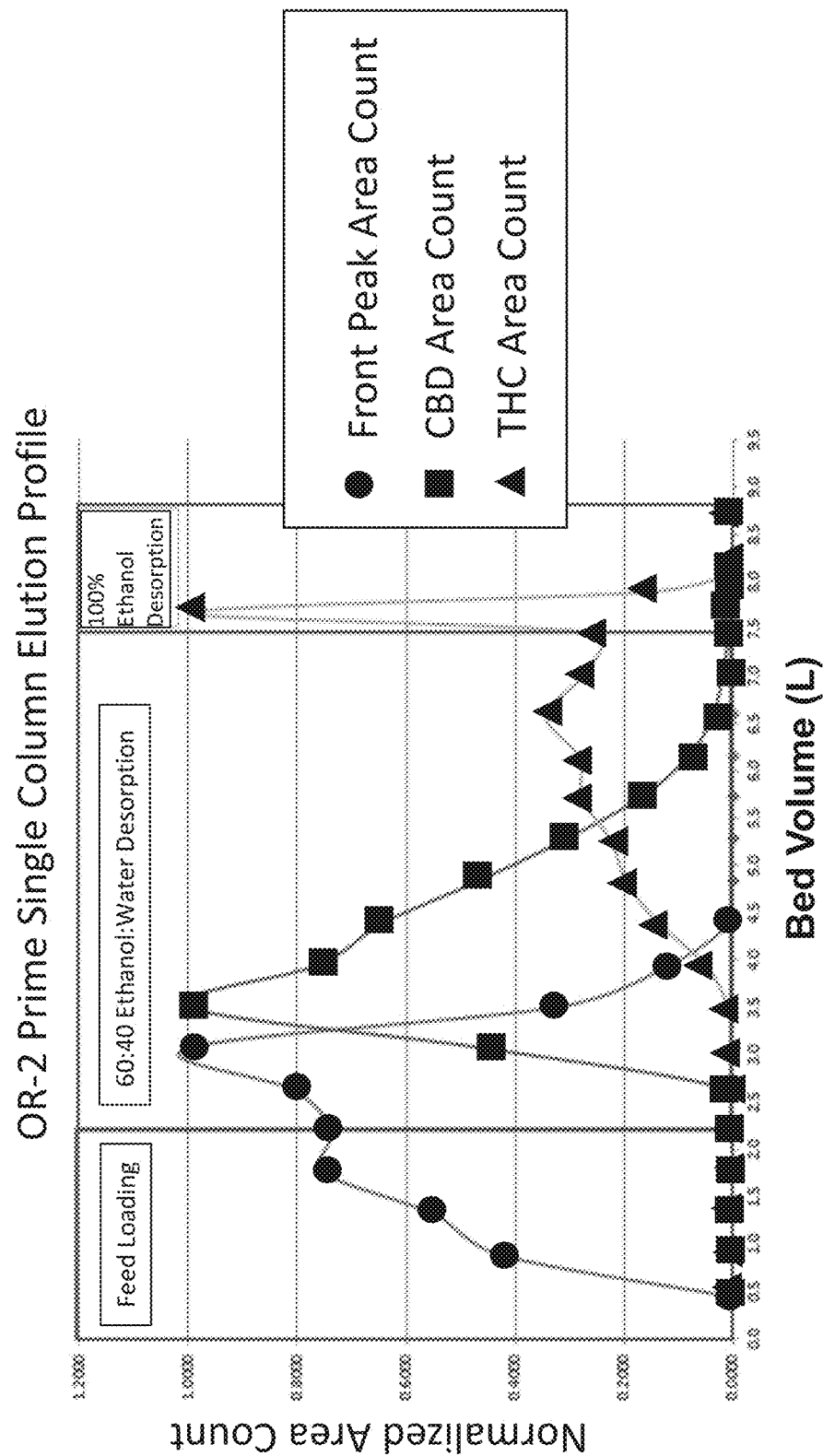
FIG. 20 is a graph showing the detection levels of CBD and THC processed on an OR-2 prime single column during the steps of: feed loading, desorption with ethanol:water 60:40, and desorption with 100% ethanol in Example 21.

The decolorized and decarboxylated hemp extract of Example 3 can be used as feed to purify CBD by removal of THC along with polar lipids and waxes using OR-2 prime adsorbent in a single column chromatographic mode. In the pilot scale run, 20.8 mg of hemp extract was dissolved for every mL of solvent (60:40 ethanol:water). The column, measuring 22 mm in diameter and 300 mm in length, was connected to a single pump (0-100 ml/min from SSI). The feed flow rate was set to 5 mL per minute and the system was maintained at 60° C. The feed was loaded until CBD breakthrough was detected. After detection of CBD, the feed loading was stopped and ethanol:water (50-60)/(50-40) solvent was used to elute out the adsorbed CBD. This solvent was loaded until the CBD detected in the effluent was negligible. Then 100% Ethanol was used to desorb the THC and regenerate the column for the next feed loading step. The graph in FIG. 20 shows the detection levels of CBD and THC during the steps of: feed loading, desorption with ethanol:water 60:40, and desorption with 100% Ethanol.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. As used herein, the term "exemplary" indicates an example thereof and does not suggest a best or optimal of the recited item. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of separating cannabidiolic acid (CBDA) of a *cannabis* plant using simulated moving bed (SMB) chromatography, the *cannabis* plant including the CBDA and at least one impurity, the method comprising:
   preparing a feedstock stream from the *cannabis* plant, the feedstock stream including the CBDA, at least one impurity, and a solvent, and
   passing the feedstock stream through a chromatographic resin arranged in a simulated moving bed (SMB) chromatography configuration to provide a primary raffinate stream,
   wherein the primary raffinate stream has a higher purity of the CBDA than in the feedstock stream as measured by weight percentage of the solid content, and
   wherein the chromatographic resin comprises a hydrophobic polystyrene-divinylbenzene adsorbent.

2. The method of claim 1, wherein the feedstock stream is not decarboxylated.

3. The method of claim 1, wherein said at least one impurity comprises at least one of waxes, lipids, pigments, and mixtures thereof.

4. The method of claim 1, wherein said at least one impurity comprises a second cannabinoid selected from cannabidiol (CBD), cannabigerol (CBG), cannabinol (CBN), tetrahydrocannabinol (THC), tetrahydrocannabinolic acid (THCA), and combinations thereof.

5. The method of claim 1, wherein the feedstock stream comprises a hemp extract, a decolorized hemp extract, or any combination thereof.

6. The method of claim 1, wherein the solvent of the feedstock stream comprises water, ethanol, acetone, ethyl acetate, acetonitrile, pentanes, hexanes, heptanes, methanol, propanol, or a combination thereof.

7. The method of claim 6, wherein the solvent of the feedstock stream comprises ethanol.

8. The method of claim 1, wherein the hydrophobic polystyrene-divinylbenzene adsorbent has:
   (i) an average particle diameter of from about 25 microns to about 600 microns,
   (ii) an average bulk density of from about 0.4 g/mL to about 0.9 g/mL,
   (iii) an average water content of from about 55% to about 65%,
   (iv) an average surface area of from about 450 m²/g to about 550 m²/g,
   (v) an average pore volume of from about 0.7 mL/g to about 0.9 mL/g,
   (vi) from about 4% to about 8% crosslinking, or
   (vii) any combination thereof.

9. The method of claim 8, wherein the feedstock stream is not decarboxylated.

10. The method of claim 8, wherein said at least one impurity comprises at least one of waxes, lipids, pigments, and mixtures thereof.

11. The method of claim 8, wherein said at least one impurity comprises a second cannabinoid selected from cannabidiol (CBD), cannabigerol (CBG), cannabinol (CBN), tetrahydrocannabinol (THC), tetrahydrocannabinolic acid (THCA), and combinations thereof.

12. The method of claim 8, wherein the feedstock stream comprises a hemp extract, a decolorized hemp extract, or any combination thereof.

13. The method of claim 8, wherein the solvent of the feedstock stream comprises water, ethanol, acetone, ethyl acetate, acetonitrile, pentanes, hexanes, heptanes, methanol, propanol, or a combination thereof.

14. The method of claim 13, wherein the solvent of the feedstock stream comprises ethanol.

15. The method of claim 1, wherein the hydrophobic polystyrene-divinylbenzene adsorbent has an average particle diameter of from about 25 microns to about 300 microns.

16. The method of claim 1, wherein the hydrophobic polystyrene-divinylbenzene adsorbent has an average particle diameter of from about 250 microns to about 600 microns.

17. The method of claim 1, wherein the hydrophobic polystyrene-divinylbenzene adsorbent has an average bulk density of from about 0.4 g/mL to about 0.6 g/mL.

18. The method of claim 1, wherein the hydrophobic polystyrene-divinylbenzene adsorbent has an average bulk density of from about 0.6 g/mL to about 0.9 g/mL.

19. The method of claim 1, wherein the hydrophobic polystyrene-divinylbenzene adsorbent has an average water content of from about 55% to about 65%.

20. The method of claim 1, wherein the hydrophobic polystyrene-divinylbenzene adsorbent has an average surface area of from about 450 m²/g to about 550 m²/g.

21. The method of claim 1, wherein the hydrophobic polystyrene-divinylbenzene adsorbent has an average pore volume of from about 0.7 mL/g to about 0.9 mL/g.

22. The method of claim 1, wherein the hydrophobic polystyrene-divinylbenzene adsorbent has from about 4% to about 8% crosslinking.

23. The method of claim 1, wherein the primary raffinate has less than 1 wt. % of tetrahydrocannabinol (THC) and tetrahydrocannabinolic acid (THCA) based on the amount of the CBDA.

24. The method of claim 1, wherein the primary raffinate has less than 0.5 wt. % of tetrahydrocannabinol (THC) and tetrahydrocannabinolic acid (THCA) based on the amount of the CBDA.

25. The method of claim 1, wherein the primary raffinate has less than 0.3 wt. % of tetrahydrocannabinol (THC) and tetrahydrocannabinolic acid (THCA) based on the amount of the CBDA.

26. The method of claim 1, wherein the hydrophobic polystyrene-divinylbenzene adsorbent has an average particle diameter of from about 25 microns to about 600 microns and an average bulk density of from about 0.4 g/mL to about 0.9 g/mL.

27. The method of claim 26, wherein the feedstock stream is not decarboxylated.

28. The method of claim 26, wherein said at least one impurity comprises at least one of waxes, lipids, pigments, and mixtures thereof.

29. The method of claim 26, wherein said at least one impurity comprises a second cannabinoid selected from cannabidiol (CBD), cannabigerol (CBG), cannabinol (CBN), tetrahydrocannabinol (THC), tetrahydrocannabinolic acid (THCA), and combinations thereof.

30. The method of claim 26, wherein the feedstock stream comprises a hemp extract, a decolorized hemp extract, or any combination thereof.

31. The method of claim 26, wherein the solvent of the feedstock stream comprises water, ethanol, acetone, ethyl acetate, acetonitrile, pentanes, hexanes, heptanes, methanol, propanol, or a combination thereof.

32. The method of claim 31, wherein the solvent of the feedstock stream comprises ethanol.

33. The method of claim 26, wherein the hydrophobic polystyrene-divinylbenzene adsorbent further has an average water content of from about 55% to about 65%.

34. The method of claim 26, wherein the hydrophobic polystyrene-divinylbenzene adsorbent further has an average surface area of from about 450 $m^2/g$ to about 550 $m^2/g$.

35. The method of claim 26, wherein the hydrophobic polystyrene-divinylbenzene adsorbent further has an average pore volume of from about 0.7 mL/g to about 0.9 mL/g.

36. The method of claim 26, wherein the hydrophobic polystyrene-divinylbenzene adsorbent further has an average surface area of from about 450 $m^2/g$ to about 550 $m^2/g$.

37. The method of claim 26, wherein the hydrophobic polystyrene-divinylbenzene adsorbent further has from about 4% to about 8% crosslinking.

38. The method of claim 26, wherein the primary raffinate has less than 1 wt. % of tetrahydrocannabinol (THC) and tetrahydrocannabinolic acid (THCA) based on the amount of the CBDA.

39. The method of claim 26, wherein the primary raffinate has less than 0.5 wt. % of tetrahydrocannabinol (THC) and tetrahydrocannabinolic acid (THCA) based on the amount of the CBDA.

40. The method of claim 26, wherein the primary raffinate has less than 0.3 wt. % of tetrahydrocannabinol (THC) and tetrahydrocannabinolic acid (THCA) based on the amount of the CBDA.

* * * * *